(12) United States Patent
Koelle et al.

(10) Patent No.: US 11,713,482 B2
(45) Date of Patent: Aug. 1, 2023

(54) COMPOSITIONS, METHODS AND DEVICES COMPRISING STEM-LOOP CAPTOR MOLECULES

(71) Applicant: GENECAPTURE, INC., Huntsville, AL (US)

(72) Inventors: Paula M. Koelle, Huntsville, AL (US); Krishnan Chittur, Huntsville, AL (US); Valentin Korman, Huntsville, AL (US); Zachary McGee, Huntsville, AL (US)

(73) Assignee: GENECAPTURE, INC., Huntsville, AL (US)

(*) Notice: Subject to any disclaimer, the term of this patent is extended or adjusted under 35 U.S.C. 154(b) by 246 days.

(21) Appl. No.: 16/310,273

(22) PCT Filed: Jun. 15, 2017

(86) PCT No.: PCT/US2017/037806
§ 371 (c)(1),
(2) Date: Dec. 14, 2018

(87) PCT Pub. No.: WO2017/218858
PCT Pub. Date: Dec. 21, 2017

(65) Prior Publication Data
US 2020/0354779 A1 Nov. 12, 2020

Related U.S. Application Data

(60) Provisional application No. 62/382,754, filed on Sep. 1, 2016, provisional application No. 62/350,689, filed on Jun. 15, 2016.

(51) Int. Cl.
*C12Q 1/6837* (2018.01)
*C12Q 1/6816* (2018.01)

(52) U.S. Cl.
CPC ......... *C12Q 1/6837* (2013.01); *C12Q 1/6816* (2013.01); *C12Q 2525/197* (2013.01); *C12Q 2525/301* (2013.01); *C12Q 2565/513* (2013.01)

(58) Field of Classification Search
CPC .......... B01L 2300/0877; C12Q 1/6834; C12Q 1/6837; C12Q 1/6876; C12Q 1/6816; C12Q 2525/301; C12Q 2565/513
See application file for complete search history.

(56) References Cited

U.S. PATENT DOCUMENTS

| | | | |
|---|---|---|---|
| 2002/0182687 A1 | 12/2002 | Kurz et al. | |
| 2004/0110141 A1* | 6/2004 | Pusey | C12Q 1/6837 435/6.1 |
| 2006/0057564 A1 | 3/2006 | Wang | |
| 2006/0199183 A1* | 9/2006 | Valat | C12Q 1/6883 435/6.15 |
| 2012/0321518 A1* | 12/2012 | Ermantraut | C12Q 1/6834 422/69 |
| 2013/0260368 A1* | 10/2013 | Pollner | C12Q 1/6837 435/5 |
| 2015/0045254 A1 | 2/2015 | Jack et al. | |
| 2015/0133317 A1 | 5/2015 | Robinson et al. | |

FOREIGN PATENT DOCUMENTS

| | | | |
|---|---|---|---|
| CN | 103184297 A | | 7/2013 |
| CN | 104169438 A | | 11/2014 |
| CN | 105223250 A | | 1/2018 |
| WO | 2004083225 A2 | | 9/2004 |
| WO | 2007/023461 A2 | | 3/2007 |
| WO | 2009039549 A2 | | 4/2009 |
| WO | WO 2013/116774 | * | 8/2013 |
| WO | 2014/197607 A1 | | 12/2014 |

OTHER PUBLICATIONS

Boateng et al., "Dendron-modified surfaces provide an ideal environment for stem-loop DNA probes", (2012) Anal. Biochem. 430: 39-44 (Year: 2012).*
Du et al., "Sensitivity and specificity of metal surface-immobilized 'molecular beacon' biosensors", (2005) J. Am. Chem. Soc 127: 7932-7940 (Year: 2005).*
Aitkin et al., "An oxygen scavenging system for improvement of dye stability in single-molecule fluorescence experiments", (2008) Biophys J. 94: 1826-1835 (Year: 2008).*
Supplementary Partial European Search Report issued in corresponding European application No. 17814146.1, dated Feb. 12, 2020, 11 pages.
Bockisch Benjamin et al. "Immobilized stem-loop structured probes as conformational switches for enzymatic detection of microbial 16S rRNA," Nucleic Acids Research Advance Access, Oxford University Press, GB, vol. 33, No. 11, Jan. 1, 2005.
GenBank Accession No. CU466399. Sus scrofa chromosome 15 clone CH242-393J6, Working Draft Sequence, 9 unordered pieces. https://www.ncbi.nlm.nih.gov/nuccore/CU466399.
GenBank Accession No. CU467805. Sus scrofa chromosome 4 clone CH242-92C1, Working Draft Sequence, 3 unordered pieces. https://www.ncbi.nlm.nih.gov/nuccore/CU467805.

(Continued)

*Primary Examiner* — Narayan K Bhat
(74) *Attorney, Agent, or Firm* — Meunier Carlin & Curfman LLC

(57) ABSTRACT

Disclosed herein are methods, devices and compositions comprising nucleic acid captor molecules with a stem region and a loop region for detecting target nucleic acids.

21 Claims, 16 Drawing Sheets

Specification includes a Sequence Listing.

(56) References Cited

OTHER PUBLICATIONS

GenBank Accession No. LL035905. Trichobilharzia regenti genome assembly T_regenti_v1_0_4, scaffold TRE_scaffold0035708. https://www.ncbi.nlm.nih.gov/nuccore/LL035905.

GenBank Accession No. AF162137. Mus musculus WNT-2 gene, partial cds; putative ankyrin-related protein and cystic fibrosis transmembrane conductance regulator (CFTR) genes, complete cds; and unknown gene. https://www.ncbi.nlm.nih.gov/nuccore/AF162137.

GenBank Accession No. AC116088. Rattus norvegicus clone CH230-343I4, Working Draft Sequence, https://www.ncbi.nlm.nih.gov/nuccore/AC116088.

GenBank Accession No. KU547794. Uncultured bacterium clone PE_10F_Contig_8 genomic sequence. https://www.ncbi.nlm.nih.gov/nuccore/KU547794.

International Search Report and Written Opinion of the U.S. International Searching Authority. PCT Application No. PCT/US2017/037806. dated Oct. 30, 2017. 18 pages.

First Examination Report issued in corresponding Indian Application No. 201817048682, dated Jan. 29, 2021.

Office Action in connection to CN Application No. 201780050426X, dated Dec. 1, 2021.

\* cited by examiner

SEQ ID NO:1
5' GACAGACAGACAGAC [ACTCAAGCTTGCCAGTATCAGATGC] TGTCTGTCTGTCTGTC 3'
Structure IV
FIG. 17
SEQ ID NO:25
5' GACAGACAGACAGAC [C] CATACCAGTTTACCTTCCGTACGC [G] GTCTGTCTGTCTGTC 3'
Structure V
FIG. 18
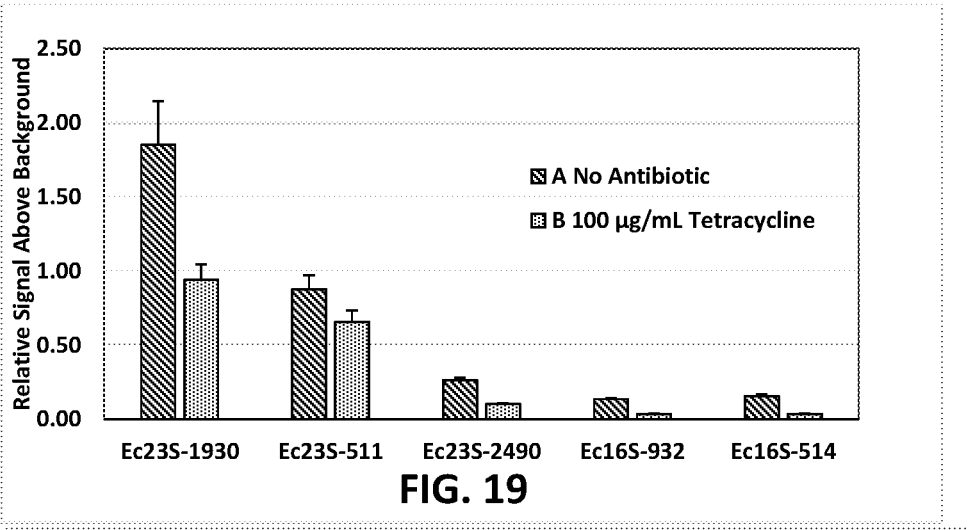
FIG. 19
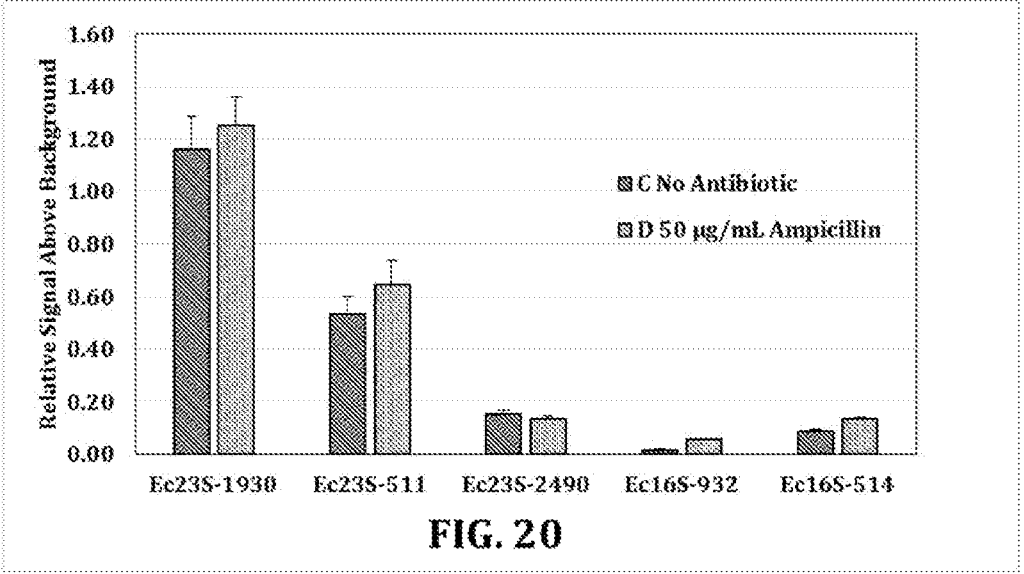
FIG. 20

COMPOSITIONS, METHODS AND DEVICES COMPRISING STEM-LOOP CAPTOR MOLECULES

RELATED APPLICATIONS

This application is a national stage application filed under 35 U.S.C. § 371 of PCT/US2017/037806 filed Jun. 15, 2017, which claims the priority of U.S. Provisional Patent Application No. 62/350,689, filed Jun. 15, 2016, and U.S. Provisional Application No. 62/382,754, filed Sep. 1, 2016, each of which is incorporated by reference herein in its entirety.

REFERENCE TO A SEQUENCE LISTING SUBMITTED

The Sequence Listing submitted Jun. 15, 2017 as a text file named "31933_113823_2P1_SeqListing.txt", created on Jun. 15, 2017, and having size of 62,305 bytes is hereby incorporated by reference pursuant to 37 C.F.R. § 1.52(e)(5).

GOVERNMENT LICENSE RIGHTS

This invention was made with government support under Contract HDTRA1-16-C-0061 awarded by the Chemical Biological Defense Agency and contracted through the Defense Threat Reduction Agency. The government has certain rights in the invention.

BACKGROUND

Methods of detecting specific nucleic acids are of ever increasing importance in the fields of molecular biology, diagnostics, and medicine. There currently exist several methods for detecting and identifying nucleic acids within biological samples. The reasons for selecting one method over another are varied, and include, among others, the cost or availability of reagents or equipment, the transportability of the reagents or equipment, the desire to minimize the time spent or the number of steps, the accuracy or sensitivity for a certain application, the ease of analysis, the ability to automate the process, and the number of nucleic acids to be simultaneously targeted.

There are multiple applications for the detection of nucleic acids in the art, and new applications are always being developed. The ability to detect and quantify nucleic acids is useful in detecting and identifying organisms or viruses, in determining gene expression levels in organisms, or in determining the levels of small RNAs, such as small interfering RNAs (siRNAs), and thus affects many fields, including human and veterinary medicine, food processing, and environmental testing.

Many currently available nucleic acid detection techniques depend upon amplification of the target sequence in order to achieve the desired sensitivity and speed. Currently, most of these amplification methods require the use of specific amplification instrumentation requiring a laboratory environment. Moreover, these methods typically use temperature sensitive reagents that require appropriate storage equipment such as refrigerators or freezers for maintaining the integrity of the reagants used in the amplification assays. Accordingly, biological samples are typically collected remotely and shipped or transported to a facility for analysis using such nucleic acid amplification methods.

Unfortunately, current amplification methods for nucleic acid detection—due to the foregoing limitations—are not useful in a variety of settings that require sensitive detection of nucleic acids immediately and/or at the site of sample collection. For example, during an epidemic or pandemic outbreak it may be critical to be able to rapidly and sensitively detect infectious bacterial, viral, or fungal agents within environmental samples or biological samples of tissue, sputum, urine, blood, semen, or saliva in a field setting that does not have the appropriate laboratory facility available. In a further example, both civilians and combatants may be exposed to naturally occurring or man-made infectious agents in a battlefield setting without access to a laboratory facility. Appropriate diagnosis and treatment can require rapid and sensitive detection of nucleic acids in such a battlefield setting where samples are collected. Current amplification methods are not readily amenable to these types of environments.

Despite advances in nucleic acid detection research, there is still a scarcity of compositions, methods and devices to rapidly and sensitively detect nucleic acids in an environment outside a laboratory, such as in a field environment or a conflict setting. These needs and other needs are satisfied by the present disclosure.

SUMMARY

In accordance with the purpose(s) of the present disclosure, as embodied and broadly described herein, the present disclosure, in one aspect, relates to devices, compositions, kits, methods, and systems for rapidly and sensitively detecting the presence of one or more target nucleic acid sequences within an environmental or biological sample, using a captor molecule and a labeled probe, both comprised of nucleic acids.

Disclosed herein are compositions comprising a disclosed captor molecule.

Disclosed herein are labeled nucleic probes comprising a label linked to a nucleic acid comprising a disclosed probe sequence nucleic acid.

Disclosed herein are compositions comprising a captor molecule disclosed herein and a labeled probe disclosed herein.

Disclosed herein are devices comprising at least one captor molecule covalently linked to a surface of the device.

Disclosed herein are methods for detecting a target nucleic acid in a sample, comprising binding a captor molecule to a target nucleic acid of a sample.

Disclosed herein are kits comprising at least one of: (a) a nucleic acid captor molecule comprising a loop region and a stem region, wherein the nucleic acid captor molecule has a closed stem-loop structure; and wherein the closed stem-loop structure is replaced with an open stem-loop structure when the nucleic acid captor molecule contacts a target nucleic acid; or (b) a labeled probe; wherein the labeled probe comprises a disclosed probe sequence linked to a disclosed label; and wherein the labeled probe binds to the stem region of the open stem-loop structure; and optionally comprising one or more of (c) an incubation buffer; (d) a rinsing buffer; (e) a final rinse buffer; and (f) instructions for one or more of incubating and rinsing the nucleic acid captor molecule with a sample, incubating and rinsing after adding the labeled nucleic acid probe and final rinsing before detecting the presence of the labeled nucleic acid probe.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

This invention is described with respect to specific aspects thereof. The present disclosure is described with reference to the accompanying drawings. In the drawings, like reference numbers indicate identical or functionally similar elements.

FIG. 17 shows a representative self-complementary double-stranded captor molecule, designated Structure (IV).

FIG. 18 shows a representative self-complementary double-stranded captor molecule, designated Structure (V).

FIG. 19 is a graph showing exemplary measurements of bacterial antibiotic sensitivity.

FIG. 20 is a graph showing exemplary measurements of bacterial antibiotic sensitivity.

Figure 1A:
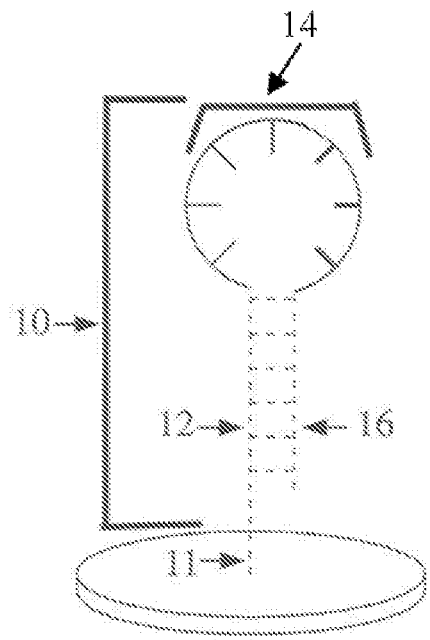
FIG. 1(A) is a representative schematic showing a closed stem-loop captor molecule attached to a substrate, according to various aspects of the present disclosure.

Additional advantages of the present disclosure will be set forth in part in the description which follows, and in part will be obvious from the description, or can be learned by practice of the present disclosure. The advantages of the present disclosure will be realized and attained by means of the elements and combinations particularly pointed out in the appended claims. It is to be understood that both the foregoing general description and the following detailed description are exemplary and explanatory only and are not restrictive of the present disclosure, as claimed.

DETAILED DESCRIPTION

The present disclosure can be understood more readily by reference to the following detailed description of the present disclosure and the Examples included therein.

Definitions

As used in the specification and the appended claims, the singular forms "a," "an" and "the" include plural referents unless the context clearly dictates otherwise. Thus, for example, reference to "a captor molecule," "a target nucleic acid," or "a labeled probe" includes mixtures of two or more such captor molecules, target nucleic acids, or labeled probes, and the like.

The transitional term "comprising" is synonymous with "including," "containing," or "characterized by," is inclusive or open-ended and does not exclude additional, unrecited elements or method steps. It is also to be understood that the terminology used herein is for the purpose of describing particular aspects only and is not intended to be limiting. As used in the specification and in the claims, the term "comprising" can include the aspect of "consisting of." Unless defined otherwise, all technical and scientific terms used herein have the same meaning as commonly understood by one of ordinary skill in the art to which the disclosed compositions and methods belong. In this specification and in the claims which follow, reference will be made to a number of terms which shall be defined herein. The transitional phrase "consisting of" excludes any element, step, or ingredient not specified in the claim, but does not exclude additional components or steps that are unrelated to the present disclosure such as impurities ordinarily associated with a composition.

The transitional phrase "consisting essentially of" limits the scope of a claim to the specified materials or steps and those that do not materially affect the basic and novel characteristic(s) of the claimed invention.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about," "approximate," and "at or about" mean that the amount or value in question can be the exact value designated or a value that provides equivalent results or effects as recited in the claims or taught herein. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or can not occur, and that the description includes instances where said event or circumstance occurs and instances where it does not.

As used herein, the term "agent" refers to a biological agent of interest including viruses, bacteria, fungi, protozoa, animals, cancer cells, blood cells, or other cellular or particulate entities, such as small RNA complexes or other nucleic acids, without or without proteins or other molecules.

As used herein, the term "altering the complementarity" refers to creating one or more bulges or mismatched bases in an otherwise complementary sequence.

As used herein, the term "application of a magnetic field" refers to bringing a magnet in close proximity to a sample or to turning on an electromagnet so that the sample experiences the forces of the magnetic field.

As used herein, the term "attached" means coupling together, or creating a chemical bond between, two chemical or macromolecular entities.

As used herein, the term "bound" refers to the formation of a double-stranded complex between two nucleic acids, and may be referred to as "hybridized" as is understood by those with skill in molecular biology. For example, a nucleic acid captor molecule is "bound" to a nucleic acid probe when a double-stranded complex forms between the captor molecule and the probe. In a further example, a nucleic acid captor molecule is "bound" to a nucleic acid target when a double-stranded complex forms between the captor molecule and target.

As used herein, the terms "captor molecule," "captor molecule nucleic acid," "nucleic acid captor molecule," "stem-loop captor molecule" can be used interchangeably, and refer to a nucleic acid that can be attached to a substrate. The captor molecule is comprised of three major regions: a first stem region, a loop region, and a second stem region.

As used herein, the terms "closed stem-loop structure" and "closed stem-loop" can be used interchangeably, and refer to the binding of the first stem region (e.g. the 5' stem region sequence) to the second stem region (e.g. the 3' stem region sequence) to fold the captor molecule into a hairpin formation. A substantially closed stem loop structure means greater than fifty percent (50%) of the stem loop molecules have duplex formation between the two stem loop regions (i.e., between the 5' stem region sequence and the 3' stem region sequence).

As used herein, "complementary nucleic acids" or "nucleic acid complementarity" refers to a base sequence in one strand of nucleic acid that, due to orientation of its functional groups, binds to a base sequence in an opposing strand, e.g., by hydrogen bonding between A and T or U bases, and between C and G bases. Fully complementary means that a sequence that can form a double helix with a second sequence where the resulting double helix contains no mismatches. Substantially complementary means that a base sequence in one strand is not completely or perfectly complementary to a base sequence in an opposing strand, but that sufficient bonding occurs between bases of the two strands to form a stable hybridized complex in a set of conditions (e.g., salt concentration in an aqueous solution, or a temperature). Such conditions may be predicted by using the base sequences and standard mathematical calculations known to those skilled in the art for determining the melting temperature ($T_m$) at which 50% of hybridized strands are denatured, or by empirical determination of Tm by using routine methods (e.g., see Sambrook et al., Molecular Cloning, A Laboratory Manual, 2nd Ed., (Cold Spring Harbor Laboratory, Cold Spring Harbor, N.Y., 1989), at 9.50-51, 11.46-49, 11.55-57).

As used herein, the term "color-producing conjugated proteins" refers to proteins, such as horseradish peroxidase, which can catalyze the conversion of chromogenic compounds into colored products or produce light when acting on chemiluminescent compounds.

As used herein, the term "fluorophore" refers to a molecule can emit fluorescent light of a defined wavelength upon exposure to the light with an excitation wavelength.

As used herein, the term "half the length of the average closed captor molecule" refers to the arithmetic mean of the molecular length of a plurality of captor molecules applied to the substrate.

As used herein, a "hybridization condition" refers to the cumulative environment in which one nucleic acid strand bonds to a second nucleic acid strand by complementary strand interactions to produce a hybridization complex. Such conditions include, e.g., temperature, chemical components and concentrations of compounds (e.g., salts, buffers, chelating agents, organic compounds) in aqueous and/or organic solutions that contain the nucleic acids.

As used herein, the term "inhibit nuclease activity" refers to inactivating an enzyme that is capable of cleaving a phosphodiesterase bond in a nucleic acid. The nuclease that is inhibited can be either an exonuclease or an endonuclease.

As used herein, a "label" refers to a molecular moiety that is detectable or produces a detectable response directly or indirectly, e.g., by catalyzing a reaction that produces a signal. Labels include luminescent moieties (e.g., fluorescent, bioluminescent, or chemiluminescent compounds), radioisotopes, members of binding pairs (e.g., biotin and avidin or streptavidin), enzymes or enzyme substrates, reactive groups or chromophores, e.g., a dye or particle that results in a detectable color. A detectable response or signal is any perceptible or measurable output that indicates the presence of a label, e.g., light, color, radioactive decay emission, electrical signal, magnetic field, or signal blockage, such as from quenching or turbidity.

As used herein, the terms "labeled probe" and "nucleic acid probe" can be used interchangeably, and refer to a nucleic acid that is complementary to a portion of the sequence of the first stem region (e.g., 5' stem region sequence) or the second stem region (e.g., 3' stem region sequence) of the captor molecule, which portion is only exposed upon the binding of the target nucleic acid to the captor molecule.

As used herein, the term "locked nucleic acids" or "LNA" refers to a nucleotide analog in which the ribose ring is locked in an ideal conformation for forming a double helix.

As used herein, the term "loop region" refers to the sequence of the nucleic acid captor molecule that is between the stem regions (5' stem region sequence and 3' stem region sequence) and that is complementary to at least a portion of a target nucleic acid.

As used herein, the terms "melting temperature of a nucleic acid," "melted nucleic acid," or "melted duplex" can be used interchangeably, and refer to a temperature at which half of the nucleic acids will be bound to their complementary sequences, and conversely, half the nucleic acids of a double-stranded nucleic acid molecule are in a single-stranded state. For example, "melting temperature of the target nucleic acids" refers to a temperature at which half of a population of target nucleic acids would be bound to captor molecules.

As used herein, the term "nanoparticle" refers to particles having an average particle size of less than about 100 nanometers. Nanoparticles can be functionalized with nucleic acids, proteins or other molecules.

As used herein, the term "nucleic acid" refers to a molecule such as a DNA, RNA, LNA or PNA molecule as described herein, or a molecule containing combinations of DNA, RNA, LNA, and/or PNA. In addition, it is understood that "nucleic acid" includes other types of DNA analogs, RNA analogs, and mixed DNA-RNA polymers or oligomers known to the skilled artisan, made up of at least two nucleic acid bases, or ten or more bases linked by a backbone structure. DNA and RNA may be made up of the common bases or nucleotides (A, T, G and C for DNA, and A, G, C and U for RNA), although base analogs (e.g., inosine) and a basic positions (i.e., a phosphodiester backbone that lacks a nucleotide at one or more positions, see U.S. Pat. No. 5,585,481) are also included in these terms. Nucleic acids or nucleotides disclosed herein include molecules that function as nucleotides or function in nucleic acid polymers, including but not limited to, nucleic acids, such as known forms of DNA and RNA as well as a number of nucleic acid analogues such as PNA, HNA, MNA, ANA, LNA, INA, CNA, CeNA, TNA, (2'-NH)-TNA, (3'-NH)-TNA, alpha-L-Ribo-LNA, alpha-L-Xylo-LNA, beta-D-Xylo-LNA, alpha-D-Ribo-LNA, [3.2.1]-LNA, Bicyclo-DNA, 6-Amino-Bicyclo-DNA, 5-epi-Bicyclo-DNA, .alpha.-Bicyclo-DNA, Tricyclo-DNA, Bicyclo[4.3.0]-DNA, Bicyclo[3.2.1]-DNA, Bicyclo[4.3.0]amide-DNA, beta-D-Ribopyranosyl-NA, alpha-L-Lyxopyranosyl-NA, 2'-R.sub.1-RNA, 2'-OR$_1$—RNA (R1 being any substituent), alpha-L-RNA, alpha-D-RNA, beta-D-RNA and others such as those capable of specifically hybridizing to complementary nucleic acid strands. For example, nucleic acid structures such as nucleotide analogs taught in U.S. Pub. No 20100068704 or WO/2017/045689 may be present in disclosed nucleic acid polymers. (See Pentabase, 500 Odense, Denmark).

As used herein, "nucleic acid backbone" refers to groups or linkages known in the art (Eschenmoser, 1999, Science 284:2118-2124), e.g., sugar-phosphodiester linkages, 2'-O-methyl linkages, guanidine linkers in DNA ("DNG"), S-methylthiourea linkers, methylphosphonate linkages, phosphoramidate linkages, amide backbone modifications as in polyamide or peptide nucleic acids (PNA), phosphorothioate linkages, phosphonic ester nucleic acid linkages, pyranosyl oligonucleotide linkages, bicyclo- and tricyclo-nucleic acid linkages, formacetal and 3'-thioformacetal linkages, morpholino linkages, or other modifications of the natural phosphodiester internucleoside bond, or combinations thereof, as is well-known in the art. For example, see Majlessi et al., 1998, Nucl. Acids Res. 26(9): 2224-2229; Dempcy et al., 1995, A nucleic acid backbone may include a mixture of linkages in the same oligomer or polymer (e.g., one or more sugar-phosphodiester linkages and one or more 2'-O-methyl linkages in the strand) or may have the same linkages throughout the strand (e.g., all 2'-O-methyl or all amide modification linkages).

As used herein, the term "nucleic acid detector" refers to a detectable moiety as disclosed herein. Such a detectable moiety or label can be associated with a captor molecule, a probe molecule or both. Detectable moieties or labels are used in, but not limited to, (a) a system for indicating the presence of a target nucleic acid, for example, using a captor molecule and a labeled probe in which a labeled probe binds to a captor molecule if the captor molecule has hybridized with a target nucleic acid; (b) a method to determine the presence of a target nucleic acid, for example, using a captor molecule and a labeled probe in which a labeled probe binds to a captor molecule if the captor molecule has hybridized with a target nucleic acid; (c) a composition comprising a captor molecule or one or more captor molecules, which can be used to detect nucleic acids, such as target nucleic acids, in methods, devices, and/or systems disclosed herein, or (d) a device comprising at least one captor molecule attached to a substrate, and optionally, a probe, for example, a labeled probe binds to a captor molecule if the captor molecule has hybridized with a target nucleic acid.

As used herein, the terms "open stem-loop structure" and "open conformation" can be used interchangeably, and refer to the conformation of the captor molecule following the binding of the target nucleic acid to the captor molecule which disrupts the hairpin formation of the captor molecule by releasing the binding of the stem regions to each other and somewhat linearizes the captor molecule. Binding of the target nucleic acid by a captor results in a stem region of the captor being available for binding of probe molecule.

As used herein, the term "paramagnetic microbeads" refers to beads with a diameter of $1 \times 10^{-1}$ to $1 \times 10^{3}$ μm containing a paramagnetic core and an outer coating that can be functionalized with nucleotides or proteins. Paramagnetic microbeads have the ability to respond by aligning with an applied magnetic field and lose their alignment when the applied magnetic field is removed. Neither hysteresis nor residual magnetization (alignment) is experienced by the paramagnetic microbeads. When the field is removed, the paramagnetic microbeads demagnetize and re-disperse in the medium. This allows for rapid and efficient rinsing, resulting in low background and good reproducibility. The behavior of the paramagnetic microbeads is the same irrespective of the prior magnetization cycles.

As used herein, the terms "peptide nucleic acids" and "PNA" can be used interchangeably, and refer to a nucleotide analog in which the natural sugar-phosphate backbone has been replaced with a synthetic peptide backbone.

As used herein, the term "probe complementary region" refers to a sequence on the captor molecule to which the probe is complementary.

As used herein, the term "quantum dot" refers to a composition comprising crystals of a semiconductor material with a diameter on the order of several nanometers. A quantum dot has a characteristic ability to convert incident light into emitted light of a particular wavelength.

As used herein, the term "rinsing" is used in its generally understood definition. Such as in a step of contacting a captor molecule with a medium that does not contain other reaction elements, such as a nucleic acid target or a nucleic acid probe.

As used herein, the term "sample" refers to a mixture potentially containing at least one target nucleic acid. The mixture can be homogeneous or heterogenous, and can be in solid or liquid form. A sample that is a solid, e.g., a powder, can be solubilized or extracted prior to use in a disclosed method. The sample can comprise an agent that comprises a target nucleic acid, a target nucleic acid that is not localized within an agent at the time of sample, or a combination of both. Sources of samples can be, but are not limited to, environmental, human, plant, microbial or animal, and for example, can include bodily fluids, tissue or other portions of a human, plant, microbial or animal.

As used herein, the term "self-complementary double-stranded structure" refers to a length of nucleic acid sequences that can form a double-stranded structure.

As used herein, the term "small organic molecule" refers to a carbon-containing compound that is generally understood to have a molecular weight of less than about 5,000 Daltons.

As used herein, the term "stem region" refers to the 5' sequence and/or 3' sequence of a nucleic acid captor molecule, for example, a 5' stem region sequence may be complementary to and can form a double-stranded complex with a 3' stem region sequence.

As used herein, the term "substrate" or "support" refers to a surface on or within a device, e.g., a microscope slide, a plate well, a microfluidic chamber, a fiber, a wire, a particle, a bead, a matrix, and the like, to which a captor molecule can be attached. A substrate can be made from a variety of materials, e.g., glass, nitrocellulose, nylon, polyacrylate, mixed polymers, polystyrene, silane polypropylene, paramagnetic materials, and magnetic materials.

As used herein, the term "target-captor molecule duplex" refers to a captor molecule with at least a portion of its loop section bound to a complementary portion of a target nucleic acid.

As used herein, the terms "target nucleic acid" and "target molecule" can be used interchangeably, and refer to a nucleic acid comprising a target sequence that can bind to a complementary sequence of a captor molecule, and thus, be detected using the disclosed nucleic acids and methods. The target sequence can be a disclosed target sequence.

Compositions

In an aspect, the present disclosure relates to compositions that can be used for rapidly and sensitively detecting the presence of one or more target nucleic acid sequences within an environmental or biological sample.

In an aspect, the present disclosure relates to compositions comprising one or more probes, for example, labeled probes comprising a known or disclosed label linked to a nucleic acid probe, for example, comprising a disclosed nucleic acid probe sequence. Use of multiple captor molecules having stem regions with at least a portion of their stem regions having identical sequences allows use of a labeled probe with a complementary sequence that can bind to all of the stem regions available, e.g., a "universal labeled probe" that binds to an exposed stem region of the captor molecules regardless of the sequence of the loop region of the captor molecule. Thus, a universal labeled probe can be used with an assay, where all labeled probes have identical sequences. Use of a universal labeled probe simplifies the detection process by requiring the preparation of only a single labeled probe sequence. As used herein, "universal probe" means a probe, whether labeled or not, that is capable of binding to the stem region sequence of a multiplicity of captor molecules.

In an aspect, a detectable label can be linked to the 5' end, 3' end, or both the 5' end and 3' end of the nucleic acid comprising a probe sequence. In an aspect, a detectable label is, but is not limited to, a radionuclide, a fluorophore, a quantum dot, a labeled-nanoparticle or a color-producing conjugated protein. Detectable labels for nucleic acid sequences are known to those of skill in the art. The presence of a detectable label can be detected using a suitable measuring device or assay for the type of label used. In an aspect, two or more radionuclides or two or more fluorophores which either absorb excitation and/or emit fluorescence at two or more frequencies can be used to detect multiple target nucleic acids.

In an aspect, the present disclosure relates to compositions comprising a captor molecule. In an aspect, a captor molecule is a nucleic acid structure with a loop segment sequence that is complementary to at least a portion of a target nucleic acid and the loop segment sequence can hybridize to at least a portion of the target nucleic acid sequence under assay conditions. In an aspect, hybridization of the captor molecule to the target nucleic acid maintains the captor molecule in an open conformation that exposes an end portion of the captor molecule to a labeled probe. In an aspect, the labeled probe is able to hybridize with the exposed end portion of the captor molecule, in a stem region, only if the captor molecule has hybridized with a target nucleic acid. In an aspect, the labeled probe is bound to a label that is detectable by external detection methods.

In an aspect, in addition to the nucleic acid loop segment, a captor molecule comprises two stem regions, a 5' stem region and a 3' stem region, that are complementary to one another and generally, one stem region is attached to one end of the loop sequence, so that a capture molecule comprises, in order from 5' to 3', a stem region-a loop region-a stem region. Stem-loop structures are known to those of skill in the art. The two stem regions can hybridize to form a stem, thereby forming the captor molecule into a hairpin shape. In an aspect, a captor molecule is attached to a substrate by a connector molecule that is connected to a first stem region at the first stem region's end that is not connected to the loop section. In an aspect, a captor molecule's second stem region (that is not bound to a connector molecule) comprises a region having a nucleic acid sequence that is complementary to a labeled probe. In an aspect, a capture molecule comprises a nucleic acid structure that has regions, for example, in a 5' to 3' direction comprising a connector molecule-a first stem region-a loop region-a second stem region having sequences complementary to a labeled probe.

In an aspect, a general negative control captor molecule is a captor molecule with a loop region sequence that is not complementary to any known naturally occurring target nucleic acid, for example, SEQ ID NO. 160. As can be understood, in particular assays, the sequence of a general negative control captor molecule may be designed to not bind with the anticipated target nucleic acids of a particular assay. A negative control captor molecule will not bind with target molecules in the assay, thus a labeled probe will not specifically bind to a stem region of a captor molecule. The negative control captor molecule serves to show that the random binding by the target molecules is not occurring. A general negative control captor molecule also serves as a positive control, in an assay and across a series of assays, as measure of background random binding of a labeled probe. As no target molecule binds to the general negative control captor molecule, any label detected, for example at the location of the bound general negative control captor molecules, is background, low level, binding by a labeled probe. This low level background detected label serves as a control point within the assay so that this indiscriminant amount of label can be differentiated from the label amounts seen for specific binding, and also if no label is seen, that the assay may not be functioning as required. Further, the general negative control captor molecule serves as a control for specificity and accuracy across assays performed, for a uniform reaction measure of the assays. For example, a series of assays, each using the same general negative control capture molecule, should report a similar level of nonspecific binding for the general negative control capture molecule, thus assuring repeatable and reliable measurements for the assays.

In an aspect, there is a specific negative control captor molecule for each type of captor molecule, in that the negative control does not bind the target molecule. For example, see SEQ ID NO. 167 and 168. A specific negative control captor molecule has the same thermodynamic characteristics as does its captor molecule (for which the specific negative control captor molecule is the negative control), but the negative control captor molecule does not bind or hybridize with the target nucleic acid sequences. Thus, when the target sequences are present, the negative captor molecule is not bound by a labeled probe.

By "a type of captor molecule" it is intended that a plurality of a type of captor molecules has the same, as in identical, nucleic acid sequence in the target binding sequence (in the loop section of the captor molecule) as every other captor molecule of that type. As used herein, related types of captor molecules means that the captor molecules of the related types do not have an identical target binding nucleic acid sequence, but the captor molecules are related in that the types may bind to differing sequences of target sequences from the same pathogen or organism, or may bind to differing sequences of differing pathogens or organisms that are related. For example, a set of three types of related captor molecules may bind to a particular pathogen's target sequence such that the first type of related captor molecule (target sequence binding sequence in the captor molecule loop) binds closer to the 5' end of a target sequence, the third type of related captor molecule (target sequence binding sequence in the captor molecule loop) binds closer to the 3' end of a target sequence, and the second type of related captor molecule (target sequence binding sequence in the captor molecule loop) binds between the first and third related types. Alternatively, a set of three related captor molecules may each bind to the same pathogen, but each one binds to a different subtype or strain of the pathogen.

In an aspect, a captor molecule can be labeled. For example, a captor molecule may have two fluorescent or chromophore molecules that function as a pair, with one being the fluor, and the other molecule the quencher. This pair is used in fluorescence resonance energy transfer (FRET), a mechanism describing energy transfer between two light-sensitive molecules (chromophores) A donor chromophore, the fluor, initially in its electronic excited state, may transfer energy to an acceptor chromophore, the quencher. The efficiency of this energy transfer is inversely proportional to the sixth power of the distance between donor and acceptor, making FRET extremely sensitive to small changes in distance. Measurements of FRET efficiency can be used to determine if two fluorophores are within a certain distance of each other. The measurement of the presence of the excited fluor molecule indicates that the quencher molecule is sufficiently far away so that the quencher cannot absorb the transferred energy.

In an aspect a labeled captor molecule comprises a FRET pair, wherein a fluor is attached to one stem sequence and the quencher molecule is attached to the complementary stem sequence. When the stem sequences are bound to each other, the fluor is in close proximity to the quencher molecule, and no fluorescence is detected. When the captor molecule binds a target nucleic acid, the stem sequences are separated from each other and the fluorescence of the fluor can be detected because the quencher molecule is no longer in close proximity. This can be referred to as the captor molecule being in an open conformation. In an aspect, a detection enhancer molecule or labeled detector molecule can be added to the captor molecule in an open conformation. With such a detection enhancement molecule bound to the captor molecule, the fluorescence of the fluor can be detected more easily or at a lower level.

In an aspect, in order to function as a rapid assay, captors can be designed so that the stability of the closed hairpin structure is balanced with that of the target-captor duplex. In an aspect, individual captors are spaced apart from one other by at least half of the length of the closed hairpin of a captor molecule. Though not wishing to be bound by any particular theory, it is theorized that such spacing allows each captor to act independently of its neighbors and prevent the formation of captor dimers (as shown in FIG. 3(C)).

Figure 1B:
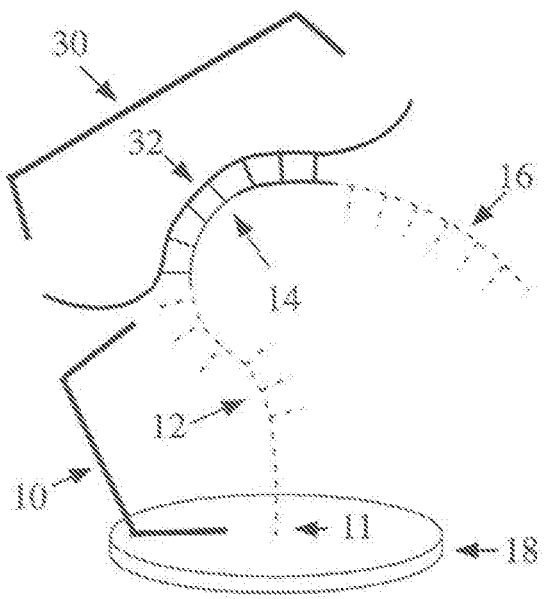
FIG. 1(B) is a representative schematic showing a stem loop captor molecule interacting with a target nucleic acid to form a target-captor molecule duplex, which causes a stem-loop captor molecule to change into an open conformation, according to various aspects of the present disclosure.
Figure 1C:
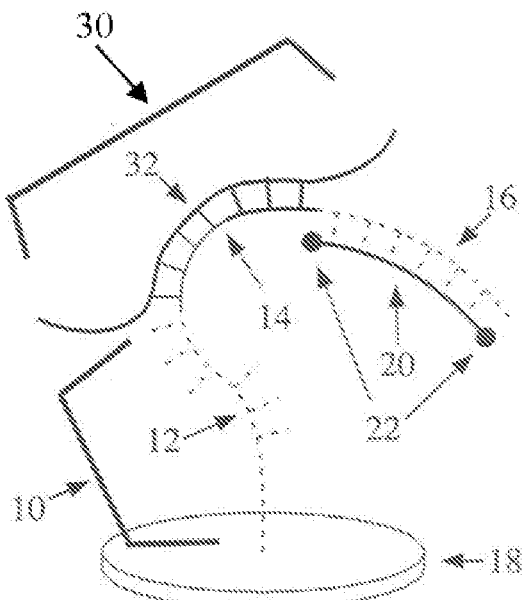
FIG. 1(C) is a representative schematic showing an open stem loop captor molecule with a bound target nucleic acid interacting with a labeled probe to form a nucleic acid detector, according to various aspects of the present disclosure.

In an aspect, referring generally to FIGS. 1A-1D, a nucleic acid detector and method comprise captor molecule 10 and labeled probe 20 to determine the presence of target nucleic acid 30 within a sample. As shown in FIG. 1A, captor molecule 10 can be attached to substrate 18 through linker 11 and can have first stem region 12, loop region 14, and second stem region 16. As shown in FIG. 1C, labeled probe 20 can be labeled with one or more labels 22. As shown in FIG. 1C, target nucleic acid 30 can have complementary region 32 to loop region 14 of captor molecule 10.

In an aspect, as shown in FIG. 1A, captor molecule 10 can form a stem-loop structure when the terminus of one of its stem regions is bound to substrate 18. Captor molecule 10 is comprised of three major regions, first stem region 12, loop region 14, and second stem region 16.

Figure 1D:
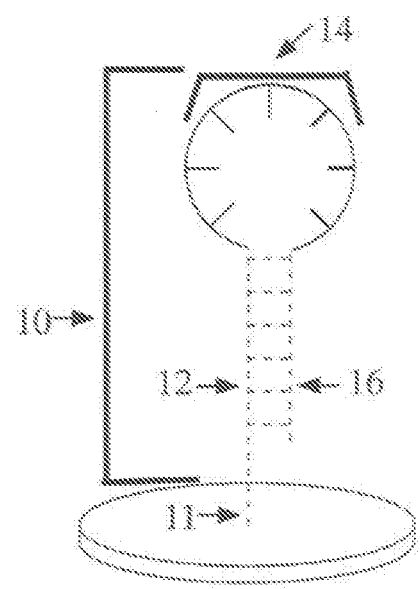
FIG. 1(D) is a representative schematic showing a closed stem loop captor molecule in the absence of a target nucleic acid, according to various aspects of the present disclosure.
Figure 2:
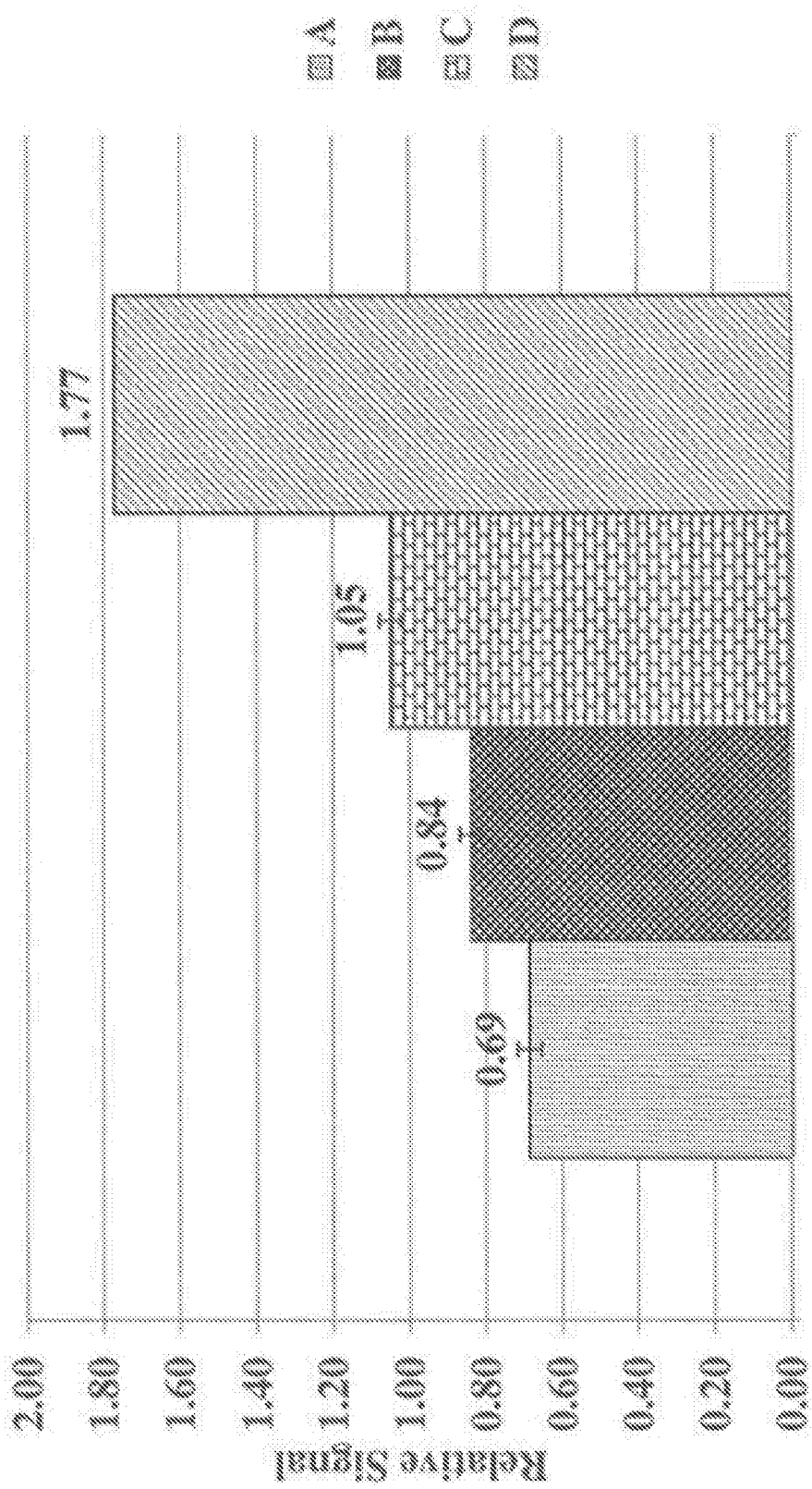
FIG. 2 is a representative graph of data showing that the relative signal from uropathogenic *Escherichia coli* total RNA increases with increasing micrograms (μg) of total RNA, from 0 μg to 246 μg as indicated (concentrations of total RNA are as follows: A: 0 μg RNA, B: 50 μg RNA, C: 133 μg RNA to D: 246 μg RNA), according to various aspects of the present disclosure.

In an aspect, as shown in FIG. 1B, if target nucleic acid 30 is present within a sample, target nucleic acid 30 hybridizes with loop region 14 of captor molecule 10. Target nucleic acid 30 hybridizes with loop region 14 of captor 10 if target nucleic acid 30 contains a nucleic acid sequence in complementary region 32 that is complementary to a sequence found within loop region 14 of captor molecule 10. When captor molecule 10 binds to target nucleic acid 30, then captor molecule 10 changes into its open conformation and is no longer in a closed stem-loop (hairpin) conformation. As shown in FIG. 1D, captor molecule 10 that has not bound to its target nucleic acid remains in the closed stem-loop conformation. As shown in FIG. 1C, the binding of complementary region 32 of the target nucleic acid 30 to a complementary sequence in loop region 14 of captor molecule 10 opens the stem region and labeled probe 20 binds to stem region 16 of the captor molecule 10. The binding portion of stem region 16 is exposed and capable of binding labeled probe 20 when target nucleic acid 30 binds to captor molecule 10.

In an aspect, using specific assay conditions, a portion of the nucleic acid sequence in loop region 14 in captor molecule 10 binds specifically to a portion of the nucleic acid sequence of target nucleic acid 30 wherein the complementarity of the sequence of complementary region 32 and the sequence of loop region 14 is 100%, and there is no binding of target nucleic acid 30 to nucleic acids that do not have 100% sequence complementarity. In an aspect, captor molecule 10 can distinguish single-nucleotide polymorphisms (SNPs) in target nucleic acid 30. In an aspect, it was discovered that in order to achieve SNP discrimination, captor molecule 10 can be contacted with target nucleic acid 30 under conditions below the melting point of the stem-loop hairpin structure of captor molecule 10 and below the melting temperature of the target-captor duplex. In an aspect, maintaining the stem-loop structure of the captor during the first hybridization step causes the replacement of the stem-loop structure of the captor with the target-captor duplex. The exchange in structured forms (from stem regions binding to binding of target sequence and loop sequence) increases the specificity of captor molecule 10 for its fully (100%) complementary target nucleic acid thereby ensuring SNP discrimination.

In an aspect, a portion of the nucleic acid sequence of loop region 14 in captor molecule 10 binds specifically to a portion of the nucleic acid sequence of complementary region 32 of target nucleic acid 30 wherein the complementarity of the sequence of complementary region 32 and the sequence of loop region 14 is 50-99%, or 50% to 100%, or 50%, or 55%, or 60%, or 65%, or 70%, or 75%, or 80%, or 85%, or 86%, or 87%, or 88%, or 89% or 90%, or 91%, or 92%, or 93%, or 94%, or 95%, or 96%, or 97%, or 98%, or 99%, or 100%, and percentages thereinbetween.

In an aspect, it was unexpectedly found that it was possible to shorten the time required to perform methods disclosed herein by using conditions comprising a buffer in the initial hybridization step of the target sequence with the loop sequence that interferes with the formation of stable nucleic acid duplexes. This result was unexpected at least because the ability of the buffer to interfere with duplex formation was not expected to allow a reduced time, but rather it was expected that a longer time would be required. In an aspect, it was unexpectedly found that it was possible to increase the signal produced from a specific amount of target by the stem-loop captor method by introducing a buffer that interferes with the formation of stable nucleic acid duplexes. This result was unexpected at least because the ability of the buffer to interfere with duplex formation was not expected to allow increased signal, but rather it was expected that a lower signal would be seen. In an aspect, such buffers allow the target nucleic acid and the captor to sample prospective binding partners rapidly and favors the establishment of stable target-captor duplexes preferentially only if the sequences are fully complementary thus also contributing to the specificity of binding. In an aspect, the selection of the appropriate buffer allows binding to occur in as little as ten (10) minutes.

In an aspect, buffers containing non-ionic surfactants required longer times for duplex formation and made the methods disclosed herein less functional. For example, fewer target molecules bound to the captors in the same amount of time, or more time was needed to bind the same amount of target molecules to the captors.

Particular buffers were found to shorten the time needed for detection of captor molecules bound with a labeled probe and to increase specificity and reproducibility of assays, particularly buffers used in an hybridization step, for example, where the target sequence binds to the complementary loop sequence, and/or where the probe binds to the stem region of the captor molecule. In an aspect, buffers containing ionic surfactants, such as sodium dodecyl sulfate (SDS) at concentrations from 0.005% to 0.2% v/v required shorter times for duplex formation. In an aspect, buffers including ethanol at concentrations from 5% v/v to 30% v/v, or dimethyl sulfoxide (DMSO) at concentrations from 0.10 M to 1.0 M, required shorter times for duplex formation. In an aspect, the first incubation buffer required approximately 10 minutes for duplex formation. Buffers for more rapid detection of captor molecules bound with a labeled probe include, but are not limited to, buffers comprising ionic surfactants, buffer comprising sodium dodecyl sulfate at concentrations from 0.005% to 0.2% v/v; buffers comprising ethanol at concentrations from 5% v/v to 30% v/v; buffers comprising dimethyl sulfoxide (DMSO) at concentrations from 0.10 M to 1.0 M; and combinations thereof.

Figure 14:
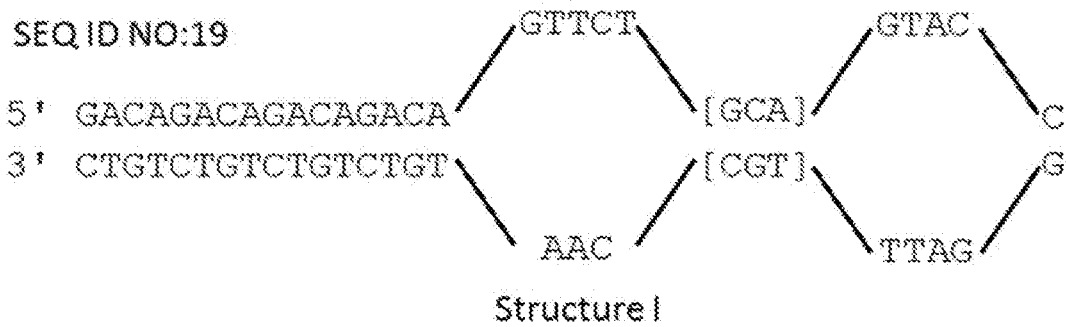
FIG. 14 shows a representative self-complementary double-stranded captor molecule, designated Structure (I).

In an aspect, structural parameters for captor molecule 10 that contribute to rapid and specific SNP discrimination have been determined. Over 50 experimental combinations of loop sequences with similar stem sequences have been studied. In an aspect, a captor molecule 10 that has some portion of loop region 14, with a lower limit of 2 nucleotides in length, that can form a self-complementary double-stranded structure within loop region 14, forms stable stem-loop structures at approximately room temperature (approximately 23° C. or 74° F.). Approximately in this range means plus or minus 5° C. In an aspect, the SamecA1 captor molecule exhibited low background binding of the labeled probe at room temperature. The SamecA1 captor molecule (SEQ ID NO: 19), sequence shown in Table I, is predicted to have a folded structure as shown in FIG. 14 where the 16 base pairs on the 5' left of FIG. 14 form the stem region and the remaining nucleotides form the loop region of this captor. The nucleotides in the brackets are loop sequences that can form a self-complementary double-stranded structure (I) shown in FIG. 14.

Figure 15:
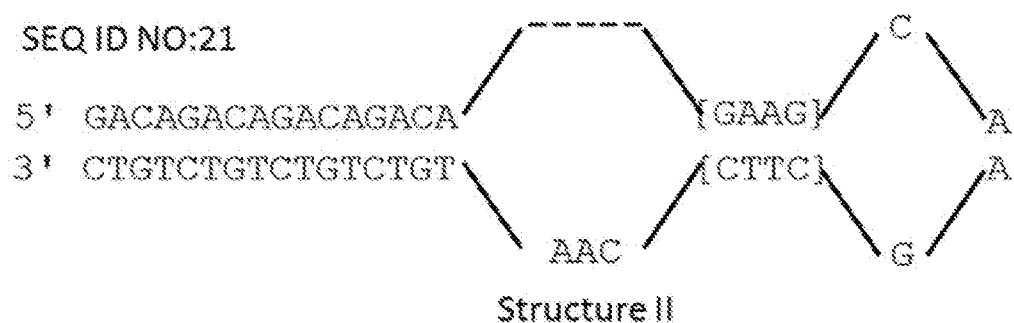
FIG. 15 shows a representative self-complementary double-stranded captor molecule, designated Structure (II).
Figure 16:
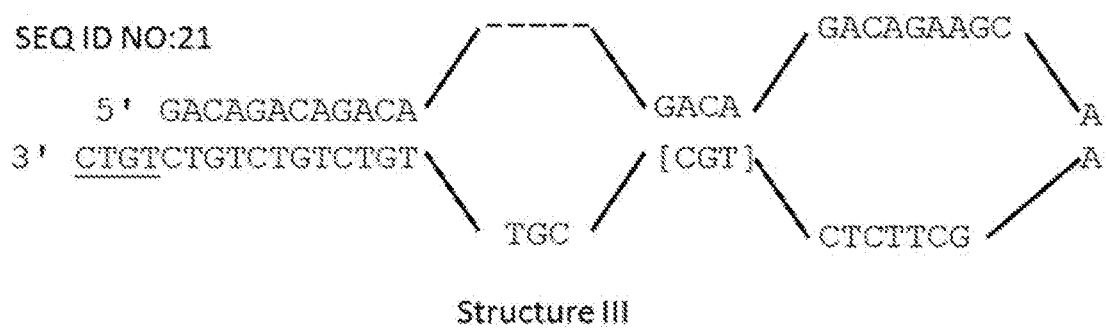
FIG. 16 shows a representative self-complementary double-stranded captor molecule, designated Structure (III).

In contrast, it was discovered that some captors with this self-complementary double-stranded structure within the loop show high non-specific binding to the labeled probe due to alternating structures formed by the captor that allow for free ends in the stem region to be bound by a labeled probe, even when no target sequences are bound. It was discovered that such captors were able to misfold and leave dangling ends to which the labeled probe can bind in the absence of target nucleic acid. For example, the captor Sau71 (SEQ ID NO:21), sequence listed in Table I, is predicted to have a folded structure where the nucleotides in the brackets are loop sequences that can form a self-complementary double-stranded structure (II) shown in FIG. 15, but also the structure shown in FIG. 16. Underlined sequences in FIG. 16 show the sequence capable of non-specifically binding a complementary labeled probe in the absence of target sequences bound to the loop region.

In an aspect, the nucleotides in captor molecule 10 can be chosen from the set of Watson-Crick nucleic acids, locked nucleic acids or peptide nucleic acids. In an aspect, the stems of the captor molecules can be designed to contain two LNA C nucleotides (denoted +C). For example, a such as captor Pos1-C2 (SEQ ID NO:3) can be designed to contain two LNA C nucleotides (denoted +C).

In an aspect, first stem region 12 contains one or more complementary sequences which can form a double-stranded stem region with second stem region 16 thereby forming a stem-loop structure in the general shape of a hairpin. The end of first stem region 12 that is away from or distal from loop region 14 can be considered the site of attachment to substrate 18 and can be the 5' or 3' end of captor molecule 10. In an aspect, first stem region 12 and second stem region 16 are generally between approximately 8 and approximately 20 nucleotides in length. In this range approximately means plus or minus twenty percent (20%). In an aspect, first stem region 12 and second stem region 16 do not have to be the same length or number of nucleotides. In an aspect, if first stem region 12 and second stem region 16 are not the same length or number of nucleotides, an overhang of one or more single-stranded nucleotides can be created on the end away from the loop. In an aspect, such overhangs can be utilized to either stabilize or destabilize the stem-loop structure of captor molecule 10.

In an aspect, loop region 14 comprises a sequence that is complementary to target nucleic acid 30. In an aspect, the region in captor molecule 10 that is complementary to target nucleic acid 30 can extend beyond loop region 14 into first stem region 12 or second stem region 16, or both, which provides a longer target-binding region without increasing the length of loop region 14, thus increasing the specificity of captor molecule 10 for its target nucleic acid 30.

In an aspect, a method, system or device can comprise several types of captors in which each type of captor molecules comprises a plurality of captor molecules such that each type of captor molecules has a loop region sequence that is complementary to a target nucleic acid that is different from the loop region sequence complementary to a target nucleic acid of another captor molecule. In an aspect, each type of captor molecules can be applied and bound to its own geographic location on a substrate, such as on a microarray. The method of detection can be performed on the one or more types of captors to detect multiple target nucleic acids in the same sample. Each captor in the one or more types of captors can have an identical portion in the sequence of second stem region 16 of captor molecule 10, which portion is only exposed upon the binding of target nucleic acid 30 to the captor and which portion is complementary to labeled probe 20. In this way, one labeled probe, having a sequence that is complementary to each of the captor molecules can be used, e.g., a universal detector or probe.

In an aspect, a method comprising captor molecules was carried out using a labeled probe that was the same length as the second stem region to which it was complementary. However, it was discovered, that in some instances, a labeled probe the same length as the stem can bind to the captor even in the absence of the target nucleic acid. Though not wishing to be bound by any particular theory, it is believed that the energetics of the first stem region binding to the second stem region were nearly the same as the binding of the second stem region to the labeled probe. It was proposed that if the binding energy of the labeled probe for its binding site on the captor is equal to or higher than the binding energy of the first stem region for the second stem region, then the labeled probe can bind to the captor in the absence of the target nucleic acid. Further, it was recognized that the labeled probe can be modified to decrease its binding energy to the second stem region by altering its length or label so that it can preferentially only bind to the captor whose second stem region is already exposed due to the binding of the target nucleic acid. It has been found that for methods disclosed herein that the complementary regions in the probe and stem regions be thermodynamically less stable than the thermodynamic stability of the two stem regions to each other. One aspect of this stability is that the number of sequences of the probe that are complementary to sequences of a stem region are less than the number of complementary sequences of the stem region, regardless of the overall length of the probe or the length of the stem region.

In an aspect, a labeled 13-nucleotide nucleic acid probe, and a captor with a first stem region and second stem region of sixteen complementary nucleotides that is complementary to the 13-nucleotide probe, results in the labeled 13-nucleotide probe not binding efficiently to the captor molecule's stem region in the absence of the captor's complementary target nucleic acid, but instead binds rapidly to the stem region of the captor that has bound its target nucleic acid. In an aspect, disclosed herein are captor molecules having stem regions that are complementary to a labeled probe, but that comprise 1-6 more nucleotides, or one more nucleotide, or two more nucleotides, or three more nucleotides, or four more nucleotides, or five more nucleotides, or six more nucleotides, or more nucleotides than does the probe molecule. For example, a stem region of a captor molecule may comprise 15 nucleotide-length stem regions and a 12-nucleotide length probe that is complementary to a portion of a stem region. The probe may or may not be labeled, depending on the assay, and location of one or more labels, e.g., on the captor or the probe, may be determined by one of skill in the art.

In an aspect, stem regions of a captor molecule may each comprise a nucleic acid comprising from about 10 to about 20 nucleotides. In an aspect, a probe molecule disclosed herein may comprise a nucleic acid polymer comprising from about 8 to about 18 nucleotides. In an aspect, a probe molecule may be longer than or shorter than, i.e., comprise more or fewer nucleotides, than a stem region of a captor molecule. Stem regions may have fewer than 10 nucleotides and may have more than 20 nucleotides, and design of stem regions is within the skill of those in the art.

In an aspect, a detectable label is a fluorescent label. In an aspect, a label can be selected based on the degree of hydrophobicity and the charge on the fluorescent moieties in order to inhibit non-specific complexes. In an aspect, a label does not have a net positive charge. In an aspect, a label does not have a net +1, +2, or +3 charge. In an aspect, a label has a net negative charge. In an aspect, a label has a net −1, −2, or −3 charge. In an aspect, a label has less than or about the same hydrophobicity as Alexa 647. Without wishing to be bound by a particular theory, it is believed that a net positively charged label with greater than or about the same hydrophobicity as Alexa 647 can approach the negatively charged nucleic acid captors along the hydrophobic substrate that the captors were bound upon and thus bind to all captors even in the absence of target nucleic acid binding.

In an aspect, a disclosed label is Alexa 647 (Alexa Fluor® 647, Invitrogen, Thermo Fischer Scientific Inc., Waltham, Mass.). In an aspect, the label is Alexa 647. In an aspect, the label is the fluorescent molecule ATTO 647N (Sigma Aldrich, St. Louis, Mo.). In an aspect, the label is ATTO 647N. In an aspect, the label is not ATTO 647N. In an aspect, the label can be selected based on the degree of hydrophobicity and the charge on the fluorescent moieties in order to inhibit non-specific complexes.

In an aspect, one result of shortening the length of the labeled probe to less than the full length of the first stem region and second stem region is that it frees the nucleotides at the ends of the stems near the loop to no longer be constrained to be part of the universal labeled probe binding sequence, which means those sequences can become part of the target-binding sequence. The captor can then be designed to have the target nucleic acid bind into the first stem region or the second stem region, or both, making longer complementary target binding sequences with the same size loops.

In an aspect, the captor is Ec632 (SEQ ID NO:1) having the sequence listed in Table I. In an aspect, the target-binding region is the entire bracketed region of Structure (IV) as shown in FIG. 17. However, the underlined region in Structure (IV) is the sequence of this captor that forms the loop region. The target nucleic acid for this captor Ec632S (SEQ ID NO:23), whose sequence is listed in Table I, binds one nucleotide into the first stem region. By targeting a sequence that has homology into the stem region, the net binding strength of this captor can be increased.

In a further aspect of the present invention, the sequence of the stem adjacent to the loop can also be changed to facilitate increased strength of target binding. In an aspect, the captor is CHIKV-1 (SEQ ID NO:25) having the sequence listed in Table I. In an aspect, the loop region is the underlined region of Structure (V) as shown in FIG. 18.

The bracketed nucleotides adjacent to the loop have been changed from the usual stem sequences to allow the target for this captor, CV1S (SEQ ID NO:26), sequence listed in Table I, to bind to the C nucleotide on the 5' side of the loop. Though not wishing to be bound by any particular theory, it is thought that longer complementary sequences, without the requirement for larger loops, allows a captor to have a more uniform melting temperature.

In an aspect, the spacing of the captors on a substrate may affect the sensitivity of a method comprising captors in a rapid assay, wherein a rapid assay using methods disclosed herein can be performed in from about 0.2 hour to about 2 hours. This was an unexpected result that was not seen in a longer term assay, such as a 12-hour assay that did not use parameters disclosed herein for rapid methods, including but not limited to, probes with complementary sequences that are fewer than those of a stem region, spaced-apart captor molecules, somewhat denaturing hybridization buffers, and lower temperatures used to interrupt initial binding of captors to allow for hybridization with target molecules.

A substrate can include a microarray slide, a microbead, a fiber optic cable, the surface of a microtiter plate, an electrically conducting surface such as a wire, or other surfaces. When the plurality of captor molecules are printed onto (attached to) microarray slides at recommended nucleic acid concentrations, typically $2\times10^1$ µM, the labeled probe binds to the captor during the rapid assay even in the absence of the target nucleic acid. Diluting the captor, before printing (attachment of the captors), to levels of approximately $1\times10^{-1}$ µM to $1\times10^1$ µM results in specific binding of the labeled probe to the captor only in the presence of the target nucleic acid.

Figure 3A:
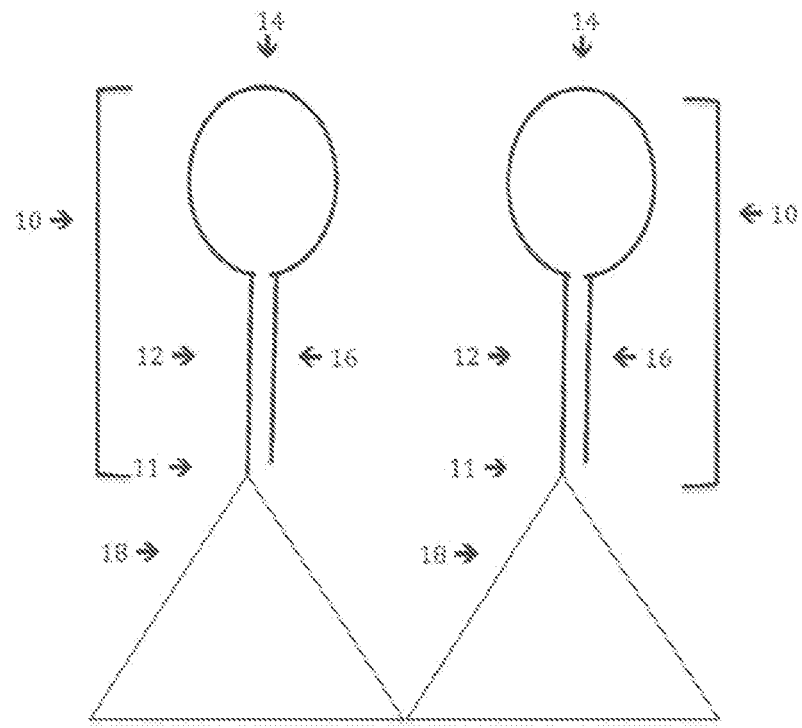
FIG. 3(A) is a representative schematic showing a possible spacing of two captor molecules on a substrate, according to various aspects of the present disclosure.
Figure 3B:
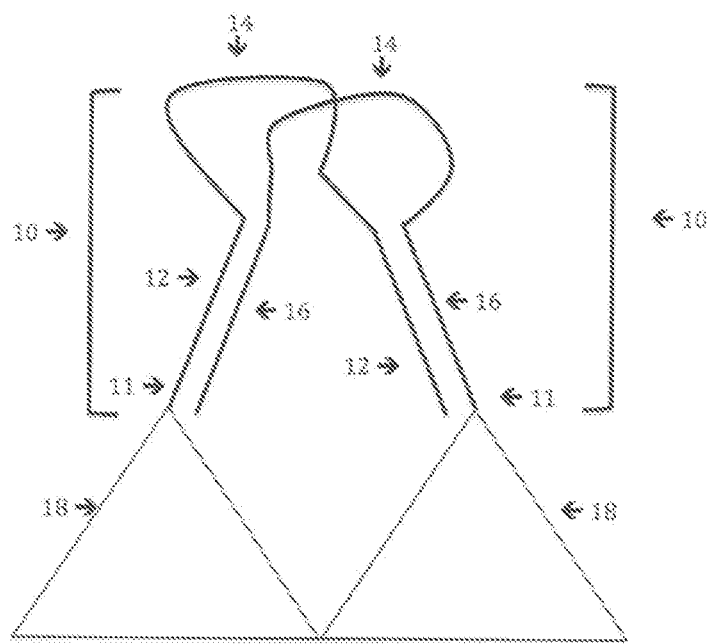
FIG. 3(B) is a representative schematic showing a possible formation of captor molecule-dimers between two neighboring captor molecules on a substrate, according to various aspects of the present disclosure.
Figure 3C:
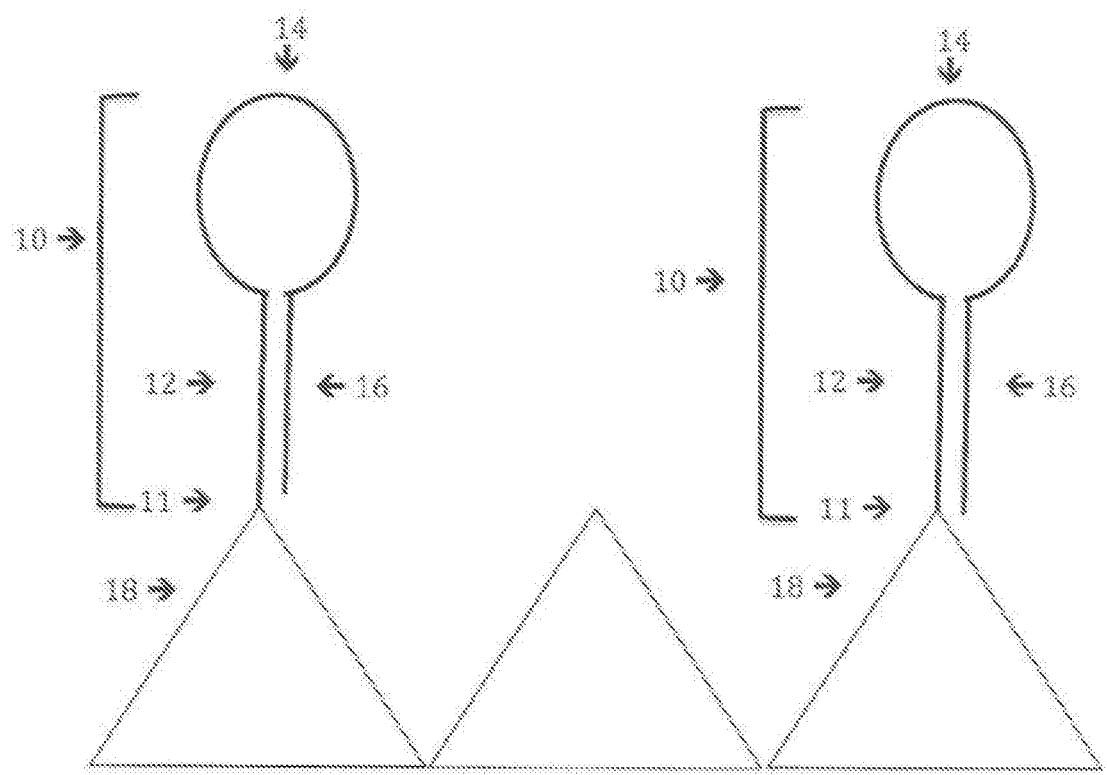
FIG. 3(C) is a representative schematic showing that increasing the spacing between two neighboring captor molecules on a substrate may prevent the possible formation of captor molecule-dimers, according to various aspects of the present disclosure.

In an aspect, if captors are bound to a substrate at a distance of less than half the length of the average closed captor molecule as in FIG. 3(A), a captor-dimer complex is postulated to form as in FIG. 3(B) where the first stem region of the captor on the left can bind to the second stem region of the captor on the right, and the first stem region of the captor on the right can bind to the second stem region of the captor on the left, leaving the two loop regions 14 to bridge the distance between the pair of misfolded stems. In an aspect, transitioning in and out of such misfolded states can allow the captors to spend less time in the correct stem-loop conformation and thus make the non-specific binding of labeled probe in the absence of target more likely to occur. Spacing the captors further apart, as shown in FIG. 3(C), lowers the non-specific binding of labeled probe in the absence of target by preventing neighboring captor stem regions from interacting.

In an aspect, if the captor is at least half of the average length of the structure of a closed stem-loop captor away from the next neighboring captor, then captors are unable to form the captor dimer complex. For captors totaling 50 to 60 nucleotides, the length of the hairpin structure is approximately $4\times10^{-1}$ nm, where approximately means plus or minus thirty percent (30%) in this range.

In an aspect, the desired spacing of the captors on the substrate can be achieved by 1) diluting the concentration of captor molecules provided to a substrate so that the captor molecules fill only a portion of the available binding sites on the substrate, 2) by providing binding sites on the substrate that are spaced apart at least half of the length of the structure of a closed stem-loop captor, or 3) by adding a competitor for binding to the available sites on the substrate. Competitive binding inhibitors can be nucleic acids, small organic molecules, nanoparticles or other moieties capable of binding to the surface of the substrate. An effective competitor is a 10 nucleotide polyA DNA attached to the same chemical linker as the captor, see SEQ ID NO: 30.

In an aspect, the present disclosure pertains to competitive binding inhibitors that can be used in the disclosed methods. For example, a disclosed method can further comprise a step of providing competitive inhibitors to a composition of captor molecules or providing competitive inhibitors in a step of a method disclosed herein. Disclosed competitive inhibitors can aid in preventing random binding events. A disclosed competitive inhibitor can be a small amine compound such as tert-butylamine or diethylamine, or other amine-functionalized binding competitors.

In an aspect, a disclosed competitive inhibitor can be a peptide nucleic acid competitive inhibitor that is comprised of a linker portion and a peptide nucleic acid portion. In an aspect, a linker is a six carbon sequence polymer and an amino group can be used to attach one end of the linker to a substrate and the other end of the carbon sequence polymer can be attached to another molecule, for example, a captor molecule or a competitive inhibitor. In an aspect, a peptide nucleic acid of the disclosure can be of a length that is substantially the length of the stem portion of a captor molecule. In an aspect, a competitive inhibitor mimics a linker (the component that is covalently bound to one end of the captor molecule to anchor the captor molecule to a substrate surface) and the stem region of a captor molecule. For example, a captor molecule can be attached to a surface by an amino group on the end carbon of a $C_6$ molecule covalently attached to the 5' end of the first stem sequence of a captor molecule. In an aspect, a peptide nucleic acid competitive inhibitor may comprise an amino group on the end carbon of a $C_6$ molecule covalently bound to a sequence of peptide nucleic acid bases such that the peptide nucleic acid competitive inhibitor has the length of the amino-$C_6$ molecule+the first stem sequence nucleic acids. The nucleic acid portion of a peptide nucleic acid competitive inhibitor can be from 5 to 15 nucleic acids or longer. In an aspect, the nucleic acid portion comprises only nucleic acid bases. In an aspect, the nucleic acids portion comprises nucleic acid bases and other components such as components that aid in the hydrophilicity or hydrophobicity of the peptide nucleic acid competitive inhibitor. For example, a nucleic acid portion may comprise nucleic acid bases covalently linked in a sequence in which glyceryl-O-linkers are interspersed. For example, a peptide nucleic acid competitive inhibitor may comprise a linker portion covalently linked to a nucleic acid portion that comprises 5' A-A-(glycery-O-linker)-A-A-A--(glycery-O-linker)-A-A-A 3'. Other nucleic acid bases (CTGU) are contemplated as are other linker groups, and other arrangements of such polymers. For example, a peptide nucleic acid competitive inhibitor may comprise a linker portion covalently linked to a nucleic acid portion that comprises 5' U-A-(glycery-O-linker)-A-U-A--(glycery-O-linker)-A-U 3'.

A linker portion of a peptide nucleic acid competitive inhibitor may comprise any linker. For example, the linker portion can be a $C_6$ molecule. In an aspect, the linker portion can be a $C_{12}$ molecule. Linker portions and nucleic acid portions can be combined in a wide variety of components to make a peptide nucleic acid competitive inhibitor that has the desired length of the stem portion and its linker of the captor molecule. Alternatively, a peptide nucleic acid competitive inhibitor can be longer or shorter than this length.

Compositions disclosed herein may comprise helper oligos that are small nucleic acid polymers that bind to the target nucleic acids. In an aspect, a target nucleic acid can be bound by a nucleic acid termed a "helper oligo" that has a sequence that is complementary to a region of the target nucleic acid outside the target nucleic acid sequence that is complementary to the sequence found within the loop region of captor molecule. The helper oligo can bind to the target nucleic acid on the 5' side or the 3' side of the target nucleic acid sequence that is complementary to the captor loop region. Helper oligos can have a length between 10 and 40 nucleotides and can be complementary to a region of the target nucleic acid that is at least 3 nucleotides 5' of the 5' end of the captor binding sequence of the target nucleic acid or at least 3 nucleotides 3' of the 3' end of the captor binding sequence of the target nucleic acid. One or more helper oligos can bind to a target nucleic acid before or during the binding of the target nucleic acid to the captor loop region. Without wishing to be bound by a particular theory, it is believed that the binding of a helper oligo to the target nucleic acid would unfold potential secondary structure in the target nucleic acid around the captor binding sequence thus freeing the captor binding sequence of the target nucleic acid to be more available to bind to the captor loop region.

Methods

Antibiotic Sensitivity Screening

In an aspect, exposure of organisms or cells to compounds such as drugs or antibiotics prior to assaying the organisms or cells using a stem loop captor method, system or device can be used to rapidly determine whether the organism or cells responds to the compound by changing the levels of target nucleic acids.

In an aspect, methods of detection disclosed herein can be performed on an agent after the agent has been exposed to a compound, such as a cancer drug or antibiotic, to determine if exposure to the compound has changed the levels of target nucleic acids in the agent. Captor molecules can be designed that hybridize to target nucleic acids that may change in presence or quantity in response to the agent being exposed to the compound. After exposure of the agent to the compound, for instance incubating a sample that can contain bacteria with an antibiotic for 30 minutes at 37 degrees Celsius, the nucleic acids can be processed and used in disclosed methods for detecting target nucleic acids. Analysis of the presence of or changes in the abundance of target nucleic acids can be used to determine if the agent in the sample responded to the compound. A method of the present disclosure comprises detecting target nucleic acids from one or more agents using captor molecules in methods disclosed herein, wherein before detecting the target nucleic acids, the one or more agents were exposed to conditions, such as therapeutic or chemotherapeutic compounds or molecules, that caused the agents to respond by synthesizing one or more target nucleic acids or by altering the amount of target nucleic acids synthesized by the agent.

The present disclosure comprises methods for rapidly and sensitively detecting the presence of one or more target nucleic acid sequences within an environmental or biological sample, using a captor molecule and a labeled probe, both of which are comprised of nucleic acids.

In an aspect, disclosed methods comprise detecting target nucleic acid sequences by hybridizing the target nucleic acids to a captor molecule without the need for melting the captor molecule nucleic acids using high heat conditions such as 65° C., and subsequently hybridizing a probe, such as a labeled (detectable) probe to the target-captor molecule.

In an aspect, disclosed methods provide for reliable detection of target nucleic acid sequences within a biological sample without the need to amplify the target nucleic acid prior to or during detection.

In an aspect, disclosed methods can sensitively and accurately detect a target nucleic acid. For example, disclosed methods can detect and discriminate target nucleic acid sequences that differ by as little as one nucleotide, such as SNP detection. Disclosed methods detect a labeled probe that has bound to a captor molecule if the captor molecule has bound a target nucleic acid sequence, which provides an improved selectivity, specificity and ability to detect one or more (different) target nucleic acids. Accordingly, disclosed methods provide for reliable detection of specific nucleic acid sequences in a sample with minimal concern for inaccuracies due to background noise, selection, and specificity.

In an aspect, disclosed methods can be used to simultaneously detect the presence of multiple target nucleic acids within a sample, e.g., an environmental or a biological sample. In an aspect, disclosed methods can be used to determine susceptibility of one or more agents present in a sample to therapeutic or other compounds or molecules. In an aspect, the disclosed methods can be used to determine the gene expression or an alteration in the synthesis of nucleic acids of one or more agents present in a sample.

In an aspect, disclosed methods utilize a substrate-bound stem-loop captor molecule that works in conjunction with a probe, which can be a labeled probe to detect target nucleic acids of an agent, thus indicating the presence of an agent within a sample. In an aspect, disclosed methods provide ease in detection of multiple target nucleic acids when the captors are attached as separate clusters upon the surface of a common substrate therefore allowing the simultaneous detection of multiple target nucleic acids within a common sample.

In an aspect, if a target nucleic acid is present within a sample, the target nucleic acid hybridizes with the loop sequence of a captor molecule (as shown in FIG. 1(B)). The target nucleic acid only hybridizes with the loop region of the captor molecule if the target nucleic acid contains a sequence that is complementary to a sequence found within the loop of the captor molecule. When the captor molecule binds to the target nucleic acid, then the closed stem of the captor molecule opens. Captor molecules that have not bound target nucleic acids remain in the closed stem-loop conformation (as shown in FIG. 1(D)).

In an aspect, after exposure to a sample containing a possible target nucleic acid, the captor molecule is exposed to a labeled probe. As discussed previously, the detectable aspect or moiety may be found on the probe or on the captor molecule. For ease of discussion, a labeled probe may be referred to herein, wherein it is contemplated that the label may be located on the probe, the captor molecule or both. The terms "detectable" and "labeled" are used interchangeably herein, for example, a detectable or labeled probe refers to a nucleic acid sequence having an aspect that is detectable by a device so as to indicate the presence of the nucleic acid. The label can be a moiety bound to the nucleic acid, such as a fluor molecule, or the nucleotides themselves in the nucleic acid polymer may be detectable, such as radiolabeled nucleotides. The sequence of the labeled probe is complementary to a region of the stem region of the captor molecule and as a consequence can bind to that stem region if the captor molecule is in the open conformation. If a target nucleic acid has hybridized with the captor molecule, the captor molecule can have an open conformation and the unbound stem region of the captor molecule can be free to hybridize with the labeled probe (as shown in FIG. 1(C)). If no target nucleic acid has hybridized to the captor molecule and the captor molecule remains in the closed stem-loop confirmation, then the labeled probe is unable to bind to the closed hairpin (as shown in FIG. 1(D)) and can be washed away in a rinse step.

In an aspect, disclosed methods provide for detection of target nucleic acids with less interference from background noise because labeled probes are washed from the captors when no target nucleic acids are present. This removal/rinse step overcomes many of the complications in previous detection methods that relied upon the conformation of labeled probes rather than the presence or absence of the probes.

In an aspect, disclosed methods provide ease in detection of multiple target nucleic acids when the captors are bound to a substrate such as microbeads, with each type of captor located in a separate well or other confining region, therefore allowing the simultaneous detection of multiple target nucleic acids within a common sample.

In an aspect, a method can be used to detect the presence of the target nucleic acid, where the method comprises binding the captor to a substrate, contacting the captor with a medium potentially containing a target nucleic acid, contacting the captor with the labeled probe, rinsing the captor and determining if the labeled probe annealed to the captor.

In an aspect, a method comprises a concentration step prior to the step of mixing the target nucleic acids with captor molecules. Target nucleic acids can be concentrated using immobilized concentrating probes that are complementary to a portion of the target nucleic acids and that are immobilized by being bound to a surface. For example, concentrating may comprise exposing a sample comprising one or more target nucleic acid sequences to a composition comprising paramagnetic microbeads to which nucleic acid sequences complementary to the target nucleic acids have been bound. In an aspect, the concentrating nucleic acid sequences ("concentrating probes") on the paramagnetic microbeads can be identical or similar to one or more loop regions of captor molecules used in a method disclosed herein. In an aspect of the present disclosure, mixing the sample nucleotides in a first buffer, for instance a lysis buffer, with the paramagnetic microbeads comprising concentrating probes can bind the target nucleic acids to the paramagnetic microbeads comprising concentrating probes. After allowing for sufficient binding, the paramagnetic microbeads comprising concentrating probes and any bound target nucleic acids can be pulled out of the mixture by the application of a magnetic field and the first buffer can then be rinsed/removed from the paramagnetic microbeads comprising concentrating probes and any bound target nucleic acids. The magnetic field may or may not be removed. A second buffer, for instance a buffer for hybridization, can be added to the paramagnetic microbeads comprising concentrating probes and any bound target nucleic acids. In an alternative aspect of the present disclosure, the paramagnetic microbeads comprising concentrating probes and any bound target nucleic acids can be mixed into the second buffer. In an aspect, the second buffer/paramagnetic microbeads comprising concentrating probes and any bound target nucleic acids mixture can be heated to a temperature above the melting temperature of the target nucleic acids to release the target nucleic acids from the paramagnetic microbeads. In an aspect, the paramagnetic microbeads can then be pulled out of solution by the application of a magnetic field and the second buffer containing the target nucleic acids can be removed from the paramagnetic microbeads. In a further alternative aspect of the present disclosure, the released target nucleic acids can be analyzed in methods disclosed herein or other known nucleic acid assays.

In an aspect, exposure of organisms or cells to compounds such as drugs or antibiotics prior to assaying the organisms or cells using a stem loop captor method, system or device can be used to rapidly determine whether the organism or cells responds to the compound or molecule, by moderating the levels of target nucleic acids. As used herein, moderating means increasing or decreasing the level of a molecule from a pre-determined or known baseline level. For example, a method for assaying for bacterial sensitivity to one or more antibiotics, comprises exposing the bacteria to an antibiotic, and after a predetermined time, lysing the bacteria and measuring the amount of label detected in an assay of nucleic acids of the bacteria as disclosed herein. The amount of label detected is compared to the amount of label detected in an assay of the bacteria not exposed to the antibiotic.

In an aspect, nuclease activity in a biological or environmental sample can be inhibited prior to and during contact of the captor molecule with the sample. In an aspect, nuclease inhibition can be achieved by applying intense heat to the sample before it contacts the captor molecule. In an aspect, nuclease activity can be inhibited by using one or more surfactant compounds including SDS. In an aspect, nuclease activity can be inhibited by using one or more chelating agents including ethylenediaminetetraacetic acid (EDTA), or small organic molecules selected from the group consisting of DMSO, dithiothreitol (DTT), and urea. In an aspect, nuclease activity can be inhibited by using Proteinase K.

In an aspect, if in a sample the nucleic acids of interest (target nucleic acids) are found within an encapsulating structure such as an organism, e.g., a bacterium, the nucleic acids in the sample can be released from the structure and made available for binding to the captor molecule. In an aspect, a combination of rapidly heating the sample to a high temperature, such as passing the sample across a hot wire, adding lysing compounds such as 0.2% SDS, and/or vigorously mixing the sample with glass-zirconia beads can release the nucleic acids.

In an aspect, the released nucleic acids can be mildly degraded by incubation with divalent metal ions during or after sample lysis into sequences of approximately 50 to 500 nucleotides in length, where approximately means plus or minus 50% in this range. In an aspect, zinc ions added at a lower concentration limit of approximately 0.1 millimolar (mM) to an upper concentration limit of approximately 10 mM during the hot lysis can be used to cause the random hydrolysis of the target nucleic acids. In this range approximately means plus or minus twenty percent. In an aspect, the hydrolysis can be stopped by adding a metal chelator, including but not limited to, EDTA or diethylenetriaminepentaacetic acid (DTPA). Additionally, the released nucleic acids (RNA and DNA) can be mechanically sheared, for example, by passage through small orifices where the pressure change along the narrowing passage causes the linear nucleic acids to break (point-sink shearing.) Those of skill in the art are acquainted with methods for shearing nucleic acids.

In an aspect, disclosed methods can be performed with one or more types of captor molecules to detect multiple target nucleic acids in the same sample. The multiple target nucleic acids can be from the same agent (e.g., pathological agents such as bacteria, fungi, viruses, protozoa, other microorganisms), from different agents, or both. As used herein, "agent" includes one or more living or dead cells, tissues, organisms or intracellular organelles or fragments thereof, that contain or have released nucleic acids. If only a single type of captor molecule is used to identify a target nucleic acid or agent, then a mutation in the agent that changed the target nucleic acid to which the captor molecule was complementary can confound the detection of the target nucleic acid and, hence, the identification of the agent. The use of several types of captor molecules for binding multiple target nucleic acids from the same agent has been found to establish the identity of the target even if one or more of the target nucleic acids has a mutation. Therefore, captor molecules may be designed in sets of two (2) or more captor molecules (i.e, two types of captor molecules) that are complementary to two (2) or more target nucleic acids from the same agent. A statistical cluster approach can then be performed to see if the captor molecules have bound to a sufficient subset of available target nucleic acids to identify the agent.

In an aspect, methods of detection disclosed herein can be performed on an agent after the agent has been exposed to a compound or molecule, such as a cancer drug or antibiotic, to determine if exposure to the compound or molecule has changed the levels of target nucleic acids in the agent. Captor molecules can be designed that hybridize to target nucleic acids that may change in presence or quantity in response to the agent being exposed to the compound. After exposure of the agent to the compound, for instance incubating a sample that can contain bacteria with an antibiotic for 30 minutes at 37° C., the nucleic acids can be processed and used in disclosed methods for detecting target nucleic acids. Analysis of the presence of or changes in the abundance of target nucleic acids can be used to determine if the agent in the sample responded to the compound. A method of the present disclosure comprises detecting target nucleic acids from one or more agents using captor molecules in methods disclosed herein, wherein before detecting the target nucleic acids, the one or more agents were exposed to conditions, such as therapeutic or chemotherapeutic compounds or molecules, that caused the agents to respond by synthesizing one or more target nucleic acids or by altering the amount of target nucleic acids synthesized by the agent.

In an aspect, a rinsing solution or buffer of the present disclosure may comprise compounds or molecules that enhance the detection of the labeled probe in an assay using captor molecules to detect target nucleic acids in a sample. For example, in an aspect, the rinsing solution or buffer that is used to remove unbound labeled probes may comprise ascorbic acid. Such a rinse or buffer comprising ascorbic acid may aid in maintaining a fluorescent label and preventing or inhibiting quenching of fluourescence. An amount of ascorbic acid from about 0.01 to about 10.0 mM can be used, and all ranges therein between. For example, a rinse comprising 0.1 mM ascorbic acid can be used in the buffer or solution to improve the detectability of the labeled probe.

In an aspect, methods disclosed herein can detect the binding of target nucleic acids by captor molecules by detecting changes in electrical current, in view of the conformational change in the captor molecule. The devices for measuring such changes in current due to conformational changes are known to those of skill in the art. After binding target nucleic acid molecules, the captor is in an open configuration and the change in the captor from a closed (hairpin) structure to the open structure can be measured by a change in an electric current applied across the assay structure. Such a conformational change may also be measured by other methods that can detect a change in conformation of a molecule or in the liquids surrounding such the molecule undergoing a conformational change.

A method for detecting target nucleic acids, comprises providing target nucleic acids to a device comprising a substrate to which captor molecules are attached and spaced apart from one another, and adding a sample potentially comprising target nucleic acids, hybridizing the target nucleic acids (if present) with a complementary loop sequence in the presence of slightly denaturing hybridization buffer and optionally, heat; adding a probe having a sequence that is complementary to at least a portion of a stem region of a captor molecule and that is shorter in length than the entire complementary stem region, adding a rinsing buffer to remove unbound nucleic acids, and detecting bound label. Optionally, the substrate may be contacted by competitive binding inhibitors before or after attaching captor molecules. Optionally, target nucleic acids may be hybrized with helper oligos prior to being added to the captor molecules. Optionally, target nucleic acids may be concentrated prior to the addition of helper oligos or being added to captor molecules.

The heating step may comprise temperatures from room temperature (e.g. 24° C.) to about 50° C., to about 51° C., to about 52° C., to about 53° C., to about 54° C., to about 55° C., to about 56° C., to about 57° C., to about 58° C., to about 59° C., to about 60° C., to about 61° C., to about 62° C., to aid hybridization such as to create single stranded sections of nucleic acids. Methods disclosed herein do not contemplate temperatures of about 65° C. and higher.

Devices

Disclosed herein are devices comprising captor molecules, as disclosed herein. The one or more types of captor molecules are attached to a substrate. A captor molecule may be attached directly to a substrate or may be attached to a linker. Captor molecules may be attached in any desired pattern on the substrate, for example in a particular assay design for a solid planar substrate or captors may be attached to particles or beads, for example, that are segregated in particular containers such as wells in a plate. In an aspect, on a planar substrate, captor molecules may be spaced apart from one other by at least half of the length of the closed hairpin of a captor molecule. Other spacing distances are contemplated that alleviate the cross-binding of one captor molecule to another.

In an aspect, a device may be prepared using a substrate such as an NSB27 slide (NSB USA Inc., Los Alamitos, Calif.) that is manufactured with a dendron coating that separates reactive surface attachment sites. The reactive surface attachment sites are separated from each other at a distance of approximately 0.8 nanometers to a distance of approximately 14 (14) nanometers, from about 2 to about 10 nm, from about 4 to about 8 nm, and ranges therein between. The reactive surface attachment sites on the NSB27 slides can be, for example, aldehyde moieties, which can react to form a covalent linkage with a primary amino group at the end of a linker attached to a captor molecule. In an aspect, the captor molecule can have a 5' linker consisting of a six (6) carbon chain with a primary amino group on the carbon at the opposite end from the captor sequence. In an aspect, the captor molecule with such a linker can be diluted in an attachment buffer with a final concentration of 2.5% glycerol and 200 mM of a mixture of monosodium phosphate and disodium phosphate to reach a pH of 8.5. Captors may be diluted as low as $1\times10^{-1}$ µM; or diluted to 1 µM in the presence of 3 µM of a binding competitor, such as a 10 nucleotide polyA DNA with the same chemical linker as the captor, see SEQ ID NO: 30. One or more types of captor molecules may be prepared by such dilutions. Each type of captor molecule may be deposited in a particular location on the substrate through, for example, contact microarray printing technology or through Piezo-droplet microarray printing technology or by other printing technologies known to those familiar with the art.

In an aspect, the present disclosure relates to devices that can be used for rapidly and sensitively detecting the presence of one or more target nucleic acid sequences within an environmental or biological sample.

In an aspect, a disclosed device comprises at least one captor molecule attached to a surface of the device. In an aspect, the surface of a disclosed device is an external surface, e.g., a surface of a microscope slide, an assay plate, a bead, or a particle. In an aspect, the surface of a disclosed device is an interior surface, e.g., a surface within a chamber such as microfluidic chamber. Attachment of a captor molecule to a surface may comprise known types of binding, including but not limited to, covalent, ionic, van der Waals, antibody-antigen, and substrate-receptor binding.

In an aspect, a disclosed device comprises one or more stem loop captor molecule nucleic acid molecules. Such captor molecules are attached to a surface of a device by binding the 5' end of the nucleic acid captor molecule. In an aspect, a device is an array for detecting target nucleic acids in a sample. An array is comprised of multiple sites comprising a plurality of captor molecules, wherein one or more of the multiple sites comprises a plurality of captor molecules having a target binding sequence (in the loop section of the captor molecule) that is capable of binding to specific target nucleic acids. In an aspect, an array further comprises control nucleic acid stem-loop captor molecules that provide a positive control for the presence of a particular target sequence in a sample that is complementary to the target sequence so that binding occurs between the control nucleic acid sequence, located in the loop section of the control captor molecule, and the target sequence.

In an aspect, an array further comprises control nucleic acid stem-loop captor molecules that provide a negative control for the presence of a particular target sequence in a sample that is not complementary to the target sequence so that no binding occurs between the control nucleic acid sequence, located in the loop section of the control captor molecule, and the target sequence. In an aspect, a negative control captor molecule has a sequence that is very similar to the captor molecule, but is not identical to the captor molecule, such that the control captor molecule is a specific negative control for a specific captor molecule. For example, a captor molecule sequence can be Rt16-788 (SEQ ID NO: 167) and a specific negative control sequence for Rt16-788 can be Rt16-788X (SEQ ID NO: 168). A specific negative captor molecule provides for a highly discriminative negative control measurement for an array comprising captor molecules and negative control captor molecules. In an aspect, an array may comprise captor molecules or other nucleic acid structures that bind nucleic acids that are not related to the target sequence, which serve as an internal control of binding conditions of the array.

In an aspect, a device disclosed herein comprises multiple sites wherein at each site, a step in a method of detecting a target nucleic acid is performed. For example, a device can be a tube having a non-dispersing gel within it. The gel may have several layers or sections, each providing a site for performing a step in a method of detecting a target nucleic acid. For example, a device can be a microfluidic device having multiple sites comprised of chambers that are microfluidically connected in a particular pattern so that the steps of a method of detecting a target nucleic acid can be performed in a particular sequence. For example, a device can be a series of containers, such as microcentrifuge tubes, connected in a particular pattern so that the steps of a method of detecting a target nucleic acid can be performed in a particular sequence. For example, the sites for a step in a method of detecting a target nucleic acid comprise a) a site to contact and possibly bind the sample target nucleic acid with a captor molecule, b) a wash or rinse site to remove unbound sample nucleic acids, c) a site for labeled detector molecule interaction with the captor molecule having a bound target nucleic acid, d) a wash or rinse site to remove unbound detector molecules, and a collection site where detection of the labeled detector-captor molecule-target nucleic acid construct occurs. Devices may comprise sites for pre-treatment steps such as treating the sample to expose and/or fragment nucleic acids from the sample.

In an aspect, a site for interaction of the sample nucleic acids and the captor molecules can be separate from the device with multiple sites. For example, a sample, such as saliva, can be mixed with captor molecules that are attached to the surface of paramagnetic beads. It is contemplated that a plurality of one type of captor molecules, each captor molecule having the same, identical sequence for binding a target nucleic acid, is bound to a paramagnetic bead, and a plurality of captor molecule-bound paramagnetic beads (which may comprise one type or more than one type of captor molecules) are used in an assay. The mixture of the captor molecule-bound beads and sample may comprise buffers for lysing pathogens or micoorganisms in the sample and/or fragmenting the nucleic acids of the pathogens or microorganisms. This mixture comprising annealed nucleic acids may then be added to the device. Alternatively, the site for interaction of the sample nucleic acids and the captor molecule-bound paramagnetic beads can be located in the device.

For example, wherein the device is a tube having multiple sites for interaction such as in a layered structure or gel, having a closed end and an open end, describing the sites or layers for the steps of the method from the open end of the tube is as follows. The first layer can either be the site for the step of interaction of the sample nucleic acids and the captor molecules, which are bound to paramagnetic beads, and the treatments of lysing, fragmenting, heating, lysing and cooling as described above, or can be the site where the mixture comprising annealed nucleic acids of the target nucleic acid and the captor molecule bound to the paramagnetic bead is introduced into the tube. The second layer provides buffers or solutions for rinsing and removing any unbound nucleic acids. Alternatively, the rinsing may occur as a step prior to adding the annealed nucleic acids of the target nucleic acid and the captor molecule bound to the paramagnetic bead to the tube. The third layer comprising labeled detector molecules that bind to single stranded portions of the captor molecules that have bound target nucleic acids. The fourth layer comprises buffers or solutions for removing unbound detector molecules, and the fifth layer, generally the bottom layer, comprises a collection site for labeled bound captor molecules. A detector detects the labeled molecules in the collection site and from that measurement, the assay determines the presence or absence of the target sequences in the sample. The paramagnetic beads are moved down through the tube by magnetic force applied by a magnet moving from the top of the tube to the bottom of the tube. For example, a ring magnet or solenoid (a circular electromagnet), encircling the tube can be used.

Alternatively, a device can be a microfluidic device having chambers having functions as described for the layers for the above tube format. The sample is added to the microfluidic device and a first chamber can either be the for the step of interaction of the sample nucleic acids and the captor molecules, which are bound to paramagnetic beads, and the treatments of lysing, fragmenting, heating, lysing and cooling as described above, or can be the site where the mixture comprising annealed nucleic acids of the target nucleic acid and the captor molecule bound to the paramagnetic bead is introduced into the device. A second chamber provides buffers or solutions for rinsing and removing any unbound nucleic acids, or such buffers or solutions can be introduced into the first chamber. Alternatively, the rinsing may occur as a step prior to adding the annealed nucleic acids of the target nucleic acid and the captor molecule bound to the paramagnetic bead to the microfluidic device. The rinsed paramagnetic beads can be moved to the next chamber, e.g., a third chamber, and a solution comprising labeled detector molecules that bind to single stranded portions of the captor molecules that have bound target nucleic acids is added. After interaction between the captor molecule-bound paramagnetic beads and the detector molecules, the beads can be rinsed in the chamber or be moved to the next chamber, e.g., the fourth chamber where buffers or solutions for removing unbound detector molecules are provided. Detection may take place in this chamber or the captor molecule-bound labeled beads or moved to the next chamber, e.g., the fifth chamber, which comprises a collection site for labeled bound captor molecules. A detector detects the labeled molecules in the collection site and from that measurement, the assay determines the presence or absence of the target sequences in the sample. The paramagnetic beads are moved through the microfluidic device by magnetic force applied by a magnet moving from the first chamber through the next chambers of the device.

In an aspect, a disclosed device can be a fiber, such as glass or plastic fiber optic fibers or cable. A fiber optic fiber may comprise two ends, a first end and a second end, separated by the length of the fiber. In an aspect, a plurality of captor molecules is bound on the first end. The captor molecules on one fiber can be the same type or of a related type. A plurality of fibers can be used in a disclosed method, wherein each fiber has particular captor molecules bound to a first end. The method of detection of bound labeled probes is performed using the steps described herein, and the radiation or light (photons) from a labeled captor molecule is transmitted from the first end through the fiber optic fiber to the second end of the fiber optic fiber. A detector is adjacent to or contacted by the second end of the fiber optic fiber such that the radiation or light is detected.

In an aspect, the use of fibers, such as fiber optic fibers, to transmit the radiation of a detectable label attached to, in contact with, or adjacent to the fiber, can be used in any assay that incorporates such a detectable label. Assays comprising such fibers are not limited to the assays described herein, and are not limited to assays comprising captor molecules and detector molecules, but include any assays comprising suitable detectable labels, including but not limited to, ELISA, antibody assays, metabolic assays, enzymatic assays, and the like.

In an aspect, a disclosed device can be used in a detection system comprising a time-of-flight sensor with a filter that can detect the wavelength of the radiation of the label in the labeled probe. Time-of-Flight (ToF) is a method for measuring the distance between a sensor and an object, in this case a labeled detector on a captor molecule, based on the time difference between the emission of a signal and its return to the sensor, after being reflected by an object. Various types of signals (also called carriers) can be used with ToF, for example, light. Light is a particularly good carrier for biological assays, because it is uniquely able to combine speed, range, low weight and eye-safety. Technology based on time-of-flight (ToF) for range finding is very powerful when used with light. Light time-of-flight sensors may perform as well as laser scanners or other methods of imaging fluors. Assays comprising such time of flight sensors are not limited to the assays described herein, and are not limited to assays comprising captor molecules and detector molecules, but include any assays comprising suitable detectable labels, including but not limited to, ELISA, antibody assays, metabolic assays, enzymatic assays, and the like.

Data acquired from disclosed devices may be transmitted via wireless or wired transmission from a detector determining the results from interactions in disclosed devices and uploaded to a storage data base or other data recipient. Data can be acquired from devices disclosed herein and used for multiple purposes. For example, the data can be tagged with geolocation and time coordinates, providing a time/space location of the data and any resulting diagnosis or prognosis. The compiled data can be manipulated, for example, sorted and reported for many purposes, including, but not limited to, near real-time infection monitoring for public health warnings, quality control, travel advisories, pandemic management and medicine inventory.

Kits

In an aspect, the present disclosure relates to kits that can be used for rapidly and sensitively detecting the presence of one or more target nucleic acid sequences within an environmental or biological sample.

In an aspect, the present disclosure relates to kits comprising at least one of: (a) a nucleic acid captor molecule comprising a loop region and a stem region, wherein the nucleic acid captor molecule has a closed stem-loop structure; and wherein the closed stem-loop structure is replaced with an open stem-loop structure when the nucleic acid captor molecule contacts a target nucleic acid; or (b) a labeled probe; wherein the labeled probe comprises a disclosed probe sequence linked to a disclosed label; and wherein the labeled probe binds to the stem region of the open stem-loop structure; and optionally comprising one or more of (c) an incubation buffer; (d) a rinsing buffer; (e) a final rinse buffer; and (f) instructions for one or more of incubating and rinsing the nucleic acid captor molecule with a sample, incubating and rinsing after adding the labeled nucleic acid probe and final rinsing before detecting the presence of the labeled nucleic acid probe.

In an aspect, a disclosed kit comprises: (a) a nucleic acid captor molecule comprising a loop region and a stem region, wherein the nucleic acid captor molecule has a closed stem-loop structure; and wherein the closed stem-loop structure is replaced with an open stem-loop structure when the nucleic acid captor molecule contacts a target nucleic acid; (b) a labeled probe; wherein the labeled probe comprises a disclosed probe sequence linked to a disclosed label; and wherein the labeled probe binds to the stem region of the open stem-loop structure; and optionally comprising one or more of (c) an incubation buffer; (d) a rinsing buffer; (e) a final rinse buffer; and (f) instructions for one or more of incubating and rinsing the nucleic acid captor molecule with a sample, incubating and rinsing after adding the labeled nucleic acid probe and final rinsing before detecting the presence of the labeled nucleic acid probe.

In an aspect, a disclosed kit comprises components and methods disclosed herein of using the nucleic acid detector to indicate the presence of a target nucleic acid in which a labeled probe binds to a captor molecule if the captor molecule has hybridized with the target nucleic acid, thereby reducing background noise. In an aspect, a disclosed kit comprises a labeled probe and a captor molecule, where the labeled probe binds to the captor molecule if the captor molecule has hybridized with the target nucleic acid. In an aspect, a disclosed kit can be used to perform a method for screening gene expression levels. In an aspect, a disclosed kit can be used to determine gene expression level changes in response to a drug or other stimulus. In an aspect, a disclosed kit can be used to determine gene expression level changes in response to a compound that stimulates cells.

In an aspect, a disclosed kit comprises one or more captor molecules linked to a surface in a well of an assay plate, e.g., a 12-well, 24-well, 48-well, 96-well, or 384-well. In an aspect, each well of the plate can comprise clusters of captor molecules in each well, where only the loop sequences of the captor molecules differ from cluster to cluster and wherein each of the loop sequences of a cluster are complementary to a portion of the nucleic acids of an agent of interest. In this manner, the presence of multiple target nucleic acids can be simultaneously detected by use of various captor molecules upon the same substrate. In an aspect, the presence of the target nucleic acids can be indicated, for instance, by fluorescence, on the substrate region corresponding to the cluster of captor molecules that have hybridized to that target nucleic acid and subsequently hybridized with the labeled probe.

In an aspect, a disclosed kit comprises a slide comprising clusters of captor molecules upon corresponding regions of a substrate wherein only the loop sequences of the captor molecules differ from cluster to cluster and wherein each of the loop sequences of a cluster are complementary to a portion of the nucleic acids of an agent of interest. In this manner, the presence of multiple target nucleic acids can be simultaneously detected by use of various captor molecules upon the same substrate. In an aspect, the presence of the target nucleic acids can be indicated, for instance, by fluorescence, on the substrate region corresponding to the cluster of captor molecules that have hybridized to that target nucleic acid and subsequently hybridized with the labeled probe.

In an aspect, the captor molecules of each cluster are designed with differing loop sequences, but with stem regions that contain a sequence complementary to the labeled probe. Use of multiple captor molecules having stem regions with at least a portion of their stem regions identical allows use of a universal labeled probe that binds to any exposed stem region of the captor molecules regardless of the loop region of the captor molecule. Thus, a universal labeled probe can be used with the assay, where all labeled probes have identical sequences. Use of a universal labeled probe greatly simplifies the detection process by requiring the preparation of only a single labeled probe sequence.

In an aspect, a disclosed kit comprises microbeads linked to captor molecules. In an aspect, a kit comprising microbeads further comprises instructions for placing the microbeads in separate wells or tubes. By placing a separate biological sample into each well or tube, multiple samples can be simultaneously assayed. The presence of target nucleic acids can be indicated, for instance, by fluorescence, in the well or tube corresponding to the captor molecules that have hybridized to target nucleic acids and subsequently hybridized with the labeled probe.

In an aspect, a kit includes a nucleic acid captor, one or more nucleic acid probes and instructions for preparation of one or more incubation buffers. In an aspect, a kit includes the nucleic acid captor, one or more nucleic acid probes, instructions for the use of the kit and instructions for the preparation of one or more incubation buffers. In an aspect, a kit includes the nucleic acid captor, one or more nucleic acid probes, instructions for the use of the kit and instructions for the preparation of one or more incubation buffers, one or more binding buffers and one or more detection buffers. In an aspect, a kit includes the nucleic acid captor and one or more nucleic acid probes. In an aspect, a kit includes the nucleic acid captor, one or more nucleic acid probes and one or more buffer solutions.

In an aspect, a kit containing components described herein for performing the method of a universal labeled probe and substrate bound captors can be used to detect the presence of multiple target nucleic acids in a sample.

In an aspect, the kit requires conditions in which the selected captors can rapidly and selectively hybridize to their target nucleic acids and conditions in which the labeled probe can rapidly and selectively bind to exposed captor regions.

In an aspect, disclosed herein are systems comprising a disclosed device comprising captor molecules, probe molecules, and optionally competitive inhibitor molecules and specific buffers.

Disclosed Nucleic Acid Sequences

In an aspect, a disclosed nucleic acid sequences is a sequence set forth in Table I. The sequences in Table I include nucleic sequences for target molecules, captor molecules, and specific control sequences for captor molecules. The SEQ ID NOs associated with each sequence is provided in Table I.

TABLE I

List of nucleic acid sequences with SEQ ID NO.

| SEQ ID NO. | Name | Sequence | Captor (C) Target (T) Probe (P) Helper (H) |
|---|---|---|---|
| 1 | Ec632 | GACAGACAGACAGACACTCAAGCTTGCCAGTATCAGATGCTGTCTGTCTGTCTGTC | C |
| 2 | 13D | GACAGACAGACAG | P |
| 3 | Pos1-C2 | GA+CAGACAGA+CAGACATAGATCTCCTCCGTCCAATATCCTTGTCTGTCTGGA+CAGACAGA+CAGACATAGATCTCCTCCGTCCAATATCCTTGTCTGTCTGTCTGTC | C |
| 4 | Ecoli476 | GACAGACAGACAGACACTGCGGGTAACGTCAATGAGCAAAGAAAATGTCTGTCTGTCTGTC | C |
| 5 | Ecoli476-14 | GACAGACAGACAGACTGCGGGTAACGTCAATGAGCAAAGAAAATCTGTCTGTCTGTC | C |
| 6 | Ecoli476-12 | GACAGACAGACACTGCGGGTAACGTCAATGAGCAAAGAAAATGTCTGTCTGTC | C |
| 7 | 16D | GACAGACAGACAGACA | P |
| 8 | Sau453mA | GACAGACAGACAGACAGTTACTTACACATATGTTCTTCCCTGTCTGTCTGTCTGTC | C |
| 9 | Sau453T | GGGAAGAACATATGTGTAAGTAACTGT | T |
| 10 | Sau453TC2 | GGGAAGAACATCTGTGTCAGTAACTGT | T |
| 11 | Sau453TG2 | GGGAAGAACATGTGTGTGAGTAACTGT | T |
| 12 | Sau453T14C | GGGAAGAACATATCTGTAAGTAACTGT | T |
| 13 | Sau453T6-27 | GAACATATGTGTAAGTAACTGT | T |
| 14 | Sau453T1-22 | GGGAAGAACATATGTGTAAGTA | T |
| 15 | Sau453n | CAGAGACAGACAGACAGTTACTTACACATATGTTCTTCCCTGTCTGTCTGTCTCTG | C |
| 16 | 11Dn | CAGAGACAGAC | P |
| 17 | Pos1 | GACAGACAGACAGACATAGATCTCCTCCGTCCAATATCCTTGTCTGTCTGTCTGTC | C |
| 18 | Pos1T | AGGATATTGGACGGAGGAGATCTATG | T |
| 19 | SamecA1 | GACAGACAGACAGACAGTTCTGCAGTACCGGATTTGCCAATGTCTGTCTGTCTGTC | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 20 | SamecA1T | ATTGGCAAATCCGGTACTGCAGAACT | T |
| 21 | Sau71 | GACAGACAGACAGACAGAAGCAAGCTTCTCGTCCGTT GTCTGTCTGTCTGTC | C |
| 22 | Sau453 | GACAGACAGACAGACAGTTACTTACACATATGTTCTT CCCAAAATGTCTGTCTGTCTGTC | C |
| 23 | Ec632S | GCATCTGATACTGGCAAGCTTGAGT | T |
| 24 | 13Dn | GACAGACAGACAG | P |
| 25 | CHIKV-1 | GACAGACAGACAGACCCATACCAGTTTACCTTCCGTA CGCGGTCTGTCTGTCTGTC | C |
| 26 | CV1S | GCGTACGGAAGGTAAACTGGTATGG | T |
| 27 | SapurK1 | GACAGACAGACAGACAAGCTGACCACCACCAATAATG CCATGTCTGTCTGTCTGTC | C |
| 28 | SapurK1T | TGGCATTATTGGTGGTGGTCAGCTTG | T |
| 29 | Ec3 | GACAGACAGACAGACAACAACACCGGTGAAATGTTCT TCATGTCTGTCTGTCTGTC | C |
| 30 | 10A CI | AAAAAAAAAA | COMPETITIVE INHIBITOR |
| 31 | Ec3S | TGAAGAACATTTCACCGGTGTTGTTG | T |
| 32 | CCHFL-350 | ACACAGGAAGAGACACCACTCGTTGTCAGACAGCATC CTTGTCTCTTCCTGTGT | C |
| 33 | CCHFL-350X | ACACAGGAAGAGACACCACTCGTTGTGTGACAACATC CTTGTCTCTTCCTGTGT | C |
| 34 | CCHFL-7448 | ACACAGGAAGAGACATAACGCCATGAGTCCTTTGCTT ATTGTCTCTTCCTGTGT | C |
| 35 | CCHFL-7448X | ACACAGGAAGAGACATAACGCCAAGACACCATTGCTT ATTGTCTCTTCCTGTGT | C |
| 36 | CCHFM-5338 | ACACAGGAAGAGACACTCAAAGATATAGTGGCGGCAC GCATGTCTCTTCCTGTGT | C |
| 37 | CCHFM-5338X | ACACAGGAAGAGACACTCAATCTTATAGTGGCGGTAC GCATGTCTCTTCCTGTGT | C |
| 38 | CCHFS-1638 | ACACAGGAAGAGACATCGGTTGCCGCACAGCCCTTTA AGTTGTCTCTTCCTGTGT | C |
| 39 | CCHFS-1638X | ACACAGGAAGAGACATCGGGTGCCGCACATGGGTTGT AGTTGTCTCTTCCTGTGT | C |
| 40 | CKV-10226 | ACACAGGAAGAGACATAGACGCCGGTGAAGACCTTAC AGTGTCTCTTCCTGTGT | C |
| 41 | CKV-10226X | ACACAGGAAGAGACATAGACGCCGGTGAAGACCTTAC AGTGTCTCTTCCTGTGT | C |
| 42 | CKV-2928 | ACACAGGAAGAGACACATACCAGTTTACCTTCCGTAC GCTGTCTCTTCCTGTGT | C |
| 43 | CKV-2928X | ACACAGGAAGAGACACATACCAGTTTACCTTCCGTAC GCTGTCTCTTCCTGTGT | C |
| 44 | CKV-5336 | ACACAGGAAGAGACAGGACGCTAGCCATGGGTGTTAT ATTGTCTCTTCCTGTGT | C |
| 45 | CKV-5336X | ACACAGGAAGAGACAGGACGCTAGGGATGGGTGTAAT ATTGTCTCTTCCTGTGT | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 46 | CKV-5537 | ACACAGGAAGAGACAGTAGCTCAGAAGACAAGCTTTCGATGTCTCTTCCTGTGT | C |
| 47 | CKV-5537X | ACACAGGAAGAGACAGTTGCACAGATGACATGCATTCGATGTCTCTTCCTGTGT | C |
| 48 | Cspec18S-1213PR | ACACAGGAAGAGACAAATCCTTATTGTGTCTGGACCTGGTGTGTCTCTTCCTGTGT | C |
| 49 | DV123-10643 | ACACAGGAAGAGACACTGTGCCTGGAATGATGCTGAGGATGTCTCTTCCTGTGT | C |
| 50 | DV123-10643X | ACACAGGAAGAGACACTGTGCCTGGATAGTTGCTGAGGATGTCTCTTCCTGTGT | C |
| 51 | DV1-8478 | ACACAGGAAGAGACATCATATGATCCATGATAGGCCCATTGTCTCTTCCTGTGT | C |
| 52 | DV1-8478X | ACACAGGAAGAGACATCATATGATCCTTGAATGCCCATTTGTCTCTTCCTGTGT | C |
| 53 | DV2-2188 | ACACAGGAAGAGACAAGCTGTGTCACCTAAAATGGCCAATGTCTCTTCCTGTGT | C |
| 54 | DV2-2188X | ACACAGGAAGAGACAAGCTCTCTCACTCAAAATCGCCAATGTCTCTTCCTGTGT | C |
| 55 | DV23-5391 | ACACAGGAAGAGACATGCTGGGTCTGTGAAATGGGCTTCTGTCTCTTCCTGTGT | C |
| 56 | DV23-5391X | ACACAGGAAGAGACATGCAGGGTCTTGGAAATGGGCTTCTGTCTCTTCCTGTGT | C |
| 57 | DV3-1455 | ACACAGGAAGAGACATTCTAGCCCAAGGGTTCCATATTCTGTCTCTTCCTGTGT | C |
| 58 | DV3-1455X | ACACAGGAAGAGACATTCTAGCCCTTGGGTTCCATTATCTGTCTCTTCCTGTGT | C |
| 59 | DV3-7669 | ACACAGGAAGAGACATCTTTGGCTTCTGTTCTATCCACTTGTCTCTTCCTGTGT | C |
| 60 | DV3-7669X | ACACAGGAAGAGACATCTTAGGCTTCTGATCTATCCTCTTGTCTCTTCCTGTGT | C |
| 61 | DV4-1762 | ACACAGGAAGAGACAAGATGTCCTGCAAACATGTGATTTCTGTCTCTTCCTGTGT | C |
| 62 | DV4-1762X | ACACAGGAAGAGACAAGATGTCCTGCTTTCATGTGATTTCTGTCTCTTCCTGTGT | C |
| 63 | DV4-6523 | ACACAGGAAGAGACAAGCATGAGTGTTTCCAGTGACTCCGTGTCTCTTCCTGTGT | C |
| 64 | DV4-6523X | ACACAGGAAGAGACAGCATGTGAGTTTCCAGTGTCACCGTGTCTCTTCCTGTGT | C |
| 65 | DV4-8789 | ACACAGGAAGAGACACTGTTCTTCCTGAAAGACTGCGCCTTGTCTCTTCCTGTGT | C |
| 66 | DV4-8789X | ACACAGGAAGAGACACTGTTCAACCTGATTGACTGCGCCTTGTCTCTTCCTGTGT | C |
| 67 | Ec16S-467P | ACACAGGAAGAGACACGGGTAACGTCAATGAGCAAAGGTTGTCTCTTCCTGTGT | C |
| 68 | Ec23S-1472PR | ACACAGGAAGAGACACAGCCTACACGCTTAAACCGGGACTGTCTCTTCCTGTGT | C |
| 69 | Ec23S-2722PR | ACACAGGAAGAGACACATCTCGGGGCAAGTTTCGTGCTTTGTCTCTTCCTGTGT | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 70 | Ec632P | ACACAGGAAGAGACACTCAAGCTTGCCAGTATCAGAT GCTGTCTCTTCCTGTGT | C |
| 71 | EcdnaK1p | ACACAGGAAGAGACATGAGCATCGTTAAAGTATGCCG GTTGTCTCTTCCTGTGT | C |
| 72 | EcfusA1P | ACACAGGAAGAGACAACAACACCGGTGAAATGTTCTT CATGTCTCTTCCTGTGT | C |
| 73 | EcompA1P | ACACAGGAAGAGACATAACCCAGAACAACTACGGAAC CGTGTCTCTTCCTGTGT | C |
| 74 | EcrspA1P | ACACAGGAAGAGACATAGCTTTGCACTGTTTCAGACC CATGTCTCTTCCTGTGT | C |
| 75 | EcthrS1P | ACACAGGAAGAGACACAATTTTCGGACCGTAGAAAGC GCTGTCTCTTCCTGTGT | C |
| 76 | Efs16S-167PR | ACACAGGAAGAGACAACTGTTATGCGGTATTAGCACC TGTTGTCTCTTCCTGTGT | C |
| 77 | EU-1063P | ACACAGGAAGAGACAAACATTTCACAACACGAGCTGA CGTGTCTCTTCCTGTGT | C |
| 78 | EU-1063PX | ACACAGGAAGAGACAAACATTCTACAAACCGAGCTGA CGTGTCTCTTCCTGTGT | C |
| 79 | EU-168P | ACACAGGAAGAGACACTTGCGACGTTATGCGGTATTA GCTGTCTCTTCCTGTGT | C |
| 80 | EU-367P | ACACAGGAAGAGACACATCAGGCTTGCGCCCATTGTG TCTGTCTCTTCCTGTGT | C |
| 81 | EU-504P | ACACAGGAAGAGACACGGCTGCTGGCACGGAGTTAGT GTCTCTTCCTGTGT | C |
| 82 | EU-775P | ACACAGGAAGAGACACCAGGGTATCTAATCCTGTTTG CTCCTGTCTCTTCCTGTGT | C |
| 83 | EU-775PX | ACACAGGAAGAGACACCAGGGTTTCTACTACTGTTTG CTCCTGTCTCTTCCTGTGT | C |
| 84 | EU-928AP | ACACAGGAAGAGACATAAAACTCAAAGGAATTGACGG GTGTCTCTTCCTGTGT | C |
| 85 | EU-928APX | ACACAGGAAGAGACATAAAACTCTTATGAAAGACGG GTGTCTCTTCCTGTGT | C |
| 86 | EU-928BP | ACACAGGAAGAGACATAAAACTCAAATGAATTGACGG GTGTCTCTTCCTGTGT | C |
| 87 | EU-928BPX | ACACAGGAAGAGACATAAAACTCTTAGGAAAGACGG GTGTCTCTTCCTGTGT | C |
| 88 | EV68-2A-1P | ACACAGGAAGAGACACAGTGAAAGCTACAATTCCACC CCTGTCTCTTCCTGTGT | C |
| 89 | EV68-2C-1P | ACACAGGAAGAGACAGGTTCAATGCGAGATTTGGACT TGAC(T)GTCTCTTCCTGTGT | C |
| 90 | EV68-2C-2P | ACACAGGAAGAGACATTGGTGCATGTATTGAGCCAGC ATTGTCTCTTCCTGTGT | C |
| 91 | EV68-3C-1P | ACACAGGAAGAGACATTGAGCTCCATTTCCACCTACA TGTGTCTCTTCCTGTGT | C |
| 92 | EV68-3D-2P | ACACAGGAAGAGACATAGAGTATGCAGGTAGTGTCAA TGCA(T)GTCTCTTCCTGTGT | C |
| 93 | FAV2-124 | ACACAGGAAGAGACAAATCCATGGTGTATCCTGTTCC TGTGTCTCTTCCTGTGT | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 94 | FAV2-124X | ACACAGGAAGAGACAAATCCATGGCCTATCCTCTTCC TGTGTCTCTTCCTGTGT | C |
| 95 | FAV2-2255 | ACACAGGAAGAGACATCTTCAATGGTGGAACAGATCT TCTGTCTCTTCCTGTGT | C |
| 96 | FAV2-2255X | ACACAGGAAGAGACATCTTCAATCCTGCTACAGATCT TCTGTCTCTTCCTGTGT | C |
| 97 | FAV3-2109 | ACACAGGAAGAGACAAAAGCAAAACCCAGGGATCATT TCTGTCTCTTCCTGTGT | C |
| 98 | FAV3-2109X | ACACAGGAAGAGACACGGACGAACGAAATGAATCCCA CTTGTCTCTTCCTGTGT | C |
| 99 | FAV3-585 | ACACAGGAAGAGACACGGACTGACGAAAGGAATCCCA CTGTCTCTTCCTGTGT | C |
| 100 | FAV3-585X | ACACAGGAAGAGACACGGACGAACGAAATGAATCCCA CTTGTCTCTTCCTGTGT | C |
| 101 | FAV3-663 | ACACAGGAAGAGACAGGGAGACTTTGGTCGGCAAGCG GGTGTCTCTTCCTGTGT | C |
| 102 | FAV3-663X | ACACAGGAAGAGACAGGGAGACTAAGGTCGTCAAGCG GGTGTCTCTTCCTGTGT | C |
| 103 | FAV5-1501 | ACACAGGAAGAGACATCTGCATTGTCTCCGAAGAAAT AAGTGTCTCTTCCTGTGT | C |
| 104 | FAV5-1501X | ACACAGGAAGAGACATCTGCATTCTCTCGCAAGAAAT AAGTGTCTCTTCCTGTGT | C |
| 105 | FAV7-38 | ACACAGGAAGAGACATACGTTTCGACCTCGGTTAGAA GTGTCTCTTCCTGTGT | C |
| 106 | FAV7-38X | ACACAGGAAGAGACACGGACGAACGAAATGAATCCCA CTTGTCTCTTCCTGTGT | C |
| 107 | Kp16S-023PR | ACACAGGAAGAGACATCTGGGCACATCTGATGGCATG AGTGTCTCTTCCTGTGT | C |
| 108 | Kp23S-313PR | ACACAGGAAGAGACAACCCTGTACCGTCGGACTTTCC AGTGTCTCTTCCTGTGT | C |
| 109 | LASV124-3914P | ACACAGGAAGAGACAACACGCACAGTGGATCCTAGGC AATGTCTCTTCCTGTGT | C |
| 110 | LASV2-3914X | ACACAGGAAGAGACAACTCGCACTGTGGATCCTAGGC AATGTCTCTTCCTGTGT | C |
| 111 | LASV2-978P | ACACAGGAAGAGACATGTCACAAAATTCTTCATCATG TTTGTCTCTTCCTGTGT | C |
| 112 | LASV2-978X | ACACAGGAAGAGACATGTCACAAAATTCTTCATCAAG ATTGTCTCTTCCTGTGT | C |
| 113 | LASV3-1518P | ACACAGGAAGAGACACCTCTTCCATCTGACAGGCA CATGTCTCTTCCTGTGT | C |
| 114 | LASV3-2320P | ACACAGGAAGAGACACTCGATTGTGGGAAGAGCATGG GATGTCTCTTCCTGTGT | C |
| 115 | LASV3-3315P | ACACAGGAAGAGACAAAGGGTCAGACAACCATCACGA CATGTCTCTTCCTGTGT | C |
| 116 | LASV3S-1518 | ACACAGGAAGAGACACACCTCATCCTACTGACAGGCA CATGTCTCTTCCTGTGT | C |
| 117 | LASV3S-2320 | ACACAGGAAGAGACACTCGATAGTGGAGAGAGCATGG GATGTCTCTTCCTGTGT | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 118 | LASV3S-3315 | ACACAGGAAGAGACAATGGGTCTGACAACCATCTCGACATGTCTCTTCCTGTGT | C |
| 119 | LASV4-1592P | ACACAGGAAGAGACAACTAGTGATGCTGTTGACAATTTCATTGTCTCTTCCTGTGT | C |
| 120 | LASV4-2301P | ACACAGGAAGAGACAGGAAGGGCCTGGGAAAACACTCAATGTCTCTTCCTGTGT | C |
| 121 | LASV4-2506P | ACACAGGAAGAGACAGAGTCTGACCTTGAGTATTCTTGGTGTCTCTTCCTGTGT | C |
| 122 | LASV4-4872P | ACACAGGAAGAGACAGATGACATGGTCTACAATGCAAAAATGTCTCTTCCTGTGT | C |
| 123 | LASV4L-1592X | ACACAGGAAGAGACACATGTGATGCTGTTGACGAATTCATGTCTCTTCCTGTGT | C |
| 124 | LASV4L-4872X | ACACAGGAAGAGACAGATGACTAGGTCTACATAGCAATAATGTCTCTTCCTGTGT | C |
| 125 | LASV5-30P | ACACAGGAAGAGACAAGACAGTCAAAATGCCTAGGATCCTGTCTCTTCCTGTGT | C |
| 126 | LASV5-4423P | ACACAGGAAGAGACACTCCATTTGCAACTGATTGATCAATGTCTCTTCCTGTGT | C |
| 127 | LASV5S-30X | ACACAGGAAGAGACAAGACAGTACAATAGCCTAGGATCCTGTCTCTTCCTGTGT | C |
| 128 | LASV5S-4423X | ACACAGGAAGAGACACTCCAATGCAACTGATTGTACATTGTCTCTTCCTGTGT | C |
| 129 | LASVP-29X | ACACAGGAAGAGACAAACCTAGGTTCCACAGTGCGCGAATGTCTCTTCCTGTGT | C |
| 130 | LASVP4-29P | ACACAGGAAGAGACAATCCTAGGATCCACTGTGCGCGAATGTCTCTTCCTGTGT | C |
| 131 | Let-7a-5p-P | ACACAGGAAGAGACAAACTATACAACCTACTACCTCATGTCTCTTCCTGTGT | C |
| 132 | Mir-10b-3p | ACACAGGAAGAGACAACAGATTCGATTCTAGGGGAATTGTCTCTTCCTGTGT | C |
| 133 | Mir-125b-3p-P | ACACAGGAAGAGACAAGCTCCCAAGAGCCTAACCCGTTGTCTCTTCCTGTGT | C |
| 134 | Mir-125b-5p-P | ACACAGGAAGAGACATCACAAGTTAGGGTCTCAGGGATGTCTCTTCCTGTGT | C |
| 135 | Mir-126-3p-P | ACACAGGAAGAGACACGCATTATTACTCACGGTACGATGTCTCTTCCTGTGT | C |
| 136 | Mir-126-5p-P | ACACAGGAAGAGACACGCGTACCAAAAGTAATAATGTGTCTCTTCCTGTGT | C |
| 137 | Mir-144-5p | ACACAGGAAGAGACAGGATATCATCATATACTGTAAGTGTCTCTTCCTGTGT | C |
| 138 | Mir-155-3p-P | ACACAGGAAGAGACATGTTAATGCTAATATGTAGGAGTGTCTCTTCCTGTGT | C |
| 139 | Mir-155-5p-P | ACACAGGAAGAGACAACCCCTATCACGATTAGCATTAATGTCTCTTCCTGTGT | C |
| 140 | Mir-16-3p | ACACAGGAAGAGACACCAGTATTAACTGTGCTGCTGATGTCTCTTCCTGTGT | C |
| 141 | Mir-16-5p | ACACAGGAAGAGACATAGCAGCACGTAAATATTGGCGTGTCTCTTCCTGTGT | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 142 | Mir-17-5p | ACACAGGAAGAGACACAAAGTGCTTACAGTGCAGGTAGTGTCTCTTCCTGTGT | C |
| 143 | Mir-183-3p-P | ACACAGGAAGAGACATTATGGCCCTTCGGTAATTCACTGTCTCTTCCTGTGT | C |
| 144 | Mir-183-5p-P | ACACAGGAAGAGACAAGTGAATTCTACCAGTGCCATATGTCTCTTCCTGTGT | C |
| 145 | Mir-191-3p | ACACAGGAAGAGACACAACGGAATCCCAAAAGCAGCTGTGTCTCTTCCTGTGT | C |
| 146 | Mir-191-5p | ACACAGGAAGAGACACAACGGAATCCCAAAAGCAGCTGTGTCTCTTCCTGTGT | C |
| 147 | Mir-21-3p-P | ACACAGGAAGAGACAACAGCCCATCGACTGGTGTTGTGTCTCTTCCTGTGT | C |
| 148 | Mir-21-5p-P | ACACAGGAAGAGACATCAACATCAGTCTGATAAGCTATGTCTCTTCCTGTGT | C |
| 149 | Mir-24-5p | ACACAGGAAGAGACATGCCTACTGAGCTGATATCAGTTGTCTCTTCCTGTGT | C |
| 150 | Mir-26b-3p | ACACAGGAAGAGACATGGCTCAGTTCAGCAGGAACAGTGTCTCTTCCTGTGT | C |
| 151 | Mir-26b-5p | ACACAGGAAGAGACACCTGTTCTCCATTACTTGGCTCTGTCTCTTCCTGTGT | C |
| 152 | Mir-27b-5p | ACACAGGAAGAGACAAGAGCTTAGCTGATTGGTGAACTGTCTCTTCCTGTGT | C |
| 153 | Mir-31-5p | ACACAGGAAGAGACAAGGCAAGATGCTGGCATAGCTTGTCTCTTCCTGTGT | C |
| 154 | Mir-4739-5p | ACACAGGAAGAGACAAAGGGAGGAGGAGCGGAGGGGCCCTTGTCTCTTCCTGTGT | C |
| 155 | Mir-940-5p | ACACAGGAAGAGACAAAGGCAGGGCCCCCGCTCCCCTGTCTCTTCCTGTGT | C |
| 156 | Mir-96-3p-P | ACACAGGAAGAGACACATATTGGCACTGCACATGATTTGTCTCTTCCTGTGT | C |
| 157 | Mir-96-5p-P | ACACAGGAAGAGACAAGCAAAAATGTGCTAGTGCCAAATGTCTCTTCCTGTGT | C |
| 158 | Mm16S-1240PR | ACACAGGAAGAGACATCGCTTCCCTTTGTATACGCCATTTGTCTCTTCCTGTGT | C |
| 159 | Mm23S-1440PR | ACACAGGAAGAGACACGTCGCCCGGATGATTTAGCTTTCTTGTCTCTTCCTGTGT | C |
| 160 | Neg1 | ACACAGGAAGAGACATGaTAGAAcAAATAACCGGaTcGcTGTCTCTTCCTGTGT | C |
| 161 | Pa16S-583PR | ACACAGGAAGAGACAGGGATTTCACATCCAACTTGCTGATGTCTCTTCCTGTGT | C |
| 162 | Pa23S-48PR | ACACAGGAAGAGACAGCTACCACGTCTTTCATCGCCTCTTGTCTCTTCCTGTGT | C |
| 163 | Pm16S-578PR | ACACAGGAAGAGACATGACTTAATTGACCGCCTGCGTGCTGTCTCTTCCTGTGT | C |
| 164 | Pm23S-2565PR | ACACAGGAAGAGACACATGCTTAGCCAACCTTCGTGCTCTGTCTCTTCCTGTGT | C |
| 165 | Pm23S-297PR | ACACAGGAAGAGACAACTTTCCAGACCGTTCTCCTGACATGTCTCTTCCTGTGT | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 166 | Pos2 | ACACAGGAAGAGACATAGTACACCACGCACCAATTACATTGTCTCTTCCTGTGT | C |
| 167 | Rt16-788 | ACACAGGAAGAGACAAAGAGAATCCTCCGATATCTAGCACTGTCTCTTCCTGTGT | C |
| 168 | Rt16-788X | ACACAGGAAGAGACAAAGACAATCCCTCGATATCTAGCACTGTCTCTTCCTGTGT | C |
| 169 | Rt16-949 | ACACAGGAAGAGACAAATCCATAACCACCATGTCAAGGGTGTCTCTTCCTGTGT | C |
| 170 | Rt16-949X | ACACAGGAAGAGACAAATCCATAACCACCATGGCAACGGTGTCTCTTCCTGTGT | C |
| 171 | Rt23S-1216 | ACACAGGAAGAGACACTCCAGCAAACCTTACAGTTTACCTGTCTCTTCCTGTGT | C |
| 172 | Rt23S-1216X | ACACAGGAAGAGACACTCCAGCTTACCTATCAGTAAACCTGTCTCTTCCTGTGT | C |
| 173 | Rt23S-1613 | ACACAGGAAGAGACACACCTGCACATGGTTGCCCACACGTGTCTCTTCCTGTGT | C |
| 174 | Rt23S-1613X | ACACAGGAAGAGACACACCAGCACTAGGTTGCCCACACGTGTCTCTTCCTGTGT | C |
| 175 | Rt23S-301 | ACACAGGAAGAGACATATCACCCTCTATGGTCAATCTTTTGTCTCTTCCTGTGT | C |
| 176 | Rt23S-301X | ACACAGGAAGAGACATATCTCCCTCAATGGACAATCTTTTGTCTCTTCCTGTGT | C |
| 177 | Rt23S-539 | ACACAGGAAGAGACAAAGGTACGCCGTCACAAGACATAATGTCTCTTCCTGTGT | C |
| 178 | Rt23S-539X | ACACAGGAAGAGACAAAGGTACGCCGACACTAGTCATAATGTCTCTTCCTGTGT | C |
| 179 | Rt23S-698 | ACACAGGAAGAGACACAGCGGATTTTACTCCACTTTCAATGTCTCTTCCTGTGT | C |
| 180 | Rt235-698X | ACACAGGAAGAGACACAGCGGTTTTATCACCACTTTCAATGTCTCTTCCTGTGT | C |
| 181 | SaileS2 | ACACAGGAAGAGACACCATTCGCCACGGTCACGAACCATTGTCTCTTCCTGTGT | C |
| 182 | SalexA1 | ACACAGGAAGAGACATGGAAGAAACGATTCATGTGCCAGTTGTCTCTTCCTGTGT | C |
| 183 | SamecA1-1 15 | ACACAGGAAGAGACAGTTCTGCAGTACCGGATTTGCCAATGTCTCTTCCTGTGT | C |
| 184 | SappnK1 | ACACAGGAAGAGACATCGCCTCTAAATCGCTCAAAGTGTTGTCTCTTCCTGTGT | C |
| 185 | SapurK1-1 15 | ACACAGGAAGAGACAAGCTGACCACCACCAATAATGCCATGTCTCTTCCTGTGT | C |
| 186 | SapyrR1 | ACACAGGAAGAGACAAGTGAAGCACGAACCGTTCGACCATGTCTCTTCCTGTGT | C |
| 187 | SarecA1 | ACACAGGAAGAGACATAAATGCTGCCACCCCGCCATTACTGTCTCTTCCTGTGT | C |
| 188 | Sau200 | ACACAGGAAGAGACAGCAAGACCGTCTTTCACTTTTGAATGTCTCTTCCTGTGT | C |
| 189 | Sau236 | ACACAGGAAGAGACAACTAGCTAATGCAGCGCGGATCCATGTCTCTTCCTGTGT | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 190 | Sau453-1 15 | ACACAGGAAGAGACAGTTACTTACACATATGTTCTTC CCTGTCTCTTCCTGTGT | C |
| 191 | Yp16-1004 | ACACAGGAAGAGACACACTTTAGCATCTCTGCCAAAT TCTGTCTCTTCCTGTGT | C |
| 192 | Yp16-1004X | ACACAGGAAGAGACACACAATAGCATCTCTGCCATTT TCTGTCTCTTCCTGTGT | C |
| 193 | Yp16-1240 | ACACAGGAAGAGACATTCGCTTCACTTTGTATCTGCC ATTGTCTCTTCCTGTGT | C |
| 194 | Yp16-1240X | ACACAGGAAGAGACATTCGCTTCTCTCTGTTTCTGCC ATTGTCTCTTCCTGTGT | C |
| 195 | Yp16-1277 | ACACAGGAAGAGACATACGACAGACTTTATGTGGTCC GCTGTCTCTTCCTGTGT | C |
| 196 | Yp16-1277X | ACACAGGAAGAGACATACGACAGTCTTAATGAGGTCC GCTGTCTCTTCCTGTGT | C |
| 197 | Yp16-462 | ACACAGGAAGAGACACGTCAATGATTGAGCGTATTAA ACTGTCTCTTCCTGTGT | C |
| 198 | Yp16-462X | ACACAGGAAGAGACACGTCAATGATTGAGCGAATATA ACTGTCTCTTCCTGTGT | C |
| 199 | Yp23-100 | ACACAGGAAGAGACAGGTATCGTCGGTTATAACGCTT CATGTCTCTTCCTGTGT | C |
| 200 | Yp23-100X | ACACAGGAAGAGACAGGTATCGACGGTAATATCGCTT CATGTCTCTTCCTGTGT | C |
| 201 | Yp23-1490 | ACACAGGAAGAGACAAAGCAACCGGATTTACCTGGTC ACTGTCTCTTCCTGTGT | C |
| 202 | Yp23-1490X | ACACAGGAAGAGACAAAGCAACCGGTATATCCTGGTC ACTGTCTCTTCCTGTGT | C |
| 203 | Yp23-1541 | ACACAGGAAGAGACAATCAACTGCTTCTGCACCGTGG TGTGTCTCTTCCTGTGT | C |
| 204 | Yp23-1541X | ACACAGGAAGAGACAATCTACTGCTCTTGCACCGAGG TGTGTCTCTTCCTGTGT | C |
| 205 | Yp23-1718 | ACACAGGAAGAGACAAGCTAGTCCTTTCACCTAACGC CATGTCTCTTCCTGTGT | C |
| 206 | Yp23-1718X | ACACAGGAAGAGACAAGCTAGTCTCTTAACCTAACGC CATGTCTCTTCCTGTGT | C |
| 207 | Yp23-2865 | ACACAGGAAGAGACACTGGTTAGCTCAATACATCGCT GCTGTCTCTTCCTGTGT | C |
| 208 | Yp23-2865X | ACACAGGAAGAGACACTGGATTGCTCAATTCATCGCT GCTGTCTCTTCCTGTGT | C |
| 209 | ZEBO-301 | ACACAGGAAGAGACACATCAGCCGTTGGATTTGCTAA GCTGTCTCTTCCTGTGT | C |
| 210 | ZEBO-351 | ACACAGGAAGAGACAGATGACAGGTGGAGCAGCATCT TGTGTCTCTTCCTGTGT | C |
| 211 | ZEBO-401 | ACACAGGAAGAGACAGCCTTGCCGAAATGGGTGATAG TATGTCTCTTCCTGTGT | C |
| 212 | ZEBO-GP1 | ACACAGGAAGAGACAGTGCACTTGAACCATTGCAGAG GATGTCTCTTCCTGTGT | C |
| 213 | ZEBO-NP1 | ACACAGGAAGAGACACCACTAGATACTGCTGGCAGCA ATTGTCTCTTCCTGTGT | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 214 | ZKV-131P | ACACAGGAAGAGACACATATTGACAATCCGGAATCCT CCTGTCTCTTCCTGTGT | C |
| 215 | ZKV-131X | ACACAGGAAGAGACACATATTGACAATCCGGTACTCA CCTGTCTCTTCCTGTGT | C |
| 216 | ZKV-2157P | ACACAGGAAGAGACATGTGCCAGTGGTGGGTGATCTT CTTGTCTCTTCCTGTGT | C |
| 217 | ZKV-2157X | ACACAGGAAGAGACATGTGCCAGTGGTGGGTATGCTT CTTGTCTCTTCCTGTGT | C |
| 218 | ZKV-2253P | ACACAGGAAGAGACACTGATCCAAAGTCCCAGGCTGT GTTGTCTCTTCCTGTGT | C |
| 219 | ZKV-239P | ACACAGGAAGAGACAAGGCTAGAATCGCCAAGACCAT CCTGTCTCTTCCTGTGT | C |
| 220 | ZKV-239X | ACACAGGAAGAGACAAGCCTAGATACGGCAAGACCAT CCTGTCTCTTCCTGTGT | C |
| 221 | ZKV-360P | ACACAGGAAGAGACACTCAGCATGGCAGCCAGATCTT TCTGTCTCTTCCTGTGT | C |
| 222 | ZKV-360X | ACACAGGAAGAGACACACAGCATGGGACCCAGATCTT TCTGTCTCTTCCTGTGT | C |
| 223 | ZKV-3990P | ACACAGGAAGAGACACAGCCAGGATTGCCAAGGTGAT GTTGTCTCTTCCTGTGT | C |
| 224 | ZKV-3990X | ACACAGGAAGAGACACTGCCAGGATAGCCAAGGTGAA GTTGTCTCTTCCTGTGT | C |
| 225 | ZKV-661P | ACACAGGAAGAGACAGTGTTGCACCAACAATCGACGT CATGTCTCTTCCTGTGT | C |
| 226 | ZKV-673P | ACACAGGAAGAGACACAAGTTGACGTCGTGTTGCACC AATGTCTCTTCCTGTGT | C |
| 227 | ZKV-730P | ACACAGGAAGAGACAGCTCTTCTAGATCTCCGTGCTT CATGTCTCTTCCTGTGT | C |
| 228 | ZKV-730X | ACACAGGAAGAGACAGCTCTTCATGATCTCCCTGCTC TATGTCTCTTCCTGTGT | C |
| 229 | Ec16S-1283 | ACA CAG GAA GAG ACA ATC CGG ACT ACG ACG CAC TTT ATG TGT CTC TTC CTG TGT | C |
| 230 | Ec23S-2722 | ACA CAG GAA GAG ACA CAT CTC GGG GCA AGT TTC GTG CTT TGT CTC TTC CTG TGT | C |
| 231 | Ec23S-1585 | ACA CAG GAA GAG ACA TTG ATG TTA CCT GAT GCT TAG AGG CTG TCT CTT CCT GTG T | C |
| 232 | Ec23S-511 | ACA CAG GAA GAG ACA TGT ACG TAC ACG GTT TCA GGT TCT TGT CTC TTC CTG TGT | C |
| 233 | Pa16S-481 | ACA CAG GAA GAG ACA AGT TAG CCG GTG CTT ATT CTG TTG TGT CTC TTC CTG TGT | C |
| 234 | Pa16S-1411 | ACA CAG GAA GAG ACA GCT ACC ACG TCT TTC ATC GCC TCT TGT CTC TTC CTG TGT | C |
| 235 | Pa23S-47 | ACA CAG GAA GAG ACA ACA CGC ACA GTG GAT CCT AGG CAA TGT CTC TTC CTG TGT | C |
| 236 | Pa23S-1006 | ACA CAG GAA GAG ACA CAT CGT TTA CCA CTT AAC CAC AAC TGT CTC TTC CTG TGT | C |
| 237 | Pa23S-278 | ACACAGGAAGAGACA GTTCCGCTAAAATCAATGAAGCTT TGTCTCTTCCTGTGT | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 238 | Pa23S-1136 | ACACAGGAAGAGACA A GCAGCTTCGGTGTGTGGTTTGAG TGTCTCTTCCTGTGT | C |
| 239 | Pa23S-1389 | ACACAGGAAGAGACA CATCGCAGTAACCAGAAGTACAGGAA TGTCTCTTCCTGTGT | C |
| 240 | Pm16S-578 | ACA CAG GAA GAG ACA TGA CTT AAT TGA CCG CCT GCG TGC TGT CTC TTC CTG TGT | C |
| 241 | Pm16S-985 | ACA CAG GAA GAG ACA GGA TTC GCT GGA TGT CAA GAG TAG TGT CTC TTC CTG TGT | C |
| 242 | Pm23S-2493 | ACA CAG GAA GAG ACA CAC GGT CCC CGA CCC AGT TTA TGA TGT CTC TTC CTG TGT | C |
| 243 | Pm23S-297 | ACACAGGAAGAGACA ACTTTCCAGACCGTTCTCCTGACA TGTCTCTTCCTGTGT | C |
| 244 | Pm23S-1987 | ACACAGGAAGAGACA G GGACTTTACCTACCGCCAGCGT A TGTCTCTTCCTGTGT | C |
| 245 | Pm23S-3177 | ACACAGGAAGAGACA TTCGGTGTTGTCAGGTTAAGCCTC TGTCTCTTCCTGTGT | C |
| 246 | Kp16S-216PR | ACA CAG GAA GAG ACA TCT GGG CAC ATC TGA TGG CAT GAG TGT CTC TTC CTG TGT | C |
| 247 | Kp16S-986P | ACA CAG GAA GAG ACA AAG TTC TGT GGA TGT CAA GAC CAG TGT CTC TTC CTG TGT | C |
| 248 | Kp23S-71P | ACA CAG GAA GAG ACA CCT TAC CGA CGC TTT TCG CAG ATT TGT CTC TTC CTG TGT | C |
| 249 | Kp23S-290 | ACA CAG GAA GAG ACA GAC CGT TCC ACT AAC ACA CAA GCT TGT CTC TTC CTG TGT | C |
| 250 | Kp23s-1746 | ACACAGGAAGAGAC A CTGGTATCTTCGACTGGTCTCAGC TGTCTCTTCCTGTGT | C |
| 251 | Kp23s-2345 | ACACAGGAAGAGACA C CACGCTCGCAGTCAAGCTAGCTT TGTCTCTTCCTGTGT | C |
| 252 | Mm16S-216 | ACACAGGAAGAGACA TATGGGTTCATCTGATGGCGCGAG TGTCTCTTCCTGTGT | C |
| 253 | Mm16S-581 | ACACAGGAAGAGACA ATCTGACTCAATCAACCGCCTGCG TGTCTCTTCCTGTGT | C |
| 254 | Mm23S-15 | ACACAGGAAGAGACA CATCCACCGTGTACGCTTATTCGC TGTCTCTTCCTGTGT | C |
| 255 | Mm23S-172 | ACACAGGAAGAGACA CTCCCGGTTCGCTTCATTACCCTA TGTCTCTTCCTGTGT | C |
| 256 | Mm23S-1557 | ACACAGGAAGAGACA TCCCGGAAGCAGAGCATCAATCAC TGTCTCTTCCTGTGT | C |
| 257 | Sa16S-431 | ACACAGGAAGAGAC A TATGTTCTTCCCTAATAACAGAGT T GTCTCTTCCTGTGTC | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 258 | Sa16S-989 | ACACAGGAAGAGACA CTAGAGTTGTCAAAGGATGTCAAGA T GTCTCTTCCTGTGT | C |
| 259 | Sau23s-397 | ACACAGGAAGAGACA AGGATCCACTCAAGAGAGACAACA TGTCTCTTCCTGTGT | C |
| 260 | Sau23s-1699 | ACACAGGAAGAGACA TTCCTTAACGAGAGTTCGCTCGCT TGTCTCTTCCTGTGT | C |
| 261 | Sau23s-2125 | ACACAGGAAGAGA CA AGCTGTGCCGAATTTCAATATCAG TGTCTCTTCCTGTGT | C |
| 262 | Efs16s-1300 | ACA CAG GAA GAG ACA GCA ATC CGA ACT GAG AGA AGC TTT TGT CTC TTC CTG TGT | C |
| 263 | Efs16s-465 | ACA CAG GAA GAG ACA CGT TCA GTT ACT AAC GTC CTT GTT TGT CTC TTC CTG TGT | C |
| 264 | Efs23S-1189 | ACA CAG GAA GAG ACA ATG GTG TAG TCC ACA GCT TCG GTA TGT CTC TTC CTG TGT | C |
| 265 | Efs23S-540 | ACACAGGAAGAGACA TAGGCACACGGTTTCAGGATCTAT T GTCTCTTCCTGTGT | C |
| 266 | Efs23S-94 | ACACAGGAAGAGAC A TTCGGAAATCTCTGGATCATAGCT T GTCTCTTCCTGTGT | C |
| 267 | Sag16S-70 | ACACAGGAAGAGA CA ACTCATCAGTCTAGTGTAAACACC TGTCTCTTCCTGTGT | C |
| 268 | Sag16S-449 | ACACAGGAAGAGACA GTAGATTTTCCACTCCTACCAACG T GTCTCTTCCTGTGT | C |
| 269 | Sag16S-638 | ACACAGGAAGAGACA CCTTCTGCACTCAAGTCCTCCAGT T GTCTCTTCCTGTGT | C |
| 270 | Sag16S-1019 | ACACAGGAAGAGA CA CTTCTGCTCCGAAGAGAAAGCCTA TGTCTCTTCCTGTGT | C |
| 271 | Sag23S-379 | ACACAGGAAGAGAC A CTCAGGATACTGCTAAGGTTAATC T GTCTCTTCCTGTGT | C |
| 272 | Sag23S-957 | ACACAGGAAGAGACA AGTCTGACTGCCGATTATATCTCG T GTCTCTTCCTGTGT | C |
| 273 | Sag23S-1545 | ACACAGGAAGAGACA ACTTCGCTCCTCGTCACAGCTCAA TGTCTCTTCCTGTGT | C |
| 274 | Sag23S-2847 | ACACAGGAAGAGACA TGTCACCACAATTACACTCCTAAC TGTCTCTTCCTGTGT | C |
| 275 | Cspec18S-1088P | ACA CAG GAA GAG ACA GAA CCC AAA GAC TTT GAT TTC TCG TGT CTC TTC CTG TGT | C |
| 276 | Cspec18S-837 | ACA CAG GAA GAG ACA ATT ACG ATG GTC CTA GAA ACC AAC TGT CTC TTC CTG TGT | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 277 | Cspec23S-338 | ACACAGGAAGAGA CA TCACTGTACTTGTTCGCTATCGGT TGTCTCTTCCTGTGT | C |
| 278 | Cspec23S-1155 | ACACAGGAAGAGA CA TTCCGGCACTTTAACTTCACGTTC TGTCTCTTCCTGTGT | C |
| 279 | Cspec23S-1697 | ACACAGGAAGAG ACA TAAACCAATTCCAGGGTGATAAGC T GTCTCTTCCTGTGT | C |
| 280 | Cspec23S-2073 | ACACAGGAAGAGACA TCCGTACCAGTTCTAAGTTGATCG T GTCTCTTCCTGTGT | C |
| 281 | Cspec23S-3087 | ACACAGGAAGAGAC A GCATGGATTCTGACTTAGAGGCGTT TGTCTCTTCCTGTGT | C |
| 282 | Ec16S-514 | ACACAGGAAGAGACA CAT TTACCGCGGCTGCTGGCACG A TGTCTCTTCCTGTGT | C |
| 283 | Ec16S-791 | ACACAGGAAGAGACA GCGTGGACTACCAGGGTATC AAAA TGTCTCTTCCTGTGT | C |
| 284 | Ec16S-932 | ACACAGGAAGAGACA ATT CATGCTCCACCGCTTGTGCG A TGTCTCTTCCTGTGT | C |
| 285 | Ec23S-1930 | ACACAGGAAGAGAC A CTTACCCGACAAGGAATTTCGCTA TGTCTCTTCCTGTGTC | C |
| 286 | Ec23S-2490 | ACACAGGAAGAGACAA GAGCCGACATCGAGGTGCCAAAC TGTCTCTTCCTGTGT | C |
| 287 | UN17-16S-519 | ACA CAG GAA GAG ACA AAC CGT ATT ACC GCG GCT GCT GAA TGT CTC TTC CTG TGT | C |
| 288 | UN18-16S-1062 | ACA CAG GAA GAG ACA CAT TTC ACA ACA CGA GCT GAC ATC TGT CTC TTC CTG TGT | C |
| 289 | Yp16S-1240 | ACA CAG GAA GAG ACA TTC GCT TCA CTT TGT ATC TGC CAT TGT CTC TTC CTG TGT | C |
| 290 | Yp23S-100 | ACA CAG GAA GAG ACA GGT ATC GTC GGT TAT AAC GCT TCA TGT CTC TTC CTG TGT | C |
| 291 | Yp23S-272 | ACA CAG GAA GAG ACA CAC AAA CTG ATT CAG ACT CTG GGC TGT CTC TTC CTG TGT | C |
| 292 | Yp23S-1435 | ACA CAG GAA GAG ACA TTG GCC AGC CTA GCC TTC TCC GAT TGT CTC TTC CTG TGT | C |
| 293 | Yp23S-356 | ACA CAG GAA GAG ACA CTC ATC GAG TTC ACA GCC TGT GCA TGT CTC TTC CTG TGT | C |
| 294 | Rt23S-991 | ACA CAG GAA GAG ACA GTC ATG ATT TAG GGA CCT TAG ATG TGT CTC TTC CTG TGT | C |
| 295 | Rt23S-1142 | ACA CAG GAA GAG ACA CCG CAT CTT CGG TAC ATG ACT TGA TGT CTC TTC CTG TGT | C |
| 296 | Rt23S-1397 | ACA CAG GAA GAG ACA CGT CAC ATC CTT TAG GTT CAG GAA TGT CTC TTC CTG TGT | C |
| 297 | Rt23S-1953 | ACA CAG GAA GAG ACA ACT TCT AAC ACC AGT GCA AAG CTA TGT CTC TTC CTG TGT | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 298 | Rt16S-33 | ACA CAG GAA GAG ACA AGC ATA CCG ATA GCG TTC GTT CTG TGT CTC TTC CTG TGT | C |
| 299 | Rt23S-1109 | ACA CAG GAA GAG ACA CAT TGT TGG CGC AAG AAA ACT TAT TGT CTC TTC CTG TGT | C |
| 300 | Rt23S-1865 | ACA CAG GAA GAG ACA TTT CGC TGA GTC GAT ACT GGA GAC TGT CTC TTC CTG TGT | C |
| 301 | Rt23S-2030 | ACA CAG GAA GAG ACA AGG GTG GTA TCT CAA GAG TGA CTC TGT CTC TTC CTG TGT | C |
| 302 | CKV-2658 | ACACAGGAAGAGACAGTGCGCATTTTGCCTTCGTAAT GATGTCTCTTCCTGTGT | C |
| 303 | CKV-6705 | ACACAGGAAGAGACAAGTCCTCGGCAGACATGTCAAA CATGTCTCTTCCTGTGT | C |
| 304 | CKV-7335 | ACACAGGAAGAGACATTAGCCCTGTTCGTTGCCATCT CCTGTCTCTTCCTGTGT | C |
| 305 | CKV-10028 | ACACAGGAAGAGACAAGAGTCTTATACGGTACTCCCA CCTGTCTCTTCCTGTGT | C |
| 306 | CKV-10575 | ACACAGGAAGAGACAAATTGTCCTGGTCTTCCTGCGC CGTGTCTCTTCCTGTGT | C |
| 307 | CKV-10695 | ACACAGGAAGAGACACAAGCCAGATGGTGCCTGAGAG TATGTCTCTTCCTGTGT | C |
| 308 | DV2-2188-2 | ACACAGGAAGAGACA C GCTGTGTCACCTAAAATGGCCA A TGTCTCTTCCTGTGT | C |
| 309 | DV23-8572 | ACACAGGAAGAGACA TCTGTCATTGCCATCTGTGTCACC TGTCTCTTCCTGTGT | C |
| 310 | DV1-7819 | ACACAGGAAGAGACA TATGACCAGCCACCTCTTCCACA C TGTCTCTTCCTGTGT | C |
| 311 | DV1-9862 | ACACAGGAAGAGACA GTCTCTCCTGTGGAAGTACATCAG TGTCTCTTCCTGTGT | C |
| 312 | DV34-10322 | ACACAGGAAGAGACA ACTACAGGCAGCACGGTTTGCTCA TGTCTCTTCCTGTGT | C |
| 313 | DV4-38 | ACACAGGAAGAGACA GAACTGTGTTAAGCAAGCTTCCGA TGTCTCTTCCTGTGT | C |
| 314 | DV1-10487 | ACA CAG GAA GAG ACA CTG CTA CCC CAT GCG TAC AGC TTC TGT CTC TTC CTG TGT | C |
| 315 | DV2-202 | ACA CAG GAA GAG ACA GCA TTC CAA GTG AGA ATC TCT TTG TGT CTC TTC CTG TGT | C |
| 316 | DV2-1891 | ACA CAG GAA GAG ACA AAC TAT TGT TCC ATG TTG TGT TTC TGT CTC TTC CTG TGT | C |
| 317 | DV2-4805 | ACA CAG GAA GAG ACA ACC TGG ACT TCT TCT CCT TCC TTC TGT CTC TTC CTG TGT | C |
| 318 | DV13-6255 | ACA CAG GAA GAG ACA TTT CTC CTT CCT TTG TCC AGA TTT TGT CTC TTC CTG TGT | C |
| 319 | DV4-2717 | ACA CAG GAA GAG ACA GGT GTG AGT GCT CTC TTT CCT TTG TGT CTC TTC CTG TGT | C |

TABLE I-continued

List of nucleic acid sequences with SEQ ID NO.

| SEQ ID NO. | Name | Sequence | Captor (C) Target (T) Probe (P) Helper (H) |
|---|---|---|---|
| 320 | DV4-8308 | ACA CAG GAA GAG ACA TCT ACG TCC TTC TCA TAA GTG GGT TGT CTC TTC CTG TGT | C |
| 321 | LAS3-3004 | ACA CAG GAA GAG ACA AGA CGA TCT ACT AAT CCT GGC CGC TGT CTC TTC CTG TGT | C |
| 322 | LAS5-2285 | ACA CAG GAA GAG ACA TCT GTC AGT CTA TCT GGT GTC TCT TGT CTC TTC CTG TGT | C |
| 323 | LAS5-5533 | ACA CAG GAA GAG ACA CTT GAC TAT GTG CGA CAC AAG AGA TGT CTC TTC CTG TGT | C |
| 324 | HEc12-5-1 | TGG AAG CAG GGC ATT TGT YGC TTC AGC ACC | H |
| 325 | HEc12-3-1 | TCT ACC TGA CCA CCT GTG TCG GTT TGG G | H |
| 326 | HEc12-5-2 | TGG AAG CAG GGC ATT TGT YGC TTC A | H |
| 327 | HEc12-3-2 | CTG ACC ACC TGT GTC GGT TTG GG | H |
| 328 | HPa3-5-1 | GTC AAA ACA GCA AGG TAT TAA CTT ACT GCC | H |
| 329 | HPa3-3-1 | CTT GCA CCC TTC GTA TTA CCG CGG CTG CTG | H |
| 330 | HPa3-5-2 | GTC AAA ACA GCA AGG TAT TAA CTT A | H |
| 331 | HPa3-3-2 | ACC CTT CGT ATT ACC GCG GCT GCT G | H |
| 332 | HCspec3-5-1 | AGA ACC ATA ACG TCC TAT TCT ATT ATT CCA | H |
| 333 | HCspec3-3-1 | CTG AAT ACT GAT ACC TCC GAC CGT CCC TAT | H |
| 334 | HCspec3-5-2 | AGA ACC ATA ACG TCC TAT TCT ATT A | H |
| 335 | HCspec3-3-2 | TAC TGA TAC CTC CGA CCG TCC CTA T | H |
| 336 | 15TB | TTTACACAGGAAGAG | P |
| 337 | 13TB | TACACAGGAAGAG | P |
| 338 | 5D3 | CTCTTCCTGTGTA | P |
| 339 | Efs23S-570 | ACA CAG GAA GAG ACA CAT CAC TCA TTA ACG AGC TTT GAC TGT CTC TTC CTG TGT | C |

EXAMPLES

The following examples are put forth so as to provide those of ordinary skill in the art with a complete disclosure and description of how the compounds, compositions, devices, devices and/or methods claimed herein are made and evaluated, and are intended to be purely exemplary of the invention and are not intended to limit the scope of what the present disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

In the following examples, the following buffers were used.

First Hybridization Buffer. The first hybridization buffer was 300 mM sodium chloride (NaCl), 20 mM monosodium phosphate (NaH$_2$PO$_4$), 2 mM EDTA, 10% volume/volume (v/v) ethanol (EtOH) and 0.1% SDS, with a pH adjusted to 7.4 with 6N HCl.

Second Hybridization Buffer. The second hybridization buffer was 300 mM NaCl, 20 mM NaH$_2$PO$_4$, 2 mM EDTA, and 0.1% SDS, with a pH adjusted to 7.4 with 6N HCl.

First Rinse Buffer. The first rinse buffer was 300 mM NaCl, 20 mM NaH$_2$PO$_4$, 2 mM EDTA, 2% v/v EtOH and 0.05% SDS, with a pH adjusted to 7.4 with 6N HCl.

Second Rinse Buffer. The second rinse buffer was 300 mM NaCl, 20 mM NaH$_2$PO4, 2 mM EDTA, and 0.1% SDS, with a pH adjusted to 7.4 with 6N HCl. In the following experiments, a first final rinse buffer consisted of 750 mM NaCl and 75 mM sodium citrate.

First Detection Buffer. The first detection buffer was 300 mM NaCl, 20 mM NaH2PO4, 2 mM EDTA, 0.1% SDS, with a pH adjusted to 7.4 with 6N HCl.

First Lysis Buffer. The first lysis buffer was 20 mM Tris(hydroxymethyl)aminomethane, 2 mM EDTA, 320 mM NaCl and 0.2% SDS.

Example 2

A sample of Escherichia coli (E. coli) bacteria was placed in 750 microliters (μL) of the first lysis buffer with 250 μL of 0.1 millimeter diameter glass-zirconia beads at 95° C. with or without 4 mM zinc chloride (ZnCl2). The solution was vortexed two times for a thirty (30) second interval followed by two (2) minute incubation at 95° C. to fully lyse the bacteria. Lysis was confirmed by plating a portion of the final lysates, and the time interval required for complete lysis was that which resulted in no observed bacterial growth.

A portion of each lysate was also analyzed by a Qubit Fluorometric Concentration determination (ThermoFisher Scientific, Waltham, Mass.) and Agilent Bioanalyzer (Agilent Technologies, Santa Clara, Calif.) by the Genomic Services Laboratory (Huntsville, Ala.) and the size of the extracted RNA compared. In the absence of $ZnCl_2$, the lysate was determined to have an RNA Integrity Number (RIN) (as determined by Agilent Bioanalyzer) of 4.9 to 7.2 and was determined to have intact 16S and 23S RNA peaks. In the presence of $ZnCl_2$, the lysate was determined to have degraded 16S and 23S RNA peaks with the bulk of the RNA in the size range from 50 to 500 nucleotides.

The $ZnCl_2$ digested RNA was used in the disclosed assay with captor molecule Ec632 (SEQ ID NO:1), whose sequence is shown in Table I, targeting the 16S RNA of E. coli. The RNA was hybridized to the captor molecule for twenty (20) minutes using the first hybridization buffer. A rinse step to remove non-specific RNA was performed with the first rinse buffer. The labeled probe 13D (SEQ ID NO:2), see Table I, was added at a concentration of 2 nM for 3.5 minutes in the first detection buffer. After a further rinse with the first rinse buffer and the first final rinse buffer to stabilize any double-stranded regions, the distribution of fluorescence was analyzed using a fluorescent detector, such as GenePix 4200b scanner (Molecular Devices, LLC, Sunnyvale, Calif.). As shown in FIG. 3, concentration dependent relative fluorescent signals, which are noted above each bar, were observed with concentrations of total RNA ranging from A: 0 μg RNA, B: 50 μg RNA, C: 133 μg RNA to D: 246 μg RNA. The error bars represent the standard deviation in the relative signals when sufficient material was available for multiple experiments.

Example 3

In an aspect, the captor molecule E coli 476 was generated with stems with a length 16 (SEQ ID NO:4), 14 (SEQ ID NO:5) and 12 (SEQ ID NO:6) nucleotides (see Table I). Each captor molecule was hybridized for thirty (30) minutes using the second hybridization buffer which contained no target molecules. A rinse step was performed with a second rinse buffer. The labeled probe 16D (SEQ ID NO:7) was then added at a concentration of 20 nM for ten minutes in the first detection buffer. After a further rinse with the second rinse buffer and a final rinse with the first final rinse buffer to stabilize any double-stranded regions, the distribution of fluorescence was analyzed on a commercially available GenePix 4200b scanner. As shown in Table II, the relative background signal measured in the absence of target was greatly reduced as the stem shortened.

TABLE II

Comparison of the Relative Background Signal for Three Differing Stem lengths

| Name | SEQ ID NO | Relative Targetless Signal |
|---|---|---|
| Ecoli476 | 4 | 52 |
| Ecoli476-14 | 5 | 3 |
| Ecoli476-12 | 6 | 1 |

Example 4

Figure 4:
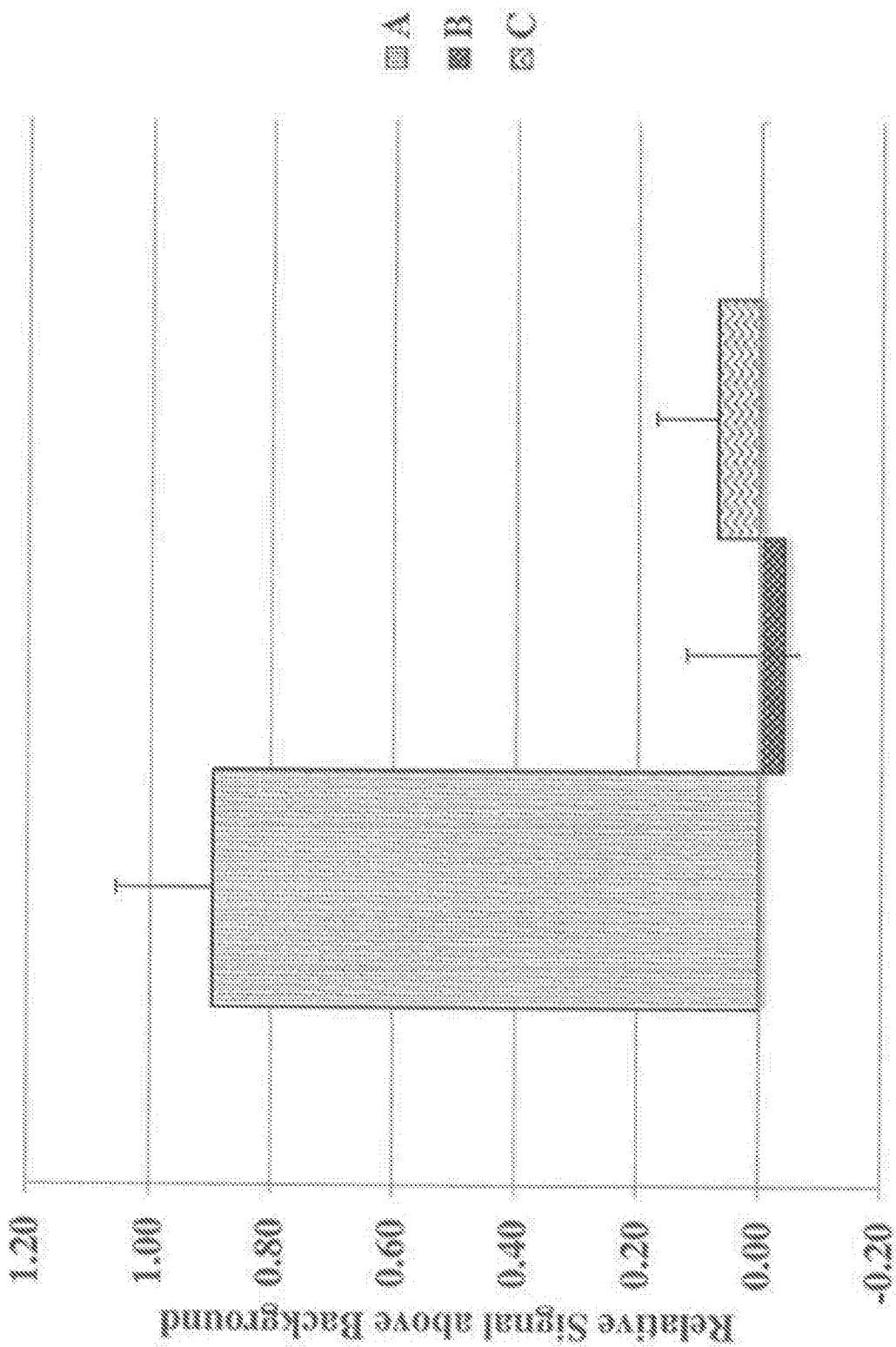
FIG. 4 is a is a graphic representation showing the relative signal of a captor molecule from a variety of targets including a fully complementary target, and two different double-mismatched targets, according to various aspects of the present disclosure.
Figure 5:
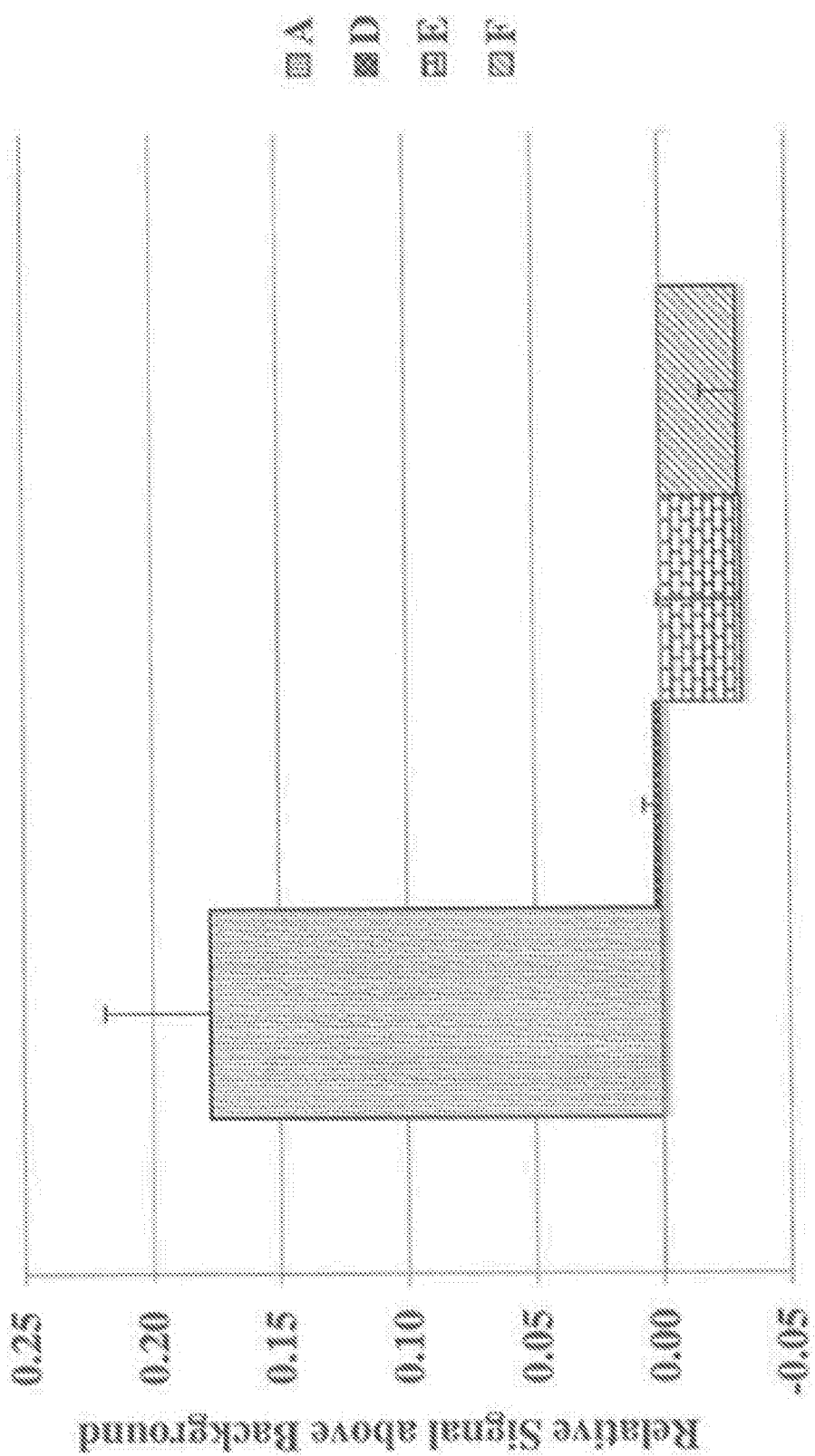
FIG. 5 is a chart showing the relative signal of a captor molecule from a variety of targets including a fully complementary target, a singly-mismatched target and two different truncations of the target, according to various aspects of the present disclosure.

A captor molecule Sau453 mA (SEQ ID NO:8), its fully-complementary DNA target Sau453T (SEQ ID NO:9), its mismatched DNA targets Sau453TC2 (SEQ. ID 10), Sau453TG2 (SEQ. ID 11), and Sau453T14C (SEQ. ID 12) or its truncated DNA targets Sau453T6-27 (SEQ. ID 13) and Sau453T1-22 (SEQ ID NO:14), were used in the following experiments. Each DNA target was hybridized at a concentration of 250 pM or 50 pM to the captor molecule for 20 minutes at 52° C. using the first hybridization buffer. A rinse step to remove non-specific binding was performed with the second rinse buffer. The labeled probe 13D (SEQ ID NO:2) was then added at a concentration of 2 nM for 3.5 minutes in the first detection buffer. After a further rinse with the second rinse buffer and a final rinse with a buffer containing 112.5 mM NaCl and 11 mM sodium citrate to stabilize any double-stranded regions, the distribution of fluorescence was analyzed on a commercially available GenePix 4200b scanner. The assay was performed at 52° C. with 250 pM of (A) the fully-complementary target Sau453T (SEQ ID NO:9), or (B) the double mutant Sau453TC2 (SEQ ID NO:10) (which makes highly unfavorable C-T pairs), or (C) the double mutant Sau453TG2 (SEQ ID NO:11) (which makes less unfavorable G-T pairs). As shown in FIG. 4, the relative signals from both panels B and C were equivalent to no target. As shown in FIG. 5, the assay was also performed at 52° C. with only 50 pM of (A) the fully-complementary target Sau453T (SEQ ID NO:9), or (D) the single mismatch target Sau453T14C (SEQ ID NO:12), or (E) the truncation Sau453T6-27 (SEQ ID NO:13), or (F) the truncation Sau453T1-22 (SEQ ID NO:14). The results also show no significant relative signal above background for panels D, E or F. In FIGS. 4 and 5, the error bars represent the standard deviations from multiple runs under each condition. While it was expected that the unfavorable double mismatch B and the truncations E and F would not bind well to the captor molecule, it was unexpected that the less unfavorable double mismatch C and the single mismatch D would give no significant signal above background.

A temperature curve of relative target binding signal for the fully complementary Sau453T (SEQ ID NO:9) was determined by performing the above hybridization protocol with 250 pM Sau453T (SEQ ID NO:9) at hybridization temperatures of 47, 52, 57, 62, 67 and 72° C. The maximum signal for binding Sau453 mA captor molecule (SEQ ID NO:8) to its fully complementary target was determined to be 52° C. The melting temperature in solution of the captor molecule-target duplex is calculated to be 60.2° C. under hybridization conditions, and the melting temperature of the hairpin structure of the Sau453 mA (SEQ ID NO:8) captor molecule itself is calculated to be 79.9° C. Calculations are based on the models of J SantaLucia Jr and D Hicks, Annu. Rev. Biophys. Biomol. Struct. 24.33:415-40. The maximum binding was realized at 52° C., which is well below both calculated values. Without wishing to be bound by a particular theory, under these conditions the captor molecule is believed to maintain the closed stem-loop structure during the hybridizations, thereby enhancing the stem-loop captor molecule method's ability for single mismatch discrimination. Without wishing to be bound by a particular theory, it is believed that a rapid protocol using a buffer with denaturing properties where the stem-loop structure of the captor molecule must be replaced with the target-captor molecule duplex can increase the specificity of binding to only the fully-complementary target nucleic acid.

Example 5

Figure 6:
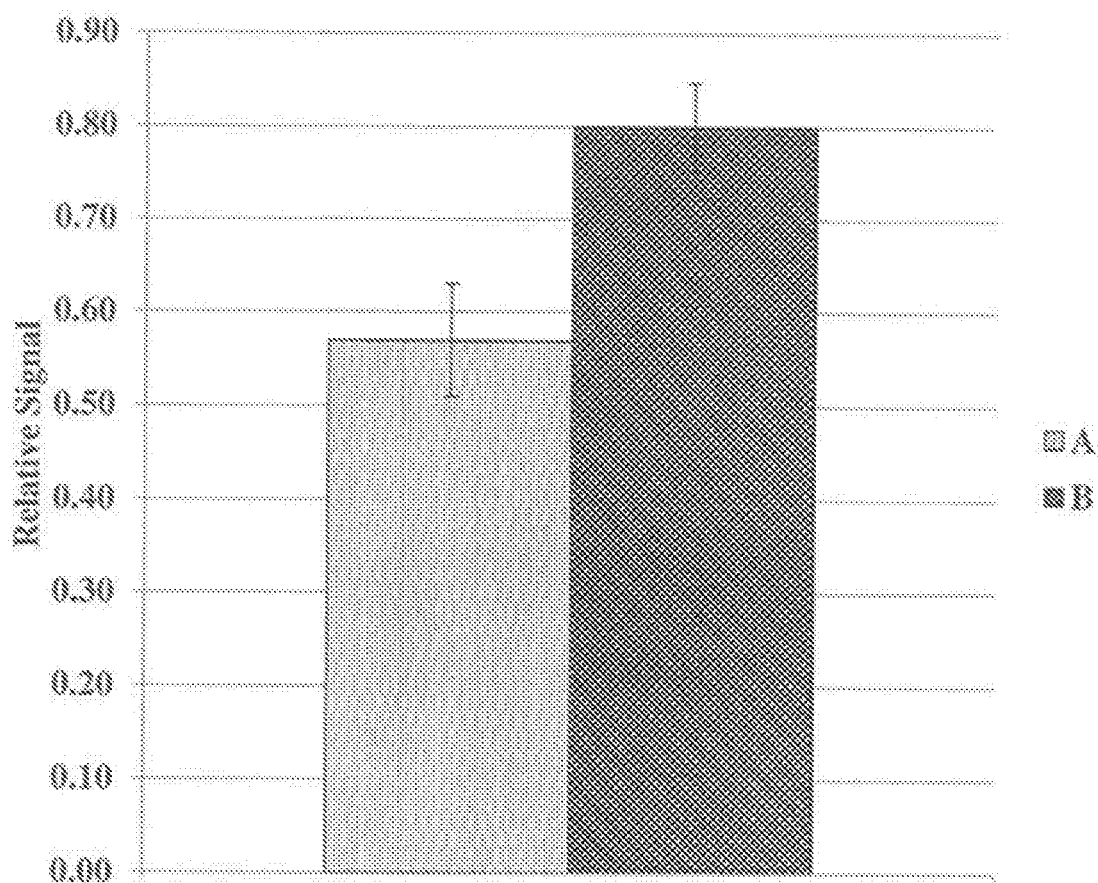
FIG. 6 is a chart showing the improvement in relative signal between hybridization buffers showing the effect of the addition of ethanol, according to various aspects of the present disclosure.

The captor molecule Sau453n (SEQ ID NO:15) was printed onto NSB-27 slides (NSB USA Inc., Los Alamitos, Calif.) at a concentration of 5 µM and was hybridized at 37° C. to its target Sau453T (SEQ ID NO:9) at a concentration of 10 nM for twenty minutes using either the first hybridization buffer (column B in FIG. 6) or the second hybridization buffer (column A in FIG. 6). The slide was rinsed with the second rinse buffer. The labeled probe 11Dn (SEQ ID NO:16) was then added at a concentration of 0.5 nM for two minutes in the first detection buffer. After a further rinse with the second rinse buffer and a final rinse with a buffer containing 9 mM NaCl and 0.9 mM sodium citrate, the distribution of fluorescence was analyzed on a commercially available GenePix 4200b scanner. As shown in FIG. 6, the first hybridization buffer (see column B) containing 10% EtOH gave a stronger signal from the same amount of target compared to what was realized with the no additive (see column A). In FIG. 6, the error bars represent the standard deviations from multiple runs under each condition.

The captor molecule Pos1 (SEQ ID NO:17) was printed onto NSB-27 slides at a concentration of 0.2 µM and was hybridized at 52° C. with its target Pos1T (SEQ ID NO:18) at a concentration of 100 pM for 20 minutes using the second hybridization buffer with varying amounts of DMSO and/or SDS as listed in Table III.

TABLE III

Variations in the Composition of the Second Hybridization Buffer

| 2nd Hybridization Buffer | Concentration of DMSO (M) | Concentration of SDS (wt %) |
|---|---|---|
| A | 1.0 | 0 |
| B | 0.75 | 0 |
| C | 0.5 | 0 |
| D | 0.5 | 0.05 |
| E | 0.375 | 0.05 |
| F | 0.25 | 0.05 |

Figure 7:
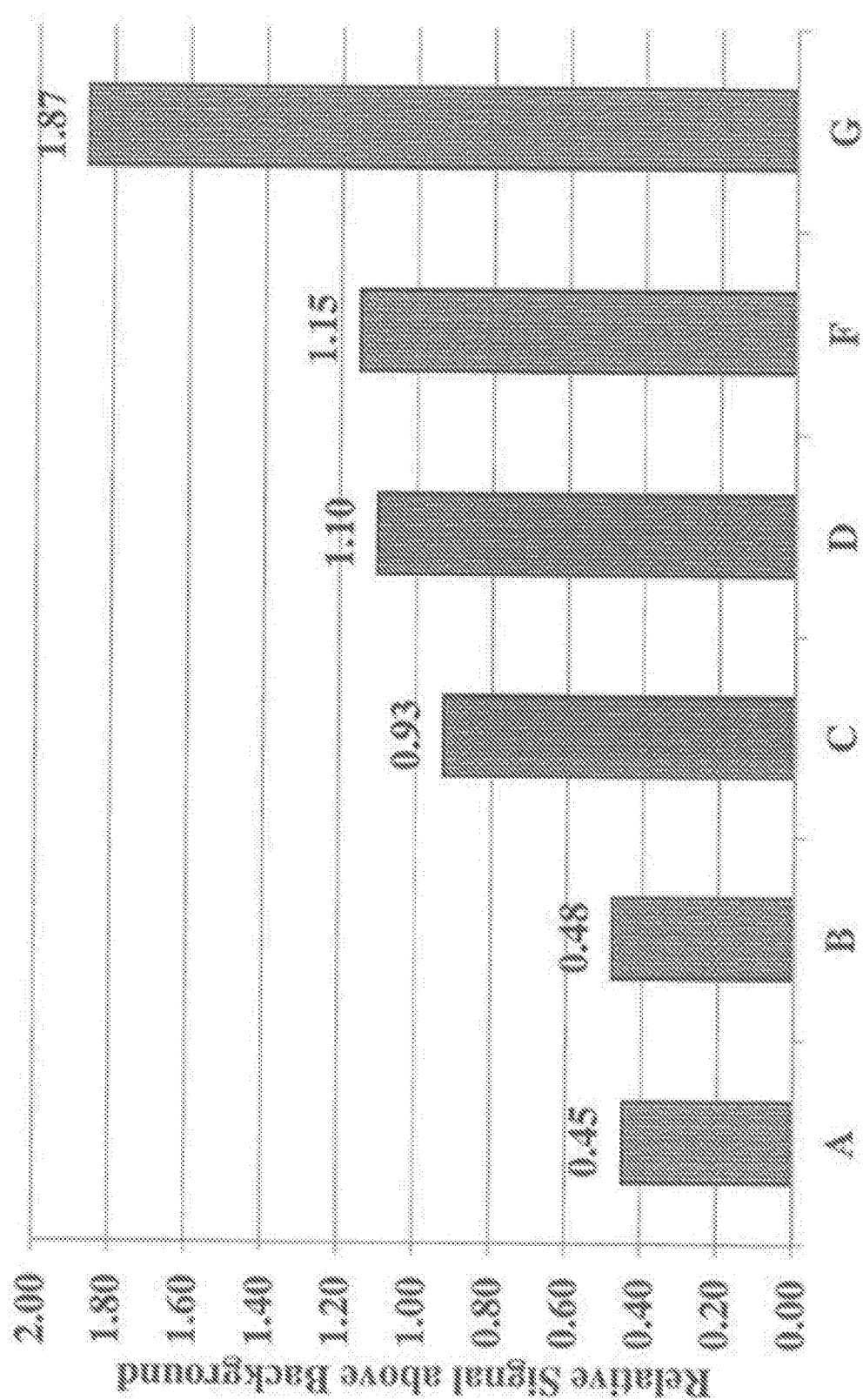
FIG. 7 is a chart showing the relative signal when a constant concentration of 100 picomolar (pM) of nucleic acid target was used in a variety of hybridization buffers, according to various aspects of the present disclosure.

The slide was rinsed with the second rinse buffer. The labeled probe 13D (SEQ ID NO:2), whose sequence is listed in Table I, was then added at 5 nM for 30 seconds in the first detection buffer. After a further rinse with the second rinse buffer and a final rinse with a buffer containing 112.5 mM NaCl and 11 mM sodium citrate, the distribution of fluorescence was analyzed on a commercially available GenePix 4200b scanner. As shown in FIG. 7, the relative signal generated in 20 minutes increases as the amount of denaturing DMSO decreases, but improves upon the addition of SDS. The numbers above each bar represent the relative signal under each condition. One skilled in the art can appreciate that these results are extremely unexpected, i.e., that a denaturing buffer containing ethanol or ionic detergents would improve the relative signal in shorter times.

Example 6

Figure 8:
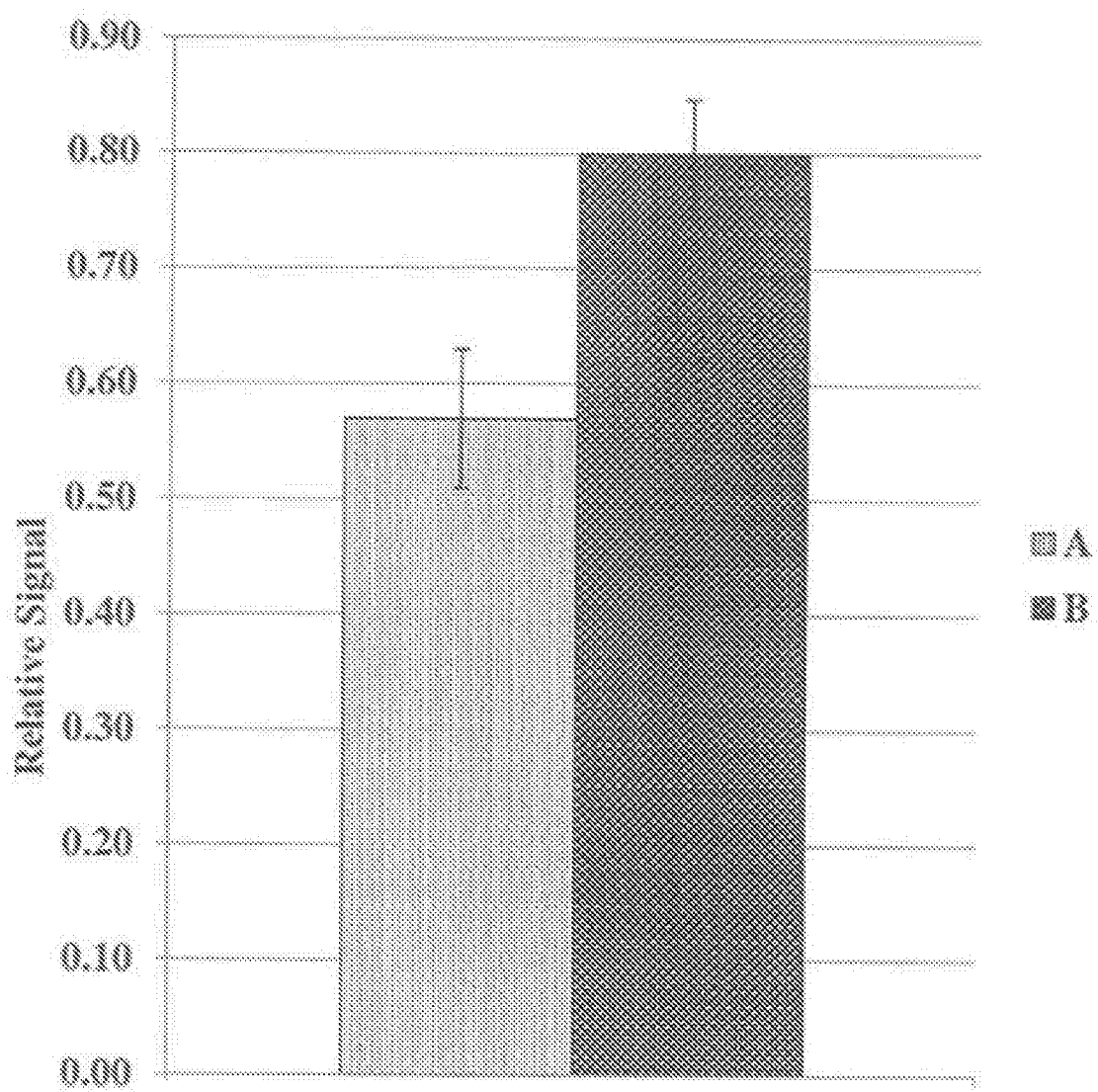
FIG. 8 is a chart showing the relative signal with the presence or absence of target added during the first hybridization, according to various aspects of the present disclosure.

The captor molecule SamecA1 (SEQ ID NO:19) was printed onto NSB-27 slides at a concentration of 0.2 µM and was hybridized at 52° C. to its target SamecA1T (SEQ ID NO:20) for 20 minutes in the first hybridization buffer under the following conditions: (A) to buffer alone; or (B) a concentration of 100 pM. The slide was rinsed with the second rinse buffer. The labeled probe 13D (SEQ ID NO:2) was then added at 23° C. for 30 seconds in the first detection buffer. After a further rinse with the second rinse buffer and a final rinse with a buffer containing 112.5 mM NaCl and 11 mM sodium citrate, the distribution of fluorescence was analyzed on a commercially available GenePix 4200b scanner. As shown in FIG. 8, the low relative background in buffer alone (column A, FIG. 8) provided a distinct signal from only 25 pM of SamecA1 target (SEQ ID NO:19; see column B, FIG. 8). In FIG. 8, the error bars represent the standard deviations from multiple runs under each condition.

Example 7

Figure 9:
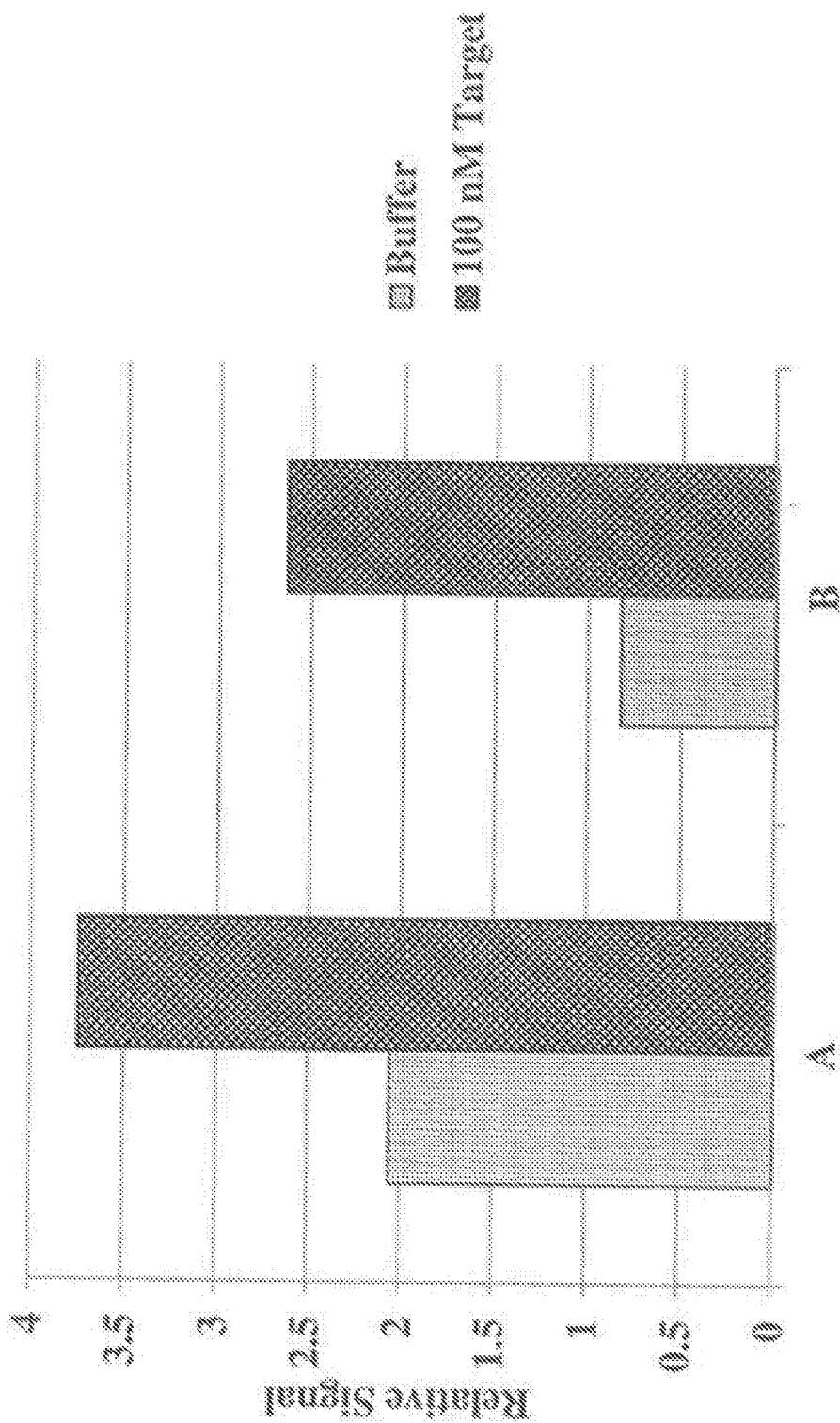
FIG. 9 is a chart showing the non-specific signal from buffer alone or target with two different probes having the same label, according to various aspects of the present disclosure.

The captor molecule Sau453 (SEQ ID NO:22) was printed onto NSB-27 slides at a concentration of 20 µM and was hybridized at 37° C. to either buffer alone or to its target at a concentration of 100 nM for ten minutes using the second hybridization buffer. The slide was rinsed with the second rinse buffer. The labeled probe, either (A) 16D (SEQ ID NO:7), or (B) 13D (SEQ ID NO:2) was then added at a concentration of 1.0 nM for ten minutes in the first detection buffer. After a further rinse with the second rinse buffer and a final rinse with a buffer containing 9 mM NaCl and 0.9 mM sodium citrate, the distribution of fluorescence was analyzed on a commercially available GenePix 4200b scanner. As shown in FIG. 9, a decrease in relative signal in buffer alone with the 13D labeled probe (SEQ ID NO:2; see column B, FIG. 9) versus that with the 16D labeled probe (SEQ ID NO:7; see column A, FIG. 9) demonstrates that the shorter labeled probe did not bind to the closed target-less captor molecule as readily as the longer probe does.

Example 8

Figure 10:
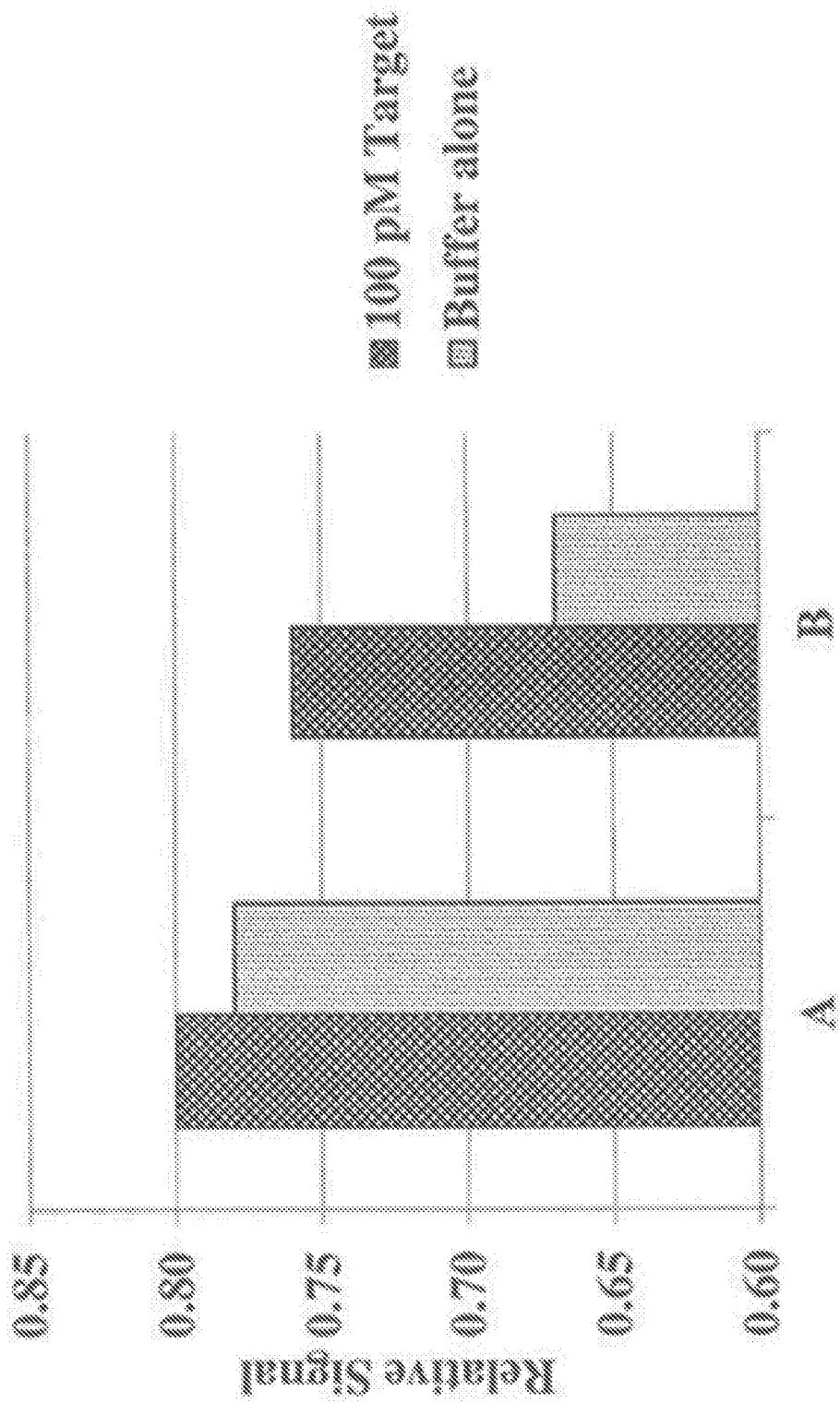
FIG. 10 is a chart showing the non-specific signal from buffer alone or target with two different labeled probes, according to various aspects of the present disclosure.

For example, the captor molecule Ec632 (SEQ ID NO:1) was printed onto NSB-27 slides at a concentration of 0.18 µM and was hybridized at 52° C. to buffer alone or to its target Ec632S (SEQ ID NO:23) at a concentration of 100 pM for 10 minutes using the first hybridization buffer. The slide was rinsed with the first rinse buffer. The labeled probe, either (A) 13Dn with ATTO 647N (SEQ ID NO:24) or (B) 13D with Alexa-647 (SEQ ID NO:2), was then added at 23° C. for 2.5 minutes in the first detection buffer. After a further rinse with the first rinse buffer and a final rinse with the first final rinse buffer, the distribution of fluorescence was analyzed on a commercially available GenePix 4200b scanner. As shown in FIG. 10, the relative signal from 100 pM target with the ATTO 647N labeled probe (SEQ ID NO:24; see column A, FIG. 10) was slightly higher than the signal with the Alexa-647 labeled probe (SEQ ID NO:2; see column B, FIG. 10).

As one skilled in the art can appreciate, the significant non-specific binding with the ATTO 647N labeled probe (SEQ ID NO:24) was unexpected. The data show that the fluorescent molecule Alexa 647 (Alexa Fluor® 647, Invitrogen, Thermo Fischer Scientific Inc., Waltham, Mass.) on the labeled 13-nucleotide probe (SEQ ID NO:2) generated a labeled probe that bound only to the captors that had bound to their target nucleic acids. In contrast, using the fluorescent molecule ATTO 647N (Sigma Aldrich, St. Louis, Mo.) on the labeled 13-nucleotide probe (SEQ ID NO:24) caused a high level of non-specific binding of the labeled probe to the captor in the absence of the target nucleic acid.

The structures of the two fluors were compared and it was determined that the ATTO-647N was more hydrophobic and was positively-charged. It was determined that the ATTO 647N fluor has a net +1 charge and is more hydrophobic than the Alexa 647 fluor that has a net −3 charge.

Without wishing to be bound by a particular theory, it is believed that the probe labeled with the ATTO-647N may be able to spend more time near the hydrophobic substrate on which the captor molecules were attached and approach the negatively-charged captor molecules more readily, thereby non-specifically opening up the closed stem-loop of the captor molecules into the open conformation in the absence of target binding. Without wishing to be bound by a particular theory, it is believed that a detector labeled with a hydrophilic and negatively-charged fluor such as Alexa647-labeled 13D (SEQ ID NO:2) may be able to perform more robustly in the disclosed method.

Example 9

Figure 11:
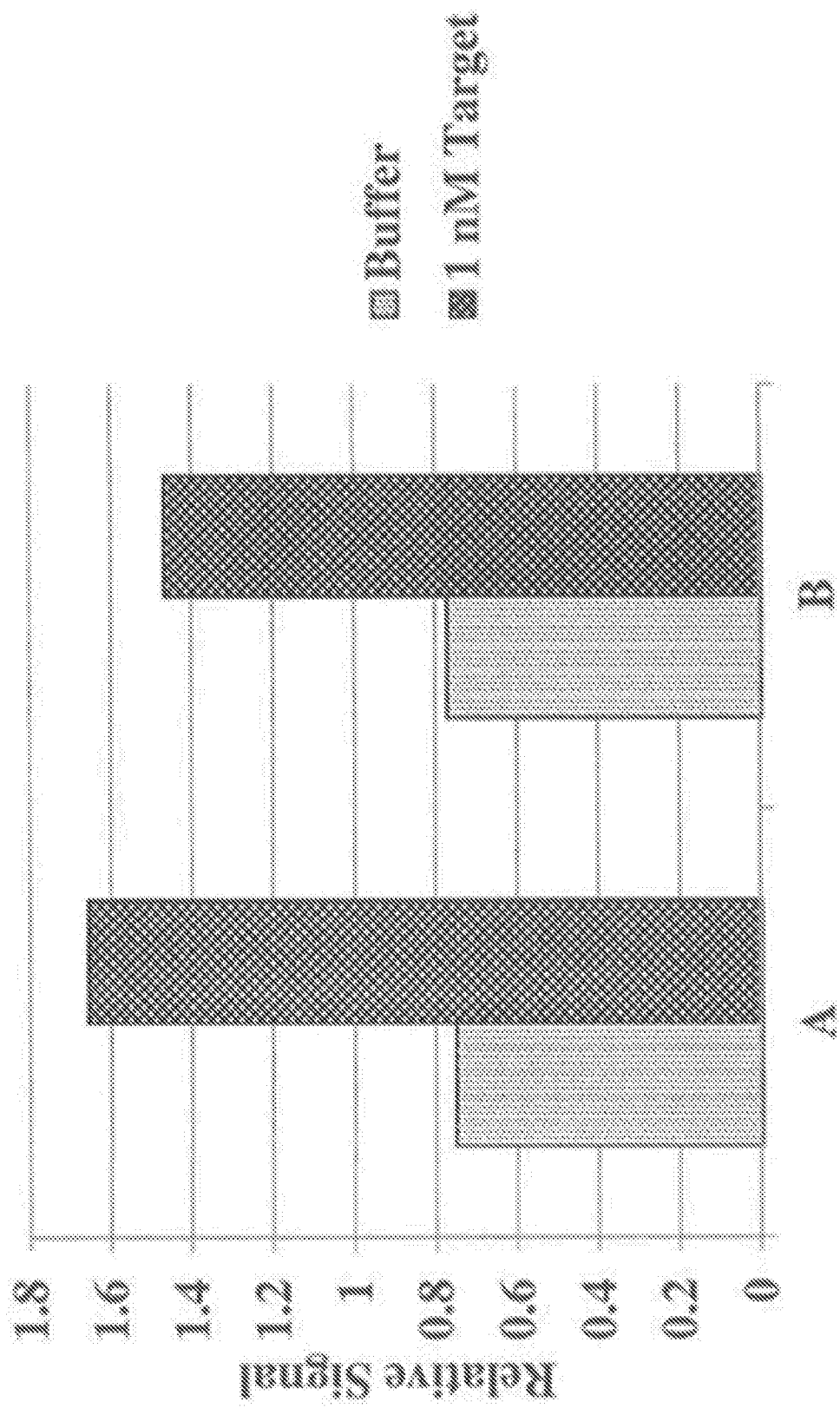
FIG. 11 is a chart showing the non-specific signal from buffer alone or target for two captor molecules with highly matched melting temperatures, according to various aspects of the present disclosure.

The calculated melting temperature of target Ec632S (SEQ ID NO:23) is 64.3° C. and the calculated melting temperature of target CV1S (SEQ ID NO:26) is 64.6 C. Calculations are based on the models of J SantaLucia Jr and D Hicks, Annu. Rev. Biophys. Biomol. Struct. 24.33:415-40. The captor molecules (A) Ec632 (SEQ ID NO:1) and (B) CHIKV-1 (SEQ ID NO:25) were printed onto NSB-27 slides at a concentration of 0.4 µM and were hybridized at 54° C. to either buffer alone or to their respective targets at concentrations of 1 nM for 20 minutes using the first hybridization buffer. The slide was rinsed with the first rinse buffer. The labeled probe 13D (SEQ ID NO:2) was then added at 23° C. for 2.5 minutes in the first detection buffer. After a further rinse with the first rinse buffer and a final rinse with the first final rinse buffer, the distribution of fluorescence was analyzed on a commercially available GenePix 4200b scanner. The relative signals obtained using these two captor molecules whose stem sequences have been altered is shown in FIG. 11. The relative signals generated by the two captor molecules, Ec632 (SEQ ID NO:1; column A, FIG. 11) and CHIKV-1 (SEQ ID NO:25; column B, FIG. 11) in the absence or presence of their targets is very similar.

Example 10

Figure 12:
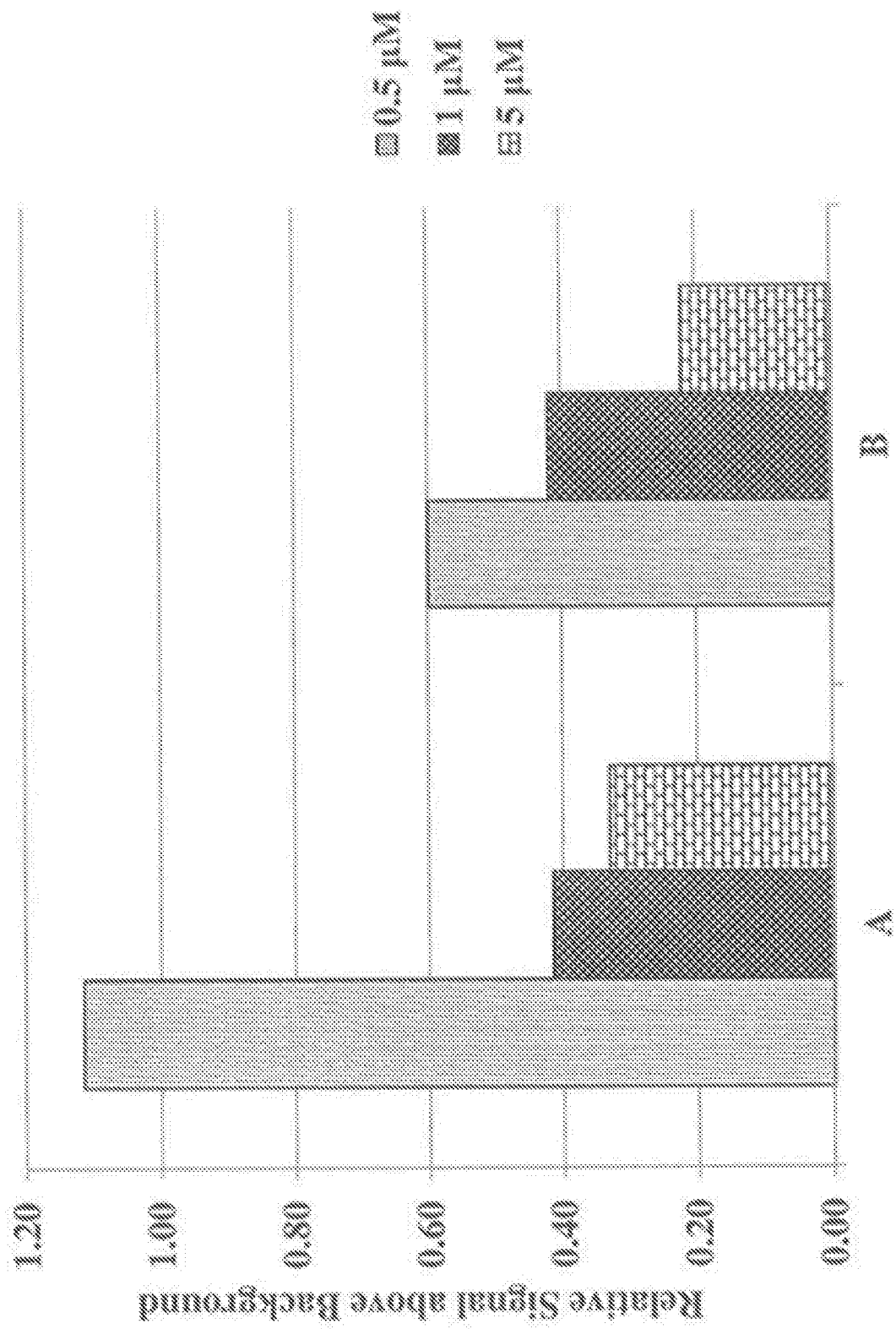
FIG. 12 is a chart showing the relative target-binding signal of two captor molecules when the captor molecules were bound to a substrate at decreasing captor molecule concentrations, according to various aspects of the present disclosure.

The captor molecules (A) Pos1 (SEQ ID NO:17), and (B) SapurK1 (SEQ ID NO:27) were printed onto the same set of NSB-27 slides at concentrations of 0.5, 1, and 5 µM and were hybridized at 52° C. with either buffer alone or the targets Pos1T (SEQ ID NO:18), and SapurK1T (SEQ ID NO:28) at concentrations of 100 pM for 20 minutes using a hybridization buffer of 300 mM NaCl, 20 mM NaH$_2$PO$_4$, 2 mM EDTA, 0.25 M DMSO, and 0.05% SDS, pH 7.4. The slides were rinsed with the second rinse buffer. The labeled probe 13D (SEQ ID NO:2) was then added at 5 nM for 30 seconds in the first detection buffer. After a further rinse with the second rinse buffer and a final rinse with a buffer containing 112.5 mM NaCl and 11 mM sodium citrate, the distribution of fluorescence was analyzed on a commercially available GenePix 4200b scanner. The graph in FIG. 12 shows that the relative signal above background increases for both captor molecules (see columns A and B, FIG. 12, for data obtained using captor molecules Pos1 (SEQ ID NO:17) and SapurK1 (SEQ ID NO:27), respectively) increases as the concentration of captor molecule printed on the slide decreases and appears to be associated with the decrease in the buffer only signals.

Example 11

Figure 13:
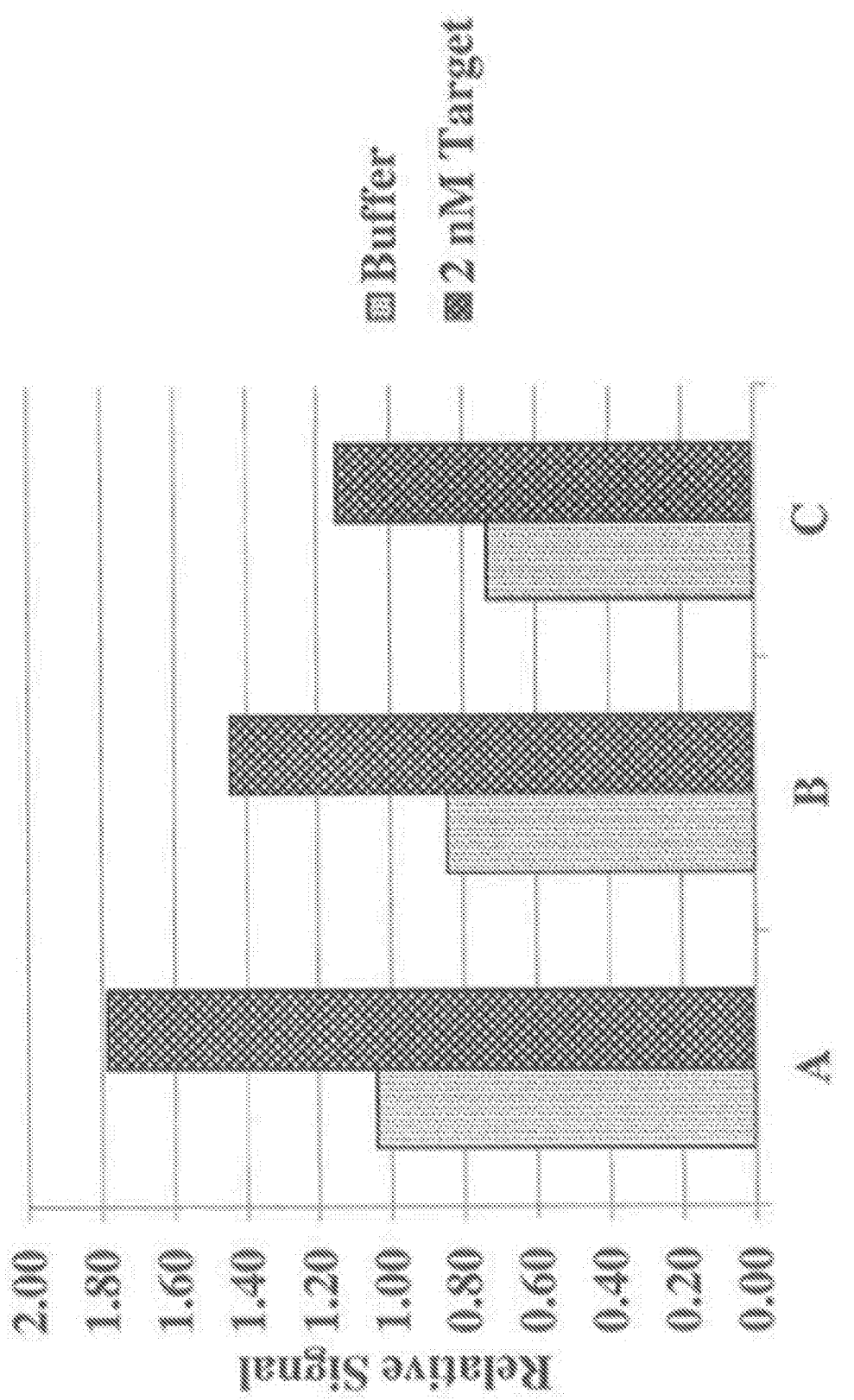
FIG. 13 is a chart showing the relative non-specific signal and target-binding signal of one captor molecule when the captor molecule was bound to a substrate in the presence of different molar ratios of a competitor for binding, according to various aspects of the present disclosure.

The captor molecule Ec3 (SEQ ID NO:29) was printed onto NSB-27 slides at a concentration of 1 µM with increasing ratios of a competitive inhibitor (SEQ ID NO:30). The captor molecule and inhibitor were mixed in the following molar ratios: (A) 1:3; (B) 1:4; and (C) 1:5. The slides were hybridized at 52° C. to buffer only or to the target Ec3S (SEQ ID NO:31) at a concentration of 2 nM for 10 minutes using the first hybridization buffer. The slide was rinsed with the first rinse buffer. The labeled probe 13D (SEQ ID NO:2) was then added at 23° C. for 2.5 minutes in the first detection buffer. After a further rinse with the first rinse buffer and the first final rinse buffer, the distribution of fluorescence was analyzed on a commercially available GenePix 4200b scanner. The data are shown in FIG. 13, where columns A represents data obtained at captor molecule to inhibitor molar ratio of 1:3; columns B represents data obtained at captor molecule to inhibitor molar ratio of 1:4; and columns C represents data obtained at captor molecule to inhibitor molar ratio of 1:5. The data show as the ratio of the competitive inhibitor increases (compare columns A to B to C, FIG. 11) that the relative signal in the presence or absence of Ec3S (SEQ ID NO:31) target decreases, suggesting that less of the Ec3 captor molecule (SEQ ID NO:29) has bound to the substrate.

Example 12 The following buffers were used in Example 12.

Hybridization Buffer. The third hybridization buffer was 2×TE Buffer, pH 7.4 (20 mM Tris(hydroxymethyl)aminomethane-HCl, 2 mM EDTA) with added 320 mM NaCl, 250 mM DMSO and 0.005% SDS.

Rinse Buffer. The third rinse buffer consisted of 2×TE Buffer, pH 7.4 with added 320 mM NaCl, 2% v/v EtOH and 0.05% SDS.

Detection Buffer. The second detection buffer consisted of 2×TE Buffer, pH 7.4 with added 320 mM NaCl and 0.1% SDS.

Final Rinse Buffer. The second final rinse buffer consisted of 2× Phosphate Buffered Saline (40 mM Phosphate, 300 mM NaCl), with added 1 mM ascorbic acid and 975 mM NaCl.

Various strains of the bacterium *E. coli* have been grown in tryptic soy broth medium, diluted to a concentration of 5e7 colony forming units per milliliter and grown for 90 minutes at 37 C in the presence or absence of 100 micrograms per milliliter (µg/mL) of tetracycline or 50 µg/mL of ampicillin. The cultures were centrifuged and processed as described in [0184] to lyse the bacteria and fragment the RNA. The fragmented RNA was used in the disclosed assay with captor molecules Ec23S-511 (SEQ ID NO:232), Ec16S-514 (SEQ ID NO:283), Ec16S-932 (SEQ ID NO:285), Ec23S-2490 (SEQ ID NO:287) and Ec23S-1930 (SEQ ID NO:286), shown in Table I. The RNA was hybridized to the captor molecules for one hour using the third hybridization buffer. A rinse step to remove non-specific RNA was performed using the third rinse buffer. The labeled probe 13D (SEQ ID NO:2), see Table I, was added at a concentration of 2 nM for four minutes in the second detection buffer. After a further rinse with the third rinse buffer and the second final rinse buffer, the distribution of fluorescence was analyzed using a commercially available GenePix 4200b scanner.

As shown in FIG. 19, *E. coli* strain ATCC 25922, which is known to be sensitive to the antibiotic tetracycline, was grown in the presence or absence of tetracycline and treated as described above. The relative signal above background when this strain was grown in the presence of tetracycline (FIG. 19, B) is significantly lower than without the antibiotic (FIG. 19, A.) Tetracycline inhibits the growth of this strain, and the disclosed method thereby confirmed the sensitivity of strain 25922 to tetracycline. The error bars in FIG. 19 represent the standard error of the relative signals in the assay As shown in FIG. 20, strain UAH202, a clinical isolate from a urinary tract infection, was grown in the presence or absence of ampicillin and treated as described above. The relative signal above background when this strain was grown in the presence of ampicillin (FIG. 20, B) is statistically similar to the signal from the sample grown without the antibiotic (FIG. 20, A.) These results indicate that strain UAH202 experienced no growth inhibition by the antibiotic and would be expected to be ampicillin resistant. Independent lab culture results confirmed that this strain is ampicillin resistant. The error bars in FIG. 20 represent the standard error of the relative signals in the assay.

A method disclosed herein comprises a method for detecting target nucleic acid molecules, comprising, a) contacting target nucleic acids to captor molecules attached to a substrate of an assay device comprising, i) one or more types of captor molecules attached by a linker to the substrate, wherein individual captors are spaced apart from one another at a distance to prevent captor molecule-dimers; and ii) one or more general negative control captor molecules attached to the substrate, in buffering conditions that allow for hybridization of the target nucleic acids with captor molecules; b) adding a detectable probe that is capable of binding to a captor molecule; and c) detecting the amount, location on the substrate, or both, of the detectable probe. In a method disclosed herein, captor molecules may be spaced apart from each by at least half of the length of the closed hairpin of the captor molecule. In a method disclosed herein, a general negative control captor molecule comprises SEQ ID NO: 160. In a method disclosed herein, prior to step a), concentrating the target nucleic acids. In a method disclosed herein, prior to step a), adding helper oligos to the target nucleic acids. In a method disclosed herein, prior to step a), concentrating the target nucleic acids and adding helper oligos to the concentrated target nucleic acids. In a method disclosed herein, after b) and before c), removing unbound probe. In a method disclosed herein, adding a solution comprising ascorbic acid. In a method disclosed herein, after b) and before c), adding a solution comprising ascorbic acid and removing unbound probe.

A method disclosed herein comprises buffering conditions comprising one or more buffers comprising one or more of ionic surfactants, sodium dodecyl sulfate at concentrations from 0.005% to 0.2% v/v; ethanol at concentrations from 5% v/v to 30% v/v, dimethyl sulfoxide (DMSO) at concentrations from 0.10 M to 1.0 M; or combinations thereof. In a method disclosed herein, a substrate may comprise a microarray slide, a microbead, a paramagnetic bead, a fiber optic cable, the surface of a microtiter plate, an electrically conducting surface such as a wire, or other surfaces. In a method disclosed herein, a detectable probe comprises fewer nucleotides that are complementary to a stem region of a captor than the total number of nucleotides in a stem region of a captor molecule. In a method disclosed herein, a detectable probe comprises a label comprising one or more of a fluorescent compound or molecule, a bioluminescent compound or molecule, a chemiluminescent compound or molecule, radioisotopes, a member of a binding pair, an enzyme, an enzyme substrates, a reactive group or a chromophore.

In a method disclosed herein, an assay device has competitive binding inhibitors attached to the substrate. A competitive binding inhibitor may comprise a linker attached to SEQ ID NO:30. A captor molecule may be attached to the substrate by a linker. A linker molecule may comprise a 6-carbon polymer.

In a method disclosed herein, captor molecule may comprise, in a 5'-3' direction, a first stem region, a loop region, and a second stem region complementary to the first stem region.

One or more captor molecules may be selected from the group consisting of SEQ ID NOs: 1, 3-6, 8, 15, 17, 19, 21-22, 25, 27, 29, 32-323, and 339. One or more probes are selected from the group consisting of SEQ ID NOs: 2, 7, 16, 24, and 336-338. One or more helper oligos are selected from the group consisting of SEQ ID Nos: 324-335.

A composition useful in methods, systems and devices disclosed herein may comprise one or more detectable probe selected from the group consisting of SEQ ID NOs: 2, 7, 16, 24, and 336-338. A composition useful in methods, systems and devices disclosed herein may comprise one or more helper oligos are selected from the group consisting of SEQ ID Nos: 324-335. A composition useful in methods, systems and devices disclosed herein may comprise one or more captor molecules are selected from the group consisting of SEQ ID NOs: 1, 3-6, 8, 15, 17, 19, 21-22, 25, 27, 29, 32-323, and 339.

An assay device for detecting target nucleic acids disclosed herein may comprise a) a substrate, b) one or more types of captor molecules attached to the substrate via a linker molecule and spaced apart from one another at a distance to prevent captor molecule-dimers, and c) one or more general negative control captor molecules attached to the substrate. An assay device disclosed herein may comprise a substrate comprising a microarray slide, a microbead, a paramagnetic bead, a fiber optic cable, the surface of a microtiter plate, an electrically conducting surface such as a wire, or other surfaces. An assay device disclosed herein may comprise competitive binding inhibitors attached to the substrate. Such competitive binding inhibitors may comprise comprises a linker attached to attached to a nucleic acid polymer, for example, SEQ ID NO:30. An assay device disclosed herein may comprise one or more captor molecules attached at a particular location on the substrate. An assay device disclosed herein may comprise one or more captor molecules attached at one or more particular locations on the substrate. For example, one type of captor molecules (a plurality of captor molecules) may be found in a particular location on a substrate, and a different type of captor molecules (a plurality of captor molecules) may be attached in a different location on a substrate. Or, in the case of microbeads or other particles, one type of captor molecules attached to a particle substrate may be in a different location, such as a microtiter well, than is another type of captor molecule attached to a particle substrate. The same may be true for negative controls, whether general or specific. An assay device disclosed herein may comprise one or more general negative control captor molecules attached at one or more particular locations on the substrate. An assay device disclosed herein may comprise specific negative control captor molecules, which may be attached to a particular location on a substrate.

A system for detecting target nucleic acids disclosed herein may comprise a) an assay device for detecting target nucleic acids, comprising i) a substrate; ii) one or more types of captor molecules attached to the substrate via a linker molecule and spaced apart from one another at a distance to prevent captor molecule-dimers; and iii) one or more general negative control captor molecules attached to the substrate; b) solutions comprising buffers or rinses; and c) one or more detectable nucleic acid probes. A system for detecting target nucleic acids disclosed herein may comprise helper oligos. A system for detecting target nucleic acids disclosed herein may comprise a substrate further comprising attached competitive binding inhibitors.

A kit for detecting target nucleic acids may comprise at least one of: (a) a nucleic acid captor molecule comprising a loop region and a stem region, wherein the nucleic acid captor molecule has a closed stem-loop structure; and wherein the closed stem-loop structure is replaced with an open stem-loop structure when the nucleic acid captor molecule contacts a target nucleic acid; or (b) a labeled probe; wherein the labeled probe comprises a disclosed probe sequence linked to a disclosed label; and wherein the labeled probe binds to the stem region of the open stem-loop structure; and optionally comprising one or more of (c) an incubation or hybridizing buffer; (d) a rinsing buffer; (e) a final rinse buffer; and (0 instructions for one or more of incubating/hybridizing and rinsing the nucleic acid captor molecule with a sample, incubating and rinsing after adding the labeled nucleic acid probe and final rinsing before detecting the presence of the labeled nucleic acid probe. A kit for detecting target nucleic acids may comprise a substrate for attaching captor molecules.

The foregoing description of aspects of the methods, systems, and components of the present disclosure has been provided for the purposes of illustration and description. It is not intended to be exhaustive or to limit the present disclosure to the precise forms disclosed. Many modifications and variations will be apparent to one of ordinary skill in the relevant arts. For example, steps performed in the aspects of the present disclosure disclosed can alternate orders, certain steps can be omitted, and additional steps can be added. The aspects were chosen and described in order to best explain the principles of the present disclosure and its practical application, thereby enabling others skilled in the art to understand the present disclosure for various aspects and with various modifications that are suited to the particular use contemplated. Other aspects are possible and are covered by the present disclosure. Such aspects will be apparent to persons skilled in the relevant art(s) based on the teachings contained herein. The breadth and scope of the present disclosure should not be limited by any of the above-described exemplary aspects, but should be defined only in accordance with the following claims and their equivalents. All references cited herein are each incorporated by reference herein in its entirety.

What is claimed is:

1. A method for detecting target nucleic acid molecules, comprising,
   a) contacting target nucleic acids to a captor molecule attached to a substrate of an assay device comprising,
      i) the captor molecules are attached by a linker to the substrate, wherein individual captors are spaced apart from one another at a distance to prevent captor molecule-dimers; and
      ii) one or more negative controls attached to the substrate;
   in buffering conditions that allow for hybridization of the target nucleic acids with captor molecules;
   b) adding a detectable probe that is capable of binding to the captor molecule; and
   c) detecting the amount, location on the substrate, or both, of the detectable probe specifically bound to captor-molecules and negative controls; wherein detection of probe binding to captor molecules at probe amounts above negative controls and above probe amounts in the absence of target nucleic acids is specific binding.

2. The method of claim 1, wherein the captor molecules are spaced apart from each by at least half of the length of the closed hairpin of the captor molecule.

3. The method of claim 1, wherein the negative control captor molecule is SEQ ID NO: 160.

4. The method of claim 1, further comprising, prior to step a), concentrating the target nucleic acids.

5. The method of claim 1, further comprising, after b) and before c), adding a solution comprising ascorbic acid and removing unbound probe.

6. The method of claim 1, wherein the buffering conditions comprise one or more buffers comprising one or more of ionic surfactants, sodium dodecyl sulfate at concentrations from 0.005% to 0.2% v/v; ethanol at concentrations from 5% v/v to 30% v/v, dimethyl sulfoxide (DMSO) at concentrations from 0.10 M to 1.0 M; and combinations thereof.

7. The method of claim 1, wherein the detectable probe comprises fewer nucleotides that are complementary to a stem region of the captor molecule than the total number of nucleotides in a stem region of the captor molecule.

8. The method of claim 1, wherein the assay device has competitive binding inhibitors attached to the substrate.

9. The method of claim 8, wherein the competitive binding inhibitor comprises the linker attached to SEQ ID NO:30.

10. The method of claim 1, wherein the captor molecule comprises SEQ ID NO: 1.

11. The method of claim 1, wherein the probe comprises SEQ ID NO: 2.

12. A composition for use in the method of claim 1, comprising detectable probe selected from the group consisting of SEQ ID NOs: 2, 7, 16, 24, and 336-338.

13. A composition for use in the method of claim 1, comprising a helper oligos selected from the group consisting of SEQ ID Nos: 324-335.

14. A composition for use in the method of claim 1, comprising captor molecules selected from the group consisting of SEQ ID NOs: 1, 3-6, 8, 15, 17, 19, 21-22, 25, 27, 29, 32-323, and 339.

15. An assay device for detecting target nucleic acids, comprising
   a) a substrate
   b) types of captor molecules attached to the substrate via a linker molecule and spaced apart from one another at a distance to prevent captor molecule-dimers; and
   c) one or more negative control captor molecules attached to the substrate.

16. The device of claim 15, wherein the assay device further comprises binding inhibitors attached to the substrate.

17. The device of claim 15, wherein the competitive binding inhibitor comprises a linker attached to SEQ ID NO:30.

18. The device of claim 15, further comprising specific negative control captor molecules.

19. A system for detecting target nucleic acids, comprising,
   a) an assay device for detecting target nucleic acids, comprising,
      i) a substrate;
      ii) captor molecules attached to the substrate via a linker molecule; and wherein the individual captor molecules are spaced apart from one another at a distance to prevent captor molecule-dimers; and iii) one or more negative control captor molecules attached to the substrate;

b) solutions comprising buffers or rinses;

c) one or more detectable nucleic acid probes.

20. The system of claim 19, wherein the substrate further comprises attached competitive binding inhibitors.

21. A kit comprising at least one of:

(a) a nucleic acid captor molecule comprising a loop region and a stem region, wherein the nucleic acid captor molecule has a closed stem-loop structure; and wherein the closed stem-loop structure is replaced with an open stem-loop structure when the nucleic acid captor molecule contacts a target nucleic acid; or (b) a labeled probe; wherein the labeled probe comprises a disclosed probe sequence linked to a disclosed label; and wherein the labeled probe binds to the stem region of the open stem-loop structure.

* * * * *

SEQUENCE LISTING

```
<160> NUMBER OF SEQ ID NOS: 339

<210> SEQ ID NO 1
<211> LENGTH: 56
<212> TYPE: DNA
<213> ORGANISM: Artificial Sequence
<220> FEATURE:
<223> OTHER INFORMATION: Synthetic Construct

<400> SEQUENCE: 1
gacagacaga cagacactca agcttgccag tatcagatgc tgtctgtctg tctgtc          56

<210> SEQ ID NO 2
<211> LENGTH: 13
<212> TYPE: DNA
<213> ORGANISM: Artificial Sequence
<220> FEATURE:
<223> OTHER INFORMATION: Synthetic Construct

<400> SEQUENCE: 2
gacagacaga cag                                                        13

<210> SEQ ID NO 3
<211> LENGTH: 106
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
```

```
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 3
ganagacaga nagacataga tctcctccgt ccaatatcct tgtctgtctg ganagacaga       60
nagacataga tctcctccgt ccaatatcct tgtctgtctg tctgtc                    106

<210> SEQ ID NO 4
<211> LENGTH: 61
<212> TYPE: DNA
<213> ORGANISM: Artificial Sequence
<220> FEATURE:
<223> OTHER INFORMATION: Synthetic Construct

<400> SEQUENCE: 4
gacagacaga cagacactgc gggtaacgtc aatgagcaaa gaaaatgtct gtctgtctgt      60
c                                                                     61

<210> SEQ ID NO 5
<211> LENGTH: 57
<212> TYPE: DNA
<213> ORGANISM: Artificial Sequence
<220> FEATURE:
<223> OTHER INFORMATION: Synthetic Construct

<400> SEQUENCE: 5
gacagacaga cagactgcgg gtaacgtcaa tgagcaaaga aaatctgtct gtctgtc         57

<210> SEQ ID NO 6
<211> LENGTH: 53
<212> TYPE: DNA
<213> ORGANISM: Artificial Sequence
<220> FEATURE:
<223> OTHER INFORMATION: Synthetic Construct

<400> SEQUENCE: 6
gacagacaga cactgcgggt aacgtcaatg agcaaagaaa atgtctgtct gtc             53

<210> SEQ ID NO 7
<211> LENGTH: 16
<212> TYPE: DNA
<213> ORGANISM: Artificial Sequence
<220> FEATURE:
<223> OTHER INFORMATION: Synthetic Construct

<400> SEQUENCE: 7
gacagacaga cagaca                                                      16

<210> SEQ ID NO 8
<211> LENGTH: 56
<212> TYPE: DNA
<213> ORGANISM: Artificial Sequence
<220> FEATURE:
<223> OTHER INFORMATION: Synthetic Construct

<400> SEQUENCE: 8
```

```
gacagacaga cagacagtta cttacacata tgttcttccc tgtctgtctg tctgtc          56
```

<210> SEQ ID NO 9
<211> LENGTH: 27
<212> TYPE: DNA
<213> ORGANISM: Artificial Sequence
<220> FEATURE:
<223> OTHER INFORMATION: Synthetic Construct

<400> SEQUENCE: 9

```
gggaagaaca tatgtgtaag taactgt                                          27
```

<210> SEQ ID NO 10
<211> LENGTH: 27
<212> TYPE: DNA
<213> ORGANISM: Artificial Sequence
<220> FEATURE:
<223> OTHER INFORMATION: Synthetic Construct

<400> SEQUENCE: 10

```
gggaagaaca tctgtgtcag taactgt                                          27
```

<210> SEQ ID NO 11
<211> LENGTH: 27
<212> TYPE: DNA
<213> ORGANISM: Artificial Sequence
<220> FEATURE:
<223> OTHER INFORMATION: Synthetic Construct

<400> SEQUENCE: 11

```
gggaagaaca tgtgtgtgag taactgt                                          27
```

<210> SEQ ID NO 12
<211> LENGTH: 27
<212> TYPE: DNA
<213> ORGANISM: Artificial Sequence
<220> FEATURE:
<223> OTHER INFORMATION: Synthetic Construct

<400> SEQUENCE: 12

```
gggaagaaca tatctgtaag taactgt                                          27
```

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

<400> SEQUENCE: 13

```
gaacatatgt gtaagtaact gt                                               22
```

<210> SEQ ID NO 14
<211> LENGTH: 22
<212> TYPE: DNA
<213> ORGANISM: Artificial Sequence
<220> FEATURE:
<223> OTHER INFORMATION: Synthetic Construct

<400> SEQUENCE: 14

```
gggaagaaca tatgtgtaag ta                                               22
```

<210> SEQ ID NO 15
<211> LENGTH: 56
<212> TYPE: DNA

<213> ORGANISM: Artificial Sequence
<220> FEATURE:
<223> OTHER INFORMATION: Synthetic Construct

<400> SEQUENCE: 15
cagagacaga cagacagtta cttacacata tgttcttccc tgtctgtctg tctctg      56

<210> SEQ ID NO 16
<211> LENGTH: 11
<212> TYPE: DNA
<213> ORGANISM: Artificial Sequence
<220> FEATURE:
<223> OTHER INFORMATION: Synthetic Construct

<400> SEQUENCE: 16
cagagacaga c      11

<210> SEQ ID NO 17
<211> LENGTH: 56
<212> TYPE: DNA
<213> ORGANISM: Artificial Sequence
<220> FEATURE:
<223> OTHER INFORMATION: Synthetic Construct

<400> SEQUENCE: 17
gacagacaga cagacataga tctcctccgt ccaatatcct tgtctgtctg tctgtc      56

<210> SEQ ID NO 18
<211> LENGTH: 26
<212> TYPE: DNA
<213> ORGANISM: Artificial Sequence
<220> FEATURE:
<223> OTHER INFORMATION: Synthetic Construct

<400> SEQUENCE: 18
aggatattgg acggaggaga tctatg      26

<210> SEQ ID NO 19
<211> LENGTH: 56
<212> TYPE: DNA
<213> ORGANISM: Artificial Sequence
<220> FEATURE:
<223> OTHER INFORMATION: Synthetic Construct

<400> SEQUENCE: 19
gacagacaga cagacagttc tgcagtaccg gatttgccaa tgtctgtctg tctgtc      56

<210> SEQ ID NO 20
<211> LENGTH: 26
<212> TYPE: DNA
<213> ORGANISM: Artificial Sequence
<220> FEATURE:
<223> OTHER INFORMATION: Synthetic Construct

<400> SEQUENCE: 20
attggcaaat ccggtactgc agaact      26

<210> SEQ ID NO 21
<211> LENGTH: 52
<212> TYPE: DNA
<213> ORGANISM: Artificial Sequence
<220> FEATURE:
<223> OTHER INFORMATION: Synthetic Construct

<400> SEQUENCE: 21
gacagacaga cagacagaag caagcttctc gtccgttgtc tgtctgtctg tc      52

```
<210> SEQ ID NO 22
<211> LENGTH: 60
<212> TYPE: DNA
<213> ORGANISM: Artificial Sequence
<220> FEATURE:
<223> OTHER INFORMATION: Synthetic Construct

<400> SEQUENCE: 22
gacagacaga cagacagtta cttacacata tgttcttccc aaaatgtctg tctgtctgtc      60

<210> SEQ ID NO 23
<211> LENGTH: 25
<212> TYPE: DNA
<213> ORGANISM: Artificial Sequence
<220> FEATURE:
<223> OTHER INFORMATION: Synthetic Construct

<400> SEQUENCE: 23
gcatctgata ctggcaagct tgagt                                            25

<210> SEQ ID NO 24
<211> LENGTH: 13
<212> TYPE: DNA
<213> ORGANISM: Artificial Sequence
<220> FEATURE:
<223> OTHER INFORMATION: Synthetic Construct

<400> SEQUENCE: 24
gacagacaga cag                                                         13

<210> SEQ ID NO 25
<211> LENGTH: 56
<212> TYPE: DNA
<213> ORGANISM: Artificial Sequence
<220> FEATURE:
<223> OTHER INFORMATION: Synthetic Construct

<400> SEQUENCE: 25
gacagacaga cagacccata ccagtttacc ttccgtacgc ggtctgtctg tctgtc          56

<210> SEQ ID NO 26
<211> LENGTH: 25
<212> TYPE: DNA
<213> ORGANISM: Artificial Sequence
<220> FEATURE:
<223> OTHER INFORMATION: Synthetic Construct

<400> SEQUENCE: 26
gcgtacggaa ggtaaactgg tatgg                                            25

<210> SEQ ID NO 27
<211> LENGTH: 56
<212> TYPE: DNA
<213> ORGANISM: Artificial Sequence
<220> FEATURE:
<223> OTHER INFORMATION: Synthetic Construct

<400> SEQUENCE: 27
gacagacaga cagacaagct gaccaccacc aataatgcca tgtctgtctg tctgtc          56

<210> SEQ ID NO 28
<211> LENGTH: 26
<212> TYPE: DNA
<213> ORGANISM: Artificial Sequence
<220> FEATURE:
```

<223> OTHER INFORMATION: Synthetic Construct

<400> SEQUENCE: 28
tggcattatt ggtggtggtc agcttg                                              26

<210> SEQ ID NO 29
<211> LENGTH: 56
<212> TYPE: DNA
<213> ORGANISM: Artificial Sequence
<220> FEATURE:
<223> OTHER INFORMATION: Synthetic Construct

<400> SEQUENCE: 29
gacagacaga cagacaacaa caccggtgaa atgttcttca tgtctgtctg tctgtc           56

<210> SEQ ID NO 30
<211> LENGTH: 10
<212> TYPE: DNA
<213> ORGANISM: Artificial Sequence
<220> FEATURE:
<223> OTHER INFORMATION: Synthetic Construct

<400> SEQUENCE: 30
aaaaaaaaaa                                                                10

<210> SEQ ID NO 31
<211> LENGTH: 26
<212> TYPE: DNA
<213> ORGANISM: Artificial Sequence
<220> FEATURE:
<223> OTHER INFORMATION: Synthetic Construct

<400> SEQUENCE: 31
tgaagaacat ttcaccggtg ttgttg                                              26

<210> SEQ ID NO 32
<211> LENGTH: 54
<212> TYPE: DNA
<213> ORGANISM: Artificial Sequence
<220> FEATURE:
<223> OTHER INFORMATION: Synthetic Construct

<400> SEQUENCE: 32
acacaggaag agacaccact cgttgtcaga cagcatcctt gtctcttcct gtgt              54

<210> SEQ ID NO 33
<211> LENGTH: 54
<212> TYPE: DNA
<213> ORGANISM: Artificial Sequence
<220> FEATURE:
<223> OTHER INFORMATION: Synthetic Construct

<400> SEQUENCE: 33
acacaggaag agacaccact cgttgtgtga caacatcctt gtctcttcct gtgt              54

<210> SEQ ID NO 34
<211> LENGTH: 54
<212> TYPE: DNA
<213> ORGANISM: Artificial Sequence
<220> FEATURE:
<223> OTHER INFORMATION: Synthetic Construct

<400> SEQUENCE: 34
acacaggaag agacataacg ccatgagtcc tttgcttatt gtctcttcct gtgt              54

```
<210> SEQ ID NO 35
<211> LENGTH: 54
<212> TYPE: DNA
<213> ORGANISM: Artificial Sequence
<220> FEATURE:
<223> OTHER INFORMATION: Synthetic Construct

<400> SEQUENCE: 35
acacaggaag agacataacg ccaagacacc attgcttatt gtctcttcct gtgt        54

<210> SEQ ID NO 36
<211> LENGTH: 55
<212> TYPE: DNA
<213> ORGANISM: Artificial Sequence
<220> FEATURE:
<223> OTHER INFORMATION: Synthetic Construct

<400> SEQUENCE: 36
acacaggaag agacactcaa agatatagtg gcggcacgca tgtctcttcc tgtgt       55

<210> SEQ ID NO 37
<211> LENGTH: 55
<212> TYPE: DNA
<213> ORGANISM: Artificial Sequence
<220> FEATURE:
<223> OTHER INFORMATION: Synthetic Construct

<400> SEQUENCE: 37
acacaggaag agacactcaa tcttatagtg gcggtacgca tgtctcttcc tgtgt       55

<210> SEQ ID NO 38
<211> LENGTH: 55
<212> TYPE: DNA
<213> ORGANISM: Artificial Sequence
<220> FEATURE:
<223> OTHER INFORMATION: Synthetic Construct

<400> SEQUENCE: 38
acacaggaag agacatcggt tgccgcacag ccctttaagt tgtctcttcc tgtgt       55

<210> SEQ ID NO 39
<211> LENGTH: 55
<212> TYPE: DNA
<213> ORGANISM: Artificial Sequence
<220> FEATURE:
<223> OTHER INFORMATION: Synthetic Construct

<400> SEQUENCE: 39
acacaggaag agacatcggg tgccgcacat gggttgtagt tgtctcttcc tgtgt       55

<210> SEQ ID NO 40
<211> LENGTH: 54
<212> TYPE: DNA
<213> ORGANISM: Artificial Sequence
<220> FEATURE:
<223> OTHER INFORMATION: Synthetic Construct

<400> SEQUENCE: 40
acacaggaag agacatagac gccggtgaag accttacagt gtctcttcct gtgt        54

<210> SEQ ID NO 41
<211> LENGTH: 54
<212> TYPE: DNA
<213> ORGANISM: Artificial Sequence
<220> FEATURE:
<223> OTHER INFORMATION: Synthetic Construct
```

<400> SEQUENCE: 41
acacaggaag agacatagac gccggtgaag accttacagt gtctcttcct gtgt            54

<210> SEQ ID NO 42
<211> LENGTH: 54
<212> TYPE: DNA
<213> ORGANISM: Artificial Sequence
<220> FEATURE:
<223> OTHER INFORMATION: Synthetic Construct

<400> SEQUENCE: 42
acacaggaag agacacatac cagtttacct tccgtacgct gtctcttcct gtgt            54

<210> SEQ ID NO 43
<211> LENGTH: 54
<212> TYPE: DNA
<213> ORGANISM: Artificial Sequence
<220> FEATURE:
<223> OTHER INFORMATION: Synthetic Construct

<400> SEQUENCE: 43
acacaggaag agacacatac cagtttacct tccgtacgct gtctcttcct gtgt            54

<210> SEQ ID NO 44
<211> LENGTH: 54
<212> TYPE: DNA
<213> ORGANISM: Artificial Sequence
<220> FEATURE:
<223> OTHER INFORMATION: Synthetic Construct

<400> SEQUENCE: 44
acacaggaag agacaggacg ctagccatgg gtgttatatt gtctcttcct gtgt            54

<210> SEQ ID NO 45
<211> LENGTH: 54
<212> TYPE: DNA
<213> ORGANISM: Artificial Sequence
<220> FEATURE:
<223> OTHER INFORMATION: Synthetic Construct

<400> SEQUENCE: 45
acacaggaag agacaggacg ctagggatgg gtgtaatatt gtctcttcct gtgt            54

<210> SEQ ID NO 46
<211> LENGTH: 54
<212> TYPE: DNA
<213> ORGANISM: Artificial Sequence
<220> FEATURE:
<223> OTHER INFORMATION: Synthetic Construct

<400> SEQUENCE: 46
acacaggaag agacagtagc tcagaagaca agctttcgat gtctcttcct gtgt            54

<210> SEQ ID NO 47
<211> LENGTH: 54
<212> TYPE: DNA
<213> ORGANISM: Artificial Sequence
<220> FEATURE:
<223> OTHER INFORMATION: Synthetic Construct

<400> SEQUENCE: 47
acacaggaag agacagttgc acagatgaca tgcattcgat gtctcttcct gtgt            54

<210> SEQ ID NO 48
<211> LENGTH: 56

```
<212> TYPE: DNA
<213> ORGANISM: Artificial Sequence
<220> FEATURE:
<223> OTHER INFORMATION: Synthetic Construct

<400> SEQUENCE: 48
acacaggaag agacaaatcc ttattgtgtc tggacctggt gtgtctcttc ctgtgt        56

<210> SEQ ID NO 49
<211> LENGTH: 54
<212> TYPE: DNA
<213> ORGANISM: Artificial Sequence
<220> FEATURE:
<223> OTHER INFORMATION: Synthetic Construct

<400> SEQUENCE: 49
acacaggaag agacactgtg cctggaatga tgctgaggat gtctcttcct gtgt          54

<210> SEQ ID NO 50
<211> LENGTH: 54
<212> TYPE: DNA
<213> ORGANISM: Artificial Sequence
<220> FEATURE:
<223> OTHER INFORMATION: Synthetic Construct

<400> SEQUENCE: 50
acacaggaag agacactgtg cctggatagt tgctgaggat gtctcttcct gtgt          54

<210> SEQ ID NO 51
<211> LENGTH: 54
<212> TYPE: DNA
<213> ORGANISM: Artificial Sequence
<220> FEATURE:
<223> OTHER INFORMATION: Synthetic Construct

<400> SEQUENCE: 51
acacaggaag agacatcata tgatccatga taggcccatt gtctcttcct gtgt          54

<210> SEQ ID NO 52
<211> LENGTH: 54
<212> TYPE: DNA
<213> ORGANISM: Artificial Sequence
<220> FEATURE:
<223> OTHER INFORMATION: Synthetic Construct

<400> SEQUENCE: 52
acacaggaag agacatcata tgatccttga atgcccattt gtctcttcct gtgt          54

<210> SEQ ID NO 53
<211> LENGTH: 54
<212> TYPE: DNA
<213> ORGANISM: Artificial Sequence
<220> FEATURE:
<223> OTHER INFORMATION: Synthetic Construct

<400> SEQUENCE: 53
acacaggaag agacaagctg tgtcacctaa aatggccaat gtctcttcct gtgt          54

<210> SEQ ID NO 54
<211> LENGTH: 54
<212> TYPE: DNA
<213> ORGANISM: Artificial Sequence
<220> FEATURE:
<223> OTHER INFORMATION: Synthetic Construct

<400> SEQUENCE: 54
```
acacaggaag agacaagctc tctcactcaa aatcgccaat gtctcttcct gtgt    54

<210> SEQ ID NO 55
<211> LENGTH: 54
<212> TYPE: DNA
<213> ORGANISM: Artificial Sequence
<220> FEATURE:
<223> OTHER INFORMATION: Synthetic Construct

<400> SEQUENCE: 55
acacaggaag agacatgctg ggtctgtgaa atgggcttct gtctcttcct gtgt    54

<210> SEQ ID NO 56
<211> LENGTH: 54
<212> TYPE: DNA
<213> ORGANISM: Artificial Sequence
<220> FEATURE:
<223> OTHER INFORMATION: Synthetic Construct

<400> SEQUENCE: 56
acacaggaag agacatgcag ggtcttggaa atgggcttct gtctcttcct gtgt    54

<210> SEQ ID NO 57
<211> LENGTH: 54
<212> TYPE: DNA
<213> ORGANISM: Artificial Sequence
<220> FEATURE:
<223> OTHER INFORMATION: Synthetic Construct

<400> SEQUENCE: 57
acacaggaag agacattcta gcccaagggt tccatattct gtctcttcct gtgt    54

<210> SEQ ID NO 58
<211> LENGTH: 54
<212> TYPE: DNA
<213> ORGANISM: Artificial Sequence
<220> FEATURE:
<223> OTHER INFORMATION: Synthetic Construct

<400> SEQUENCE: 58
acacaggaag agacattcta gcccttgggt tccattatct gtctcttcct gtgt    54

<210> SEQ ID NO 59
<211> LENGTH: 54
<212> TYPE: DNA
<213> ORGANISM: Artificial Sequence
<220> FEATURE:
<223> OTHER INFORMATION: Synthetic Construct

<400> SEQUENCE: 59
acacaggaag agacatcttt ggcttctgtt ctatccactt gtctcttcct gtgt    54

<210> SEQ ID NO 60
<211> LENGTH: 54
<212> TYPE: DNA
<213> ORGANISM: Artificial Sequence
<220> FEATURE:
<223> OTHER INFORMATION: Synthetic Construct

<400> SEQUENCE: 60
acacaggaag agacatctta ggcttctgat ctatcctctt gtctcttcct gtgt    54

<210> SEQ ID NO 61
<211> LENGTH: 55
<212> TYPE: DNA
<213> ORGANISM: Artificial Sequence
<220> FEATURE:
<223> OTHER INFORMATION: Synthetic Construct

<400> SEQUENCE: 61
acacaggaag agacaagatg tcctgcaaac atgtgatttc tgtctcttcc tgtgt     55

<210> SEQ ID NO 62
<211> LENGTH: 55
<212> TYPE: DNA
<213> ORGANISM: Artificial Sequence
<220> FEATURE:
<223> OTHER INFORMATION: Synthetic Construct

<400> SEQUENCE: 62
acacaggaag agacaagatg tcctgctttc atgtgatttc tgtctcttcc tgtgt     55

<210> SEQ ID NO 63
<211> LENGTH: 55
<212> TYPE: DNA
<213> ORGANISM: Artificial Sequence
<220> FEATURE:
<223> OTHER INFORMATION: Synthetic Construct

<400> SEQUENCE: 63
acacaggaag agacaagcat gagtgtttcc agtgactccg tgtctcttcc tgtgt     55

<210> SEQ ID NO 64
<211> LENGTH: 54
<212> TYPE: DNA
<213> ORGANISM: Artificial Sequence
<220> FEATURE:
<223> OTHER INFORMATION: Synthetic Construct

<400> SEQUENCE: 64
acacaggaag agacagcatg tgagtttcca gtgtcaccgt gtctcttcct gtgt      54

<210> SEQ ID NO 65
<211> LENGTH: 55
<212> TYPE: DNA
<213> ORGANISM: Artificial Sequence
<220> FEATURE:
<223> OTHER INFORMATION: Synthetic Construct

<400> SEQUENCE: 65
acacaggaag agacactgtt cttcctgaaa gactgcgcct tgtctcttcc tgtgt     55

<210> SEQ ID NO 66
<211> LENGTH: 55
<212> TYPE: DNA
<213> ORGANISM: Artificial Sequence
<220> FEATURE:
<223> OTHER INFORMATION: Synthetic Construct

<400> SEQUENCE: 66
acacaggaag agacactgtt caacctgatt gactgcgcct tgtctcttcc tgtgt     55

<210> SEQ ID NO 67
<211> LENGTH: 54
<212> TYPE: DNA
<213> ORGANISM: Artificial Sequence
<220> FEATURE:
<223> OTHER INFORMATION: Synthetic Construct

<400> SEQUENCE: 67
acacaggaag agacacgggt aacgtcaatg agcaaaggtt gtctcttcct gtgt      54

```
<210> SEQ ID NO 68
<211> LENGTH: 54
<212> TYPE: DNA
<213> ORGANISM: Artificial Sequence
<220> FEATURE:
<223> OTHER INFORMATION: Synthetic Construct

<400> SEQUENCE: 68
acacaggaag agacacagcc tacacgctta aaccgggact gtctcttcct gtgt        54

<210> SEQ ID NO 69
<211> LENGTH: 54
<212> TYPE: DNA
<213> ORGANISM: Artificial Sequence
<220> FEATURE:
<223> OTHER INFORMATION: Synthetic Construct

<400> SEQUENCE: 69
acacaggaag agacacatct cggggcaagt ttcgtgcttt gtctcttcct gtgt        54

<210> SEQ ID NO 70
<211> LENGTH: 54
<212> TYPE: DNA
<213> ORGANISM: Artificial Sequence
<220> FEATURE:
<223> OTHER INFORMATION: Synthetic Construct

<400> SEQUENCE: 70
acacaggaag agacactcaa gcttgccagt atcagatgct gtctcttcct gtgt        54

<210> SEQ ID NO 71
<211> LENGTH: 54
<212> TYPE: DNA
<213> ORGANISM: Artificial Sequence
<220> FEATURE:
<223> OTHER INFORMATION: Synthetic Construct

<400> SEQUENCE: 71
acacaggaag agacatgagc atcgttaaag tatgccggtt gtctcttcct gtgt        54

<210> SEQ ID NO 72
<211> LENGTH: 54
<212> TYPE: DNA
<213> ORGANISM: Artificial Sequence
<220> FEATURE:
<223> OTHER INFORMATION: Synthetic Construct

<400> SEQUENCE: 72
acacaggaag agacaacaac accggtgaaa tgttcttcat gtctcttcct gtgt        54

<210> SEQ ID NO 73
<211> LENGTH: 54
<212> TYPE: DNA
<213> ORGANISM: Artificial Sequence
<220> FEATURE:
<223> OTHER INFORMATION: Synthetic Construct

<400> SEQUENCE: 73
acacaggaag agacataacc cagaacaact acggaaccgt gtctcttcct gtgt        54

<210> SEQ ID NO 74
<211> LENGTH: 54
<212> TYPE: DNA
<213> ORGANISM: Artificial Sequence
<220> FEATURE:
<223> OTHER INFORMATION: Synthetic Construct
```

-continued

<400> SEQUENCE: 74
acacaggaag agacatagct ttgcactgtt tcagacccat gtctcttcct gtgt       54

<210> SEQ ID NO 75
<211> LENGTH: 54
<212> TYPE: DNA
<213> ORGANISM: Artificial Sequence
<220> FEATURE:
<223> OTHER INFORMATION: Synthetic Construct

<400> SEQUENCE: 75
acacaggaag agacacaatt ttcggaccgt agaaagcgct gtctcttcct gtgt       54

<210> SEQ ID NO 76
<211> LENGTH: 55
<212> TYPE: DNA
<213> ORGANISM: Artificial Sequence
<220> FEATURE:
<223> OTHER INFORMATION: Synthetic Construct

<400> SEQUENCE: 76
acacaggaag agacaactgt tatgcggtat tagcacctgt tgtctcttcc tgtgt      55

<210> SEQ ID NO 77
<211> LENGTH: 54
<212> TYPE: DNA
<213> ORGANISM: Artificial Sequence
<220> FEATURE:
<223> OTHER INFORMATION: Synthetic Construct

<400> SEQUENCE: 77
acacaggaag agacaaacat ttcacaacac gagctgacgt gtctcttcct gtgt       54

<210> SEQ ID NO 78
<211> LENGTH: 54
<212> TYPE: DNA
<213> ORGANISM: Artificial Sequence
<220> FEATURE:
<223> OTHER INFORMATION: Synthetic Construct

<400> SEQUENCE: 78
acacaggaag agacaaacat tctacaaacc gagctgacgt gtctcttcct gtgt       54

<210> SEQ ID NO 79
<211> LENGTH: 54
<212> TYPE: DNA
<213> ORGANISM: Artificial Sequence
<220> FEATURE:
<223> OTHER INFORMATION: Synthetic Construct

<400> SEQUENCE: 79
acacaggaag agacacttgc gacgttatgc ggtattagct gtctcttcct gtgt       54

<210> SEQ ID NO 80
<211> LENGTH: 54
<212> TYPE: DNA
<213> ORGANISM: Artificial Sequence
<220> FEATURE:
<223> OTHER INFORMATION: Synthetic Construct

<400> SEQUENCE: 80
acacaggaag agacacatca ggcttgcgcc cattgtgtct gtctcttcct gtgt       54

<210> SEQ ID NO 81

```
<211> LENGTH: 51
<212> TYPE: DNA
<213> ORGANISM: Artificial Sequence
<220> FEATURE:
<223> OTHER INFORMATION: Synthetic Construct

<400> SEQUENCE: 81
acacaggaag agacacggct gctggcacgg agttagtgtc tcttcctgtg t          51

<210> SEQ ID NO 82
<211> LENGTH: 56
<212> TYPE: DNA
<213> ORGANISM: Artificial Sequence
<220> FEATURE:
<223> OTHER INFORMATION: Synthetic Construct

<400> SEQUENCE: 82
acacaggaag agacaccagg gtatctaatc ctgtttgctc ctgtctcttc ctgtgt     56

<210> SEQ ID NO 83
<211> LENGTH: 56
<212> TYPE: DNA
<213> ORGANISM: Artificial Sequence
<220> FEATURE:
<223> OTHER INFORMATION: Synthetic Construct

<400> SEQUENCE: 83
acacaggaag agacaccagg gtttctacta ctgtttgctc ctgtctcttc ctgtgt     56

<210> SEQ ID NO 84
<211> LENGTH: 53
<212> TYPE: DNA
<213> ORGANISM: Artificial Sequence
<220> FEATURE:
<223> OTHER INFORMATION: Synthetic Construct

<400> SEQUENCE: 84
acacaggaag agacataaaa ctcaaaggaa ttgacgggtg tctcttcctg tgt        53

<210> SEQ ID NO 85
<211> LENGTH: 53
<212> TYPE: DNA
<213> ORGANISM: Artificial Sequence
<220> FEATURE:
<223> OTHER INFORMATION: Synthetic Construct

<400> SEQUENCE: 85
acacaggaag agacataaaa ctcttatgaa aagacgggtg tctcttcctg tgt        53

<210> SEQ ID NO 86
<211> LENGTH: 53
<212> TYPE: DNA
<213> ORGANISM: Artificial Sequence
<220> FEATURE:
<223> OTHER INFORMATION: Synthetic Construct

<400> SEQUENCE: 86
acacaggaag agacataaaa ctcaaatgaa ttgacgggtg tctcttcctg tgt        53

<210> SEQ ID NO 87
<211> LENGTH: 53
<212> TYPE: DNA
<213> ORGANISM: Artificial Sequence
<220> FEATURE:
<223> OTHER INFORMATION: Synthetic Construct

<400> SEQUENCE: 87
```
acacaggaag agacataaaa ctcttaggaa aagacgggtg tctcttcctg tgt    53

<210> SEQ ID NO 88
<211> LENGTH: 54
<212> TYPE: DNA
<213> ORGANISM: Artificial Sequence
<220> FEATURE:
<223> OTHER INFORMATION: Synthetic Construct

<400> SEQUENCE: 88
acacaggaag agacacagtg aaagctacaa ttccacccct gtctcttcct gtgt    54

<210> SEQ ID NO 89
<211> LENGTH: 56
<212> TYPE: DNA
<213> ORGANISM: Artificial Sequence
<220> FEATURE:
<223> OTHER INFORMATION: Synthetic Construct

<400> SEQUENCE: 89
acacaggaag agacaggttc aatgcgagat ttggacttga ctgtctcttc ctgtgt    56

<210> SEQ ID NO 90
<211> LENGTH: 54
<212> TYPE: DNA
<213> ORGANISM: Artificial Sequence
<220> FEATURE:
<223> OTHER INFORMATION: Synthetic Construct

<400> SEQUENCE: 90
acacaggaag agacattggt gcatgtattg agccagcatt gtctcttcct gtgt    54

<210> SEQ ID NO 91
<211> LENGTH: 54
<212> TYPE: DNA
<213> ORGANISM: Artificial Sequence
<220> FEATURE:
<223> OTHER INFORMATION: Synthetic Construct

<400> SEQUENCE: 91
acacaggaag agacattgag ctccatttcc acctacatgt gtctcttcct gtgt    54

<210> SEQ ID NO 92
<211> LENGTH: 56
<212> TYPE: DNA
<213> ORGANISM: Artificial Sequence
<220> FEATURE:
<223> OTHER INFORMATION: Synthetic Construct

<400> SEQUENCE: 92
acacaggaag agacatagag tatgcaggta gtgtcaatgc atgtctcttc ctgtgt    56

<210> SEQ ID NO 93
<211> LENGTH: 54
<212> TYPE: DNA
<213> ORGANISM: Artificial Sequence
<220> FEATURE:
<223> OTHER INFORMATION: Synthetic Construct

<400> SEQUENCE: 93
acacaggaag agacaaatcc atggtgtatc ctgttcctgt gtctcttcct gtgt    54

<210> SEQ ID NO 94
<211> LENGTH: 54
<212> TYPE: DNA

```
<213> ORGANISM: Artificial Sequence
<220> FEATURE:
<223> OTHER INFORMATION: Synthetic Construct

<400> SEQUENCE: 94
acacaggaag agacaaatcc atggcctatc ctcttcctgt gtctcttcct gtgt      54

<210> SEQ ID NO 95
<211> LENGTH: 54
<212> TYPE: DNA
<213> ORGANISM: Artificial Sequence
<220> FEATURE:
<223> OTHER INFORMATION: Synthetic Construct

<400> SEQUENCE: 95
acacaggaag agacatcttc aatggtggaa cagatcttct gtctcttcct gtgt      54

<210> SEQ ID NO 96
<211> LENGTH: 54
<212> TYPE: DNA
<213> ORGANISM: Artificial Sequence
<220> FEATURE:
<223> OTHER INFORMATION: Synthetic Construct

<400> SEQUENCE: 96
acacaggaag agacatcttc aatcctgcta cagatcttct gtctcttcct gtgt      54

<210> SEQ ID NO 97
<211> LENGTH: 54
<212> TYPE: DNA
<213> ORGANISM: Artificial Sequence
<220> FEATURE:
<223> OTHER INFORMATION: Synthetic Construct

<400> SEQUENCE: 97
acacaggaag agacaaaagc aaaacccagg gatcatttct gtctcttcct gtgt      54

<210> SEQ ID NO 98
<211> LENGTH: 54
<212> TYPE: DNA
<213> ORGANISM: Artificial Sequence
<220> FEATURE:
<223> OTHER INFORMATION: Synthetic Construct

<400> SEQUENCE: 98
acacaggaag agacacggac gaacgaaatg aatcccactt gtctcttcct gtgt      54

<210> SEQ ID NO 99
<211> LENGTH: 53
<212> TYPE: DNA
<213> ORGANISM: Artificial Sequence
<220> FEATURE:
<223> OTHER INFORMATION: Synthetic Construct

<400> SEQUENCE: 99
acacaggaag agacacggac tgacgaaagg aatcccactg tctcttcctg tgt       53

<210> SEQ ID NO 100
<211> LENGTH: 54
<212> TYPE: DNA
<213> ORGANISM: Artificial Sequence
<220> FEATURE:
<223> OTHER INFORMATION: Synthetic Construct

<400> SEQUENCE: 100
acacaggaag agacacggac gaacgaaatg aatcccactt gtctcttcct gtgt      54
```

<210> SEQ ID NO 101
<211> LENGTH: 54
<212> TYPE: DNA
<213> ORGANISM: Artificial Sequence
<220> FEATURE:
<223> OTHER INFORMATION: Synthetic Construct

<400> SEQUENCE: 101
acacaggaag agacagggag actttggtcg gcaagcgggt gtctcttcct gtgt    54

<210> SEQ ID NO 102
<211> LENGTH: 54
<212> TYPE: DNA
<213> ORGANISM: Artificial Sequence
<220> FEATURE:
<223> OTHER INFORMATION: Synthetic Construct

<400> SEQUENCE: 102
acacaggaag agacagggag actaaggtcg tcaagcgggt gtctcttcct gtgt    54

<210> SEQ ID NO 103
<211> LENGTH: 55
<212> TYPE: DNA
<213> ORGANISM: Artificial Sequence
<220> FEATURE:
<223> OTHER INFORMATION: Synthetic Construct

<400> SEQUENCE: 103
acacaggaag agacatctgc attgtctccg aagaaataag tgtctcttcc tgtgt    55

<210> SEQ ID NO 104
<211> LENGTH: 55
<212> TYPE: DNA
<213> ORGANISM: Artificial Sequence
<220> FEATURE:
<223> OTHER INFORMATION: Synthetic Construct

<400> SEQUENCE: 104
acacaggaag agacatctgc attctctcgc aagaaataag tgtctcttcc tgtgt    55

<210> SEQ ID NO 105
<211> LENGTH: 53
<212> TYPE: DNA
<213> ORGANISM: Artificial Sequence
<220> FEATURE:
<223> OTHER INFORMATION: Synthetic Construct

<400> SEQUENCE: 105
acacaggaag agacatacgt ttcgacctcg gttagaagtg tctcttcctg tgt    53

<210> SEQ ID NO 106
<211> LENGTH: 54
<212> TYPE: DNA
<213> ORGANISM: Artificial Sequence
<220> FEATURE:
<223> OTHER INFORMATION: Synthetic Construct

<400> SEQUENCE: 106
acacaggaag agacacggac gaacgaaatg aatcccactt gtctcttcct gtgt    54

<210> SEQ ID NO 107
<211> LENGTH: 54
<212> TYPE: DNA
<213> ORGANISM: Artificial Sequence
<220> FEATURE:

<223> OTHER INFORMATION: Synthetic Construct

<400> SEQUENCE: 107
acacaggaag agacatctgg gcacatctga tggcatgagt gtctcttcct gtgt    54

<210> SEQ ID NO 108
<211> LENGTH: 54
<212> TYPE: DNA
<213> ORGANISM: Artificial Sequence
<220> FEATURE:
<223> OTHER INFORMATION: Synthetic Construct

<400> SEQUENCE: 108
acacaggaag agacaaccct gtaccgtcgg actttccagt gtctcttcct gtgt    54

<210> SEQ ID NO 109
<211> LENGTH: 54
<212> TYPE: DNA
<213> ORGANISM: Artificial Sequence
<220> FEATURE:
<223> OTHER INFORMATION: Synthetic Construct

<400> SEQUENCE: 109
acacaggaag agacaacacg cacagtggat cctaggcaat gtctcttcct gtgt    54

<210> SEQ ID NO 110
<211> LENGTH: 54
<212> TYPE: DNA
<213> ORGANISM: Artificial Sequence
<220> FEATURE:
<223> OTHER INFORMATION: Synthetic Construct

<400> SEQUENCE: 110
acacaggaag agacaactcg cactgtggat cctaggcaat gtctcttcct gtgt    54

<210> SEQ ID NO 111
<211> LENGTH: 54
<212> TYPE: DNA
<213> ORGANISM: Artificial Sequence
<220> FEATURE:
<223> OTHER INFORMATION: Synthetic Construct

<400> SEQUENCE: 111
acacaggaag agacatgtca caaaattctt catcatgttt gtctcttcct gtgt    54

<210> SEQ ID NO 112
<211> LENGTH: 54
<212> TYPE: DNA
<213> ORGANISM: Artificial Sequence
<220> FEATURE:
<223> OTHER INFORMATION: Synthetic Construct

<400> SEQUENCE: 112
acacaggaag agacatgtca caaaattctt catcaagatt gtctcttcct gtgt    54

<210> SEQ ID NO 113
<211> LENGTH: 54
<212> TYPE: DNA
<213> ORGANISM: Artificial Sequence
<220> FEATURE:
<223> OTHER INFORMATION: Synthetic Construct

<400> SEQUENCE: 113
acacaggaag agacacacct cttccatctg acaggcacat gtctcttcct gtgt    54

```
<210> SEQ ID NO 114
<211> LENGTH: 54
<212> TYPE: DNA
<213> ORGANISM: Artificial Sequence
<220> FEATURE:
<223> OTHER INFORMATION: Synthetic Construct

<400> SEQUENCE: 114
acacaggaag agacactcga ttgtgggaag agcatgggat gtctcttcct gtgt      54

<210> SEQ ID NO 115
<211> LENGTH: 54
<212> TYPE: DNA
<213> ORGANISM: Artificial Sequence
<220> FEATURE:
<223> OTHER INFORMATION: Synthetic Construct

<400> SEQUENCE: 115
acacaggaag agacaaaggg tcagacaacc atcacgacat gtctcttcct gtgt      54

<210> SEQ ID NO 116
<211> LENGTH: 54
<212> TYPE: DNA
<213> ORGANISM: Artificial Sequence
<220> FEATURE:
<223> OTHER INFORMATION: Synthetic Construct

<400> SEQUENCE: 116
acacaggaag agacacacct catcctactg acaggcacat gtctcttcct gtgt      54

<210> SEQ ID NO 117
<211> LENGTH: 54
<212> TYPE: DNA
<213> ORGANISM: Artificial Sequence
<220> FEATURE:
<223> OTHER INFORMATION: Synthetic Construct

<400> SEQUENCE: 117
acacaggaag agacactcga tagtggagag agcatgggat gtctcttcct gtgt      54

<210> SEQ ID NO 118
<211> LENGTH: 54
<212> TYPE: DNA
<213> ORGANISM: Artificial Sequence
<220> FEATURE:
<223> OTHER INFORMATION: Synthetic Construct

<400> SEQUENCE: 118
acacaggaag agacaatggg tctgacaacc atctcgacat gtctcttcct gtgt      54

<210> SEQ ID NO 119
<211> LENGTH: 56
<212> TYPE: DNA
<213> ORGANISM: Artificial Sequence
<220> FEATURE:
<223> OTHER INFORMATION: Synthetic Construct

<400> SEQUENCE: 119
acacaggaag agacaactag tgatgctgtt gacaatttca ttgtctcttc ctgtgt    56

<210> SEQ ID NO 120
<211> LENGTH: 54
<212> TYPE: DNA
<213> ORGANISM: Artificial Sequence
<220> FEATURE:
<223> OTHER INFORMATION: Synthetic Construct
```

```
<400> SEQUENCE: 120
acacaggaag agacaggaag ggcctgggaa aacactcaat gtctcttcct gtgt         54

<210> SEQ ID NO 121
<211> LENGTH: 54
<212> TYPE: DNA
<213> ORGANISM: Artificial Sequence
<220> FEATURE:
<223> OTHER INFORMATION: Synthetic Construct

<400> SEQUENCE: 121
acacaggaag agacagagtc tgaccttgag tattcttggt gtctcttcct gtgt         54

<210> SEQ ID NO 122
<211> LENGTH: 55
<212> TYPE: DNA
<213> ORGANISM: Artificial Sequence
<220> FEATURE:
<223> OTHER INFORMATION: Synthetic Construct

<400> SEQUENCE: 122
acacaggaag agacagatga catggtctac aatgcaaaaa tgtctcttcc tgtgt        55

<210> SEQ ID NO 123
<211> LENGTH: 54
<212> TYPE: DNA
<213> ORGANISM: Artificial Sequence
<220> FEATURE:
<223> OTHER INFORMATION: Synthetic Construct

<400> SEQUENCE: 123
acacaggaag agacacatgt gatgctgttg acgaattcat gtctcttcct gtgt         54

<210> SEQ ID NO 124
<211> LENGTH: 55
<212> TYPE: DNA
<213> ORGANISM: Artificial Sequence
<220> FEATURE:
<223> OTHER INFORMATION: Synthetic Construct

<400> SEQUENCE: 124
acacaggaag agacagatga ctaggtctac atagcaataa tgtctcttcc tgtgt        55

<210> SEQ ID NO 125
<211> LENGTH: 54
<212> TYPE: DNA
<213> ORGANISM: Artificial Sequence
<220> FEATURE:
<223> OTHER INFORMATION: Synthetic Construct

<400> SEQUENCE: 125
acacaggaag agacaagaca gtcaaaatgc ctaggatcct gtctcttcct gtgt         54

<210> SEQ ID NO 126
<211> LENGTH: 54
<212> TYPE: DNA
<213> ORGANISM: Artificial Sequence
<220> FEATURE:
<223> OTHER INFORMATION: Synthetic Construct

<400> SEQUENCE: 126
acacaggaag agacactcca tttgcaactg attgatcaat gtctcttcct gtgt         54

<210> SEQ ID NO 127
<211> LENGTH: 54
```

```
<212> TYPE: DNA
<213> ORGANISM: Artificial Sequence
<220> FEATURE:
<223> OTHER INFORMATION: Synthetic Construct

<400> SEQUENCE: 127
acacaggaag agacaagaca gtacaatagc ctaggatcct gtctcttcct gtgt        54

<210> SEQ ID NO 128
<211> LENGTH: 53
<212> TYPE: DNA
<213> ORGANISM: Artificial Sequence
<220> FEATURE:
<223> OTHER INFORMATION: Synthetic Construct

<400> SEQUENCE: 128
acacaggaag agacactcca atgcaactga ttgtacattg tctcttcctg tgt         53

<210> SEQ ID NO 129
<211> LENGTH: 54
<212> TYPE: DNA
<213> ORGANISM: Artificial Sequence
<220> FEATURE:
<223> OTHER INFORMATION: Synthetic Construct

<400> SEQUENCE: 129
acacaggaag agacaaacct aggttccaca gtgcgcgaat gtctcttcct gtgt        54

<210> SEQ ID NO 130
<211> LENGTH: 54
<212> TYPE: DNA
<213> ORGANISM: Artificial Sequence
<220> FEATURE:
<223> OTHER INFORMATION: Synthetic Construct

<400> SEQUENCE: 130
acacaggaag agacaatcct aggatccact gtgcgcgaat gtctcttcct gtgt        54

<210> SEQ ID NO 131
<211> LENGTH: 52
<212> TYPE: DNA
<213> ORGANISM: Artificial Sequence
<220> FEATURE:
<223> OTHER INFORMATION: Synthetic Construct

<400> SEQUENCE: 131
acacaggaag agacaaacta tacaacctac tacctcatgt ctcttcctgt gt          52

<210> SEQ ID NO 132
<211> LENGTH: 52
<212> TYPE: DNA
<213> ORGANISM: Artificial Sequence
<220> FEATURE:
<223> OTHER INFORMATION: Synthetic Construct

<400> SEQUENCE: 132
acacaggaag agacaacaga ttcgattcta ggggaattgt ctcttcctgt gt          52

<210> SEQ ID NO 133
<211> LENGTH: 52
<212> TYPE: DNA
<213> ORGANISM: Artificial Sequence
<220> FEATURE:
<223> OTHER INFORMATION: Synthetic Construct

<400> SEQUENCE: 133
```
acacaggaag agacaagctc ccaagagcct aacccgttgt ctcttcctgt gt       52

<210> SEQ ID NO 134
<211> LENGTH: 52
<212> TYPE: DNA
<213> ORGANISM: Artificial Sequence
<220> FEATURE:
<223> OTHER INFORMATION: Synthetic Construct

<400> SEQUENCE: 134
acacaggaag agacatcaca agttagggtc tcagggatgt ctcttcctgt gt       52

<210> SEQ ID NO 135
<211> LENGTH: 52
<212> TYPE: DNA
<213> ORGANISM: Artificial Sequence
<220> FEATURE:
<223> OTHER INFORMATION: Synthetic Construct

<400> SEQUENCE: 135
acacaggaag agacacgcat tattactcac ggtacgatgt ctcttcctgt gt       52

<210> SEQ ID NO 136
<211> LENGTH: 51
<212> TYPE: DNA
<213> ORGANISM: Artificial Sequence
<220> FEATURE:
<223> OTHER INFORMATION: Synthetic Construct

<400> SEQUENCE: 136
acacaggaag agacacgcgt accaaaagta ataatgtgtc tcttcctgtg t        51

<210> SEQ ID NO 137
<211> LENGTH: 52
<212> TYPE: DNA
<213> ORGANISM: Artificial Sequence
<220> FEATURE:
<223> OTHER INFORMATION: Synthetic Construct

<400> SEQUENCE: 137
acacaggaag agacaggata tcatcatata ctgtaagtgt ctcttcctgt gt       52

<210> SEQ ID NO 138
<211> LENGTH: 52
<212> TYPE: DNA
<213> ORGANISM: Artificial Sequence
<220> FEATURE:
<223> OTHER INFORMATION: Synthetic Construct

<400> SEQUENCE: 138
acacaggaag agacatgtta atgctaatat gtaggagtgt ctcttcctgt gt       52

<210> SEQ ID NO 139
<211> LENGTH: 53
<212> TYPE: DNA
<213> ORGANISM: Artificial Sequence
<220> FEATURE:
<223> OTHER INFORMATION: Synthetic Construct

<400> SEQUENCE: 139
acacaggaag agacaacccc tatcacgatt agcattaatg tctcttcctg tgt      53

<210> SEQ ID NO 140
<211> LENGTH: 52
<212> TYPE: DNA
<213> ORGANISM: Artificial Sequence

```
<220> FEATURE:
<223> OTHER INFORMATION: Synthetic Construct

<400> SEQUENCE: 140
acacaggaag agacaccagt attaactgtg ctgctgatgt ctcttcctgt gt          52

<210> SEQ ID NO 141
<211> LENGTH: 52
<212> TYPE: DNA
<213> ORGANISM: Artificial Sequence
<220> FEATURE:
<223> OTHER INFORMATION: Synthetic Construct

<400> SEQUENCE: 141
acacaggaag agacatagca gcacgtaaat attggcgtgt ctcttcctgt gt          52

<210> SEQ ID NO 142
<211> LENGTH: 53
<212> TYPE: DNA
<213> ORGANISM: Artificial Sequence
<220> FEATURE:
<223> OTHER INFORMATION: Synthetic Construct

<400> SEQUENCE: 142
acacaggaag agacacaaag tgcttacagt gcaggtagtg tctcttcctg tgt         53

<210> SEQ ID NO 143
<211> LENGTH: 52
<212> TYPE: DNA
<213> ORGANISM: Artificial Sequence
<220> FEATURE:
<223> OTHER INFORMATION: Synthetic Construct

<400> SEQUENCE: 143
acacaggaag agacattatg gcccttcggt aattcactgt ctcttcctgt gt          52

<210> SEQ ID NO 144
<211> LENGTH: 52
<212> TYPE: DNA
<213> ORGANISM: Artificial Sequence
<220> FEATURE:
<223> OTHER INFORMATION: Synthetic Construct

<400> SEQUENCE: 144
acacaggaag agacaagtga attctaccag tgccatatgt ctcttcctgt gt          52

<210> SEQ ID NO 145
<211> LENGTH: 53
<212> TYPE: DNA
<213> ORGANISM: Artificial Sequence
<220> FEATURE:
<223> OTHER INFORMATION: Synthetic Construct

<400> SEQUENCE: 145
acacaggaag agacacaacg gaatcccaaa agcagctgtg tctcttcctg tgt         53

<210> SEQ ID NO 146
<211> LENGTH: 53
<212> TYPE: DNA
<213> ORGANISM: Artificial Sequence
<220> FEATURE:
<223> OTHER INFORMATION: Synthetic Construct

<400> SEQUENCE: 146
acacaggaag agacacaacg gaatcccaaa agcagctgtg tctcttcctg tgt         53
```

<210> SEQ ID NO 147
<211> LENGTH: 51
<212> TYPE: DNA
<213> ORGANISM: Artificial Sequence
<220> FEATURE:
<223> OTHER INFORMATION: Synthetic Construct

<400> SEQUENCE: 147
acacaggaag agacaacagc ccatcgactg gtgttgtgtc tcttcctgtg t         51

<210> SEQ ID NO 148
<211> LENGTH: 52
<212> TYPE: DNA
<213> ORGANISM: Artificial Sequence
<220> FEATURE:
<223> OTHER INFORMATION: Synthetic Construct

<400> SEQUENCE: 148
acacaggaag agacatcaac atcagtctga taagctatgt ctcttcctgt gt        52

<210> SEQ ID NO 149
<211> LENGTH: 52
<212> TYPE: DNA
<213> ORGANISM: Artificial Sequence
<220> FEATURE:
<223> OTHER INFORMATION: Synthetic Construct

<400> SEQUENCE: 149
acacaggaag agacatgcct actgagctga tatcagttgt ctcttcctgt gt        52

<210> SEQ ID NO 150
<211> LENGTH: 52
<212> TYPE: DNA
<213> ORGANISM: Artificial Sequence
<220> FEATURE:
<223> OTHER INFORMATION: Synthetic Construct

<400> SEQUENCE: 150
acacaggaag agacatggct cagttcagca ggaacagtgt ctcttcctgt gt        52

<210> SEQ ID NO 151
<211> LENGTH: 52
<212> TYPE: DNA
<213> ORGANISM: Artificial Sequence
<220> FEATURE:
<223> OTHER INFORMATION: Synthetic Construct

<400> SEQUENCE: 151
acacaggaag agacacctgt tctccattac ttggctctgt ctcttcctgt gt        52

<210> SEQ ID NO 152
<211> LENGTH: 52
<212> TYPE: DNA
<213> ORGANISM: Artificial Sequence
<220> FEATURE:
<223> OTHER INFORMATION: Synthetic Construct

<400> SEQUENCE: 152
acacaggaag agacaagagc ttagctgatt ggtgaactgt ctcttcctgt gt        52

<210> SEQ ID NO 153
<211> LENGTH: 51
<212> TYPE: DNA
<213> ORGANISM: Artificial Sequence
<220> FEATURE:
<223> OTHER INFORMATION: Synthetic Construct

<400> SEQUENCE: 153
acacaggaag agacaaggca agatgctggc atagcttgtc tcttcctgtg t        51

<210> SEQ ID NO 154
<211> LENGTH: 55
<212> TYPE: DNA
<213> ORGANISM: Artificial Sequence
<220> FEATURE:
<223> OTHER INFORMATION: Synthetic Construct

<400> SEQUENCE: 154
acacaggaag agacaaaggg aggaggagcg gaggggccct tgtctcttcc tgtgt     55

<210> SEQ ID NO 155
<211> LENGTH: 51
<212> TYPE: DNA
<213> ORGANISM: Artificial Sequence
<220> FEATURE:
<223> OTHER INFORMATION: Synthetic Construct

<400> SEQUENCE: 155
acacaggaag agacaaaggc agggcccccg ctccctgtc tcttcctgtg t          51

<210> SEQ ID NO 156
<211> LENGTH: 52
<212> TYPE: DNA
<213> ORGANISM: Artificial Sequence
<220> FEATURE:
<223> OTHER INFORMATION: Synthetic Construct

<400> SEQUENCE: 156
acacaggaag agacacatat tggcactgca catgatttgt ctcttcctgt gt        52

<210> SEQ ID NO 157
<211> LENGTH: 53
<212> TYPE: DNA
<213> ORGANISM: Artificial Sequence
<220> FEATURE:
<223> OTHER INFORMATION: Synthetic Construct

<400> SEQUENCE: 157
acacaggaag agacaagcaa aaatgtgcta gtgccaaatg tctcttcctg tgt       53

<210> SEQ ID NO 158
<211> LENGTH: 54
<212> TYPE: DNA
<213> ORGANISM: Artificial Sequence
<220> FEATURE:
<223> OTHER INFORMATION: Synthetic Construct

<400> SEQUENCE: 158
acacaggaag agacatcgct tccctttgta tacgccattt gtctcttcct gtgt      54

<210> SEQ ID NO 159
<211> LENGTH: 55
<212> TYPE: DNA
<213> ORGANISM: Artificial Sequence
<220> FEATURE:
<223> OTHER INFORMATION: Synthetic Construct

<400> SEQUENCE: 159
acacaggaag agacacgtcg cccggatgat ttagctttct tgtctcttcc tgtgt     55

<210> SEQ ID NO 160

```
<211> LENGTH: 54
<212> TYPE: DNA
<213> ORGANISM: Artificial Sequence
<220> FEATURE:
<223> OTHER INFORMATION: Synthetic Construct

<400> SEQUENCE: 160
acacaggaag agacatgata gaacaaataa ccggatcgct gtctcttcct gtgt      54

<210> SEQ ID NO 161
<211> LENGTH: 54
<212> TYPE: DNA
<213> ORGANISM: Artificial Sequence
<220> FEATURE:
<223> OTHER INFORMATION: Synthetic Construct

<400> SEQUENCE: 161
acacaggaag agacagggat ttcacatcca acttgctgat gtctcttcct gtgt      54

<210> SEQ ID NO 162
<211> LENGTH: 54
<212> TYPE: DNA
<213> ORGANISM: Artificial Sequence
<220> FEATURE:
<223> OTHER INFORMATION: Synthetic Construct

<400> SEQUENCE: 162
acacaggaag agacagctac cacgtctttc atcgcctctt gtctcttcct gtgt      54

<210> SEQ ID NO 163
<211> LENGTH: 54
<212> TYPE: DNA
<213> ORGANISM: Artificial Sequence
<220> FEATURE:
<223> OTHER INFORMATION: Synthetic Construct

<400> SEQUENCE: 163
acacaggaag agacatgact taattgaccg cctgcgtgct gtctcttcct gtgt      54

<210> SEQ ID NO 164
<211> LENGTH: 54
<212> TYPE: DNA
<213> ORGANISM: Artificial Sequence
<220> FEATURE:
<223> OTHER INFORMATION: Synthetic Construct

<400> SEQUENCE: 164
acacaggaag agacacatgc ttagccaacc ttcgtgctct gtctcttcct gtgt      54

<210> SEQ ID NO 165
<211> LENGTH: 54
<212> TYPE: DNA
<213> ORGANISM: Artificial Sequence
<220> FEATURE:
<223> OTHER INFORMATION: Synthetic Construct

<400> SEQUENCE: 165
acacaggaag agacaacttt ccagaccgtt ctcctgacat gtctcttcct gtgt      54

<210> SEQ ID NO 166
<211> LENGTH: 54
<212> TYPE: DNA
<213> ORGANISM: Artificial Sequence
<220> FEATURE:
<223> OTHER INFORMATION: Synthetic Construct

<400> SEQUENCE: 166
```
acacaggaag agacatagta caccacgcac caattacatt gtctcttcct gtgt         54

<210> SEQ ID NO 167
<211> LENGTH: 55
<212> TYPE: DNA
<213> ORGANISM: Artificial Sequence
<220> FEATURE:
<223> OTHER INFORMATION: Synthetic Construct

<400> SEQUENCE: 167
acacaggaag agacaaagag aatcctccga tatctagcac tgtctcttcc tgtgt        55

<210> SEQ ID NO 168
<211> LENGTH: 55
<212> TYPE: DNA
<213> ORGANISM: Artificial Sequence
<220> FEATURE:
<223> OTHER INFORMATION: Synthetic Construct

<400> SEQUENCE: 168
acacaggaag agacaaagac aatccctcga tatctagcac tgtctcttcc tgtgt        55

<210> SEQ ID NO 169
<211> LENGTH: 54
<212> TYPE: DNA
<213> ORGANISM: Artificial Sequence
<220> FEATURE:
<223> OTHER INFORMATION: Synthetic Construct

<400> SEQUENCE: 169
acacaggaag agacaaatcc ataaccacca tgtcaagggt gtctcttcct gtgt         54

<210> SEQ ID NO 170
<211> LENGTH: 54
<212> TYPE: DNA
<213> ORGANISM: Artificial Sequence
<220> FEATURE:
<223> OTHER INFORMATION: Synthetic Construct

<400> SEQUENCE: 170
acacaggaag agacaaatcc ataaccacca tggcaacggt gtctcttcct gtgt         54

<210> SEQ ID NO 171
<211> LENGTH: 54
<212> TYPE: DNA
<213> ORGANISM: Artificial Sequence
<220> FEATURE:
<223> OTHER INFORMATION: Synthetic Construct

<400> SEQUENCE: 171
acacaggaag agacactcca gcaaacctta cagtttacct gtctcttcct gtgt         54

<210> SEQ ID NO 172
<211> LENGTH: 54
<212> TYPE: DNA
<213> ORGANISM: Artificial Sequence
<220> FEATURE:
<223> OTHER INFORMATION: Synthetic Construct

<400> SEQUENCE: 172
acacaggaag agacactcca gcttacctat cagtaaacct gtctcttcct gtgt         54

<210> SEQ ID NO 173
<211> LENGTH: 54
<212> TYPE: DNA

```
<213> ORGANISM: Artificial Sequence
<220> FEATURE:
<223> OTHER INFORMATION: Synthetic Construct

<400> SEQUENCE: 173
acacaggaag agacacacct gcacatggtt gcccacacgt gtctcttcct gtgt      54

<210> SEQ ID NO 174
<211> LENGTH: 54
<212> TYPE: DNA
<213> ORGANISM: Artificial Sequence
<220> FEATURE:
<223> OTHER INFORMATION: Synthetic Construct

<400> SEQUENCE: 174
acacaggaag agacacacca gcactaggtt gcccacacgt gtctcttcct gtgt      54

<210> SEQ ID NO 175
<211> LENGTH: 54
<212> TYPE: DNA
<213> ORGANISM: Artificial Sequence
<220> FEATURE:
<223> OTHER INFORMATION: Synthetic Construct

<400> SEQUENCE: 175
acacaggaag agacatatca ccctctatgg tcaatctttt gtctcttcct gtgt      54

<210> SEQ ID NO 176
<211> LENGTH: 54
<212> TYPE: DNA
<213> ORGANISM: Artificial Sequence
<220> FEATURE:
<223> OTHER INFORMATION: Synthetic Construct

<400> SEQUENCE: 176
acacaggaag agacatatct ccctcaatgg acaatctttt gtctcttcct gtgt      54

<210> SEQ ID NO 177
<211> LENGTH: 54
<212> TYPE: DNA
<213> ORGANISM: Artificial Sequence
<220> FEATURE:
<223> OTHER INFORMATION: Synthetic Construct

<400> SEQUENCE: 177
acacaggaag agacaaaggt acgccgtcac aagacataat gtctcttcct gtgt      54

<210> SEQ ID NO 178
<211> LENGTH: 54
<212> TYPE: DNA
<213> ORGANISM: Artificial Sequence
<220> FEATURE:
<223> OTHER INFORMATION: Synthetic Construct

<400> SEQUENCE: 178
acacaggaag agacaaaggt acgccgacac tagtcataat gtctcttcct gtgt      54

<210> SEQ ID NO 179
<211> LENGTH: 54
<212> TYPE: DNA
<213> ORGANISM: Artificial Sequence
<220> FEATURE:
<223> OTHER INFORMATION: Synthetic Construct

<400> SEQUENCE: 179
acacaggaag agacacagcg gattttactc cactttcaat gtctcttcct gtgt      54
```

<210> SEQ ID NO 180
<211> LENGTH: 54
<212> TYPE: DNA
<213> ORGANISM: Artificial Sequence
<220> FEATURE:
<223> OTHER INFORMATION: Synthetic Construct

<400> SEQUENCE: 180
acacaggaag agacacagcg gttttatcac cactttcaat gtctcttcct gtgt    54

<210> SEQ ID NO 181
<211> LENGTH: 54
<212> TYPE: DNA
<213> ORGANISM: Artificial Sequence
<220> FEATURE:
<223> OTHER INFORMATION: Synthetic Construct

<400> SEQUENCE: 181
acacaggaag agacaccatt cgccacggtc acgaaccatt gtctcttcct gtgt    54

<210> SEQ ID NO 182
<211> LENGTH: 55
<212> TYPE: DNA
<213> ORGANISM: Artificial Sequence
<220> FEATURE:
<223> OTHER INFORMATION: Synthetic Construct

<400> SEQUENCE: 182
acacaggaag agacatggaa gaaacgattc atgtgccagt tgtctcttcc tgtgt    55

<210> SEQ ID NO 183
<211> LENGTH: 54
<212> TYPE: DNA
<213> ORGANISM: Artificial Sequence
<220> FEATURE:
<223> OTHER INFORMATION: Synthetic Construct

<400> SEQUENCE: 183
acacaggaag agacagttct gcagtaccgg atttgccaat gtctcttcct gtgt    54

<210> SEQ ID NO 184
<211> LENGTH: 54
<212> TYPE: DNA
<213> ORGANISM: Artificial Sequence
<220> FEATURE:
<223> OTHER INFORMATION: Synthetic Construct

<400> SEQUENCE: 184
acacaggaag agacatcgcc tctaaatcgc tcaaagtgtt gtctcttcct gtgt    54

<210> SEQ ID NO 185
<211> LENGTH: 54
<212> TYPE: DNA
<213> ORGANISM: Artificial Sequence
<220> FEATURE:
<223> OTHER INFORMATION: Synthetic Construct

<400> SEQUENCE: 185
acacaggaag agacaagctg accaccacca ataatgccat gtctcttcct gtgt    54

<210> SEQ ID NO 186
<211> LENGTH: 54
<212> TYPE: DNA
<213> ORGANISM: Artificial Sequence
<220> FEATURE:

```
<223> OTHER INFORMATION: Synthetic Construct

<400> SEQUENCE: 186
acacaggaag agacaagtga agcacgaacc gttcgaccat gtctcttcct gtgt        54

<210> SEQ ID NO 187
<211> LENGTH: 54
<212> TYPE: DNA
<213> ORGANISM: Artificial Sequence
<220> FEATURE:
<223> OTHER INFORMATION: Synthetic Construct

<400> SEQUENCE: 187
acacaggaag agacataaat gctgccaccc cgccattact gtctcttcct gtgt        54

<210> SEQ ID NO 188
<211> LENGTH: 54
<212> TYPE: DNA
<213> ORGANISM: Artificial Sequence
<220> FEATURE:
<223> OTHER INFORMATION: Synthetic Construct

<400> SEQUENCE: 188
acacaggaag agacagcaag accgtctttc acttttgaat gtctcttcct gtgt        54

<210> SEQ ID NO 189
<211> LENGTH: 54
<212> TYPE: DNA
<213> ORGANISM: Artificial Sequence
<220> FEATURE:
<223> OTHER INFORMATION: Synthetic Construct

<400> SEQUENCE: 189
acacaggaag agacaactag ctaatgcagc gcggatccat gtctcttcct gtgt        54

<210> SEQ ID NO 190
<211> LENGTH: 54
<212> TYPE: DNA
<213> ORGANISM: Artificial Sequence
<220> FEATURE:
<223> OTHER INFORMATION: Synthetic Construct

<400> SEQUENCE: 190
acacaggaag agacagttac ttacacatat gttcttccct gtctcttcct gtgt        54

<210> SEQ ID NO 191
<211> LENGTH: 54
<212> TYPE: DNA
<213> ORGANISM: Artificial Sequence
<220> FEATURE:
<223> OTHER INFORMATION: Synthetic Construct

<400> SEQUENCE: 191
acacaggaag agacacactt tagcatctct gccaaattct gtctcttcct gtgt        54

<210> SEQ ID NO 192
<211> LENGTH: 54
<212> TYPE: DNA
<213> ORGANISM: Artificial Sequence
<220> FEATURE:
<223> OTHER INFORMATION: Synthetic Construct

<400> SEQUENCE: 192
acacaggaag agacacacaa tagcatctct gccattttct gtctcttcct gtgt        54
```

```
<210> SEQ ID NO 193
<211> LENGTH: 54
<212> TYPE: DNA
<213> ORGANISM: Artificial Sequence
<220> FEATURE:
<223> OTHER INFORMATION: Synthetic Construct

<400> SEQUENCE: 193
acacaggaag agacattcgc ttcactttgt atctgccatt gtctcttcct gtgt        54

<210> SEQ ID NO 194
<211> LENGTH: 54
<212> TYPE: DNA
<213> ORGANISM: Artificial Sequence
<220> FEATURE:
<223> OTHER INFORMATION: Synthetic Construct

<400> SEQUENCE: 194
acacaggaag agacattcgc ttctctctgt ttctgccatt gtctcttcct gtgt        54

<210> SEQ ID NO 195
<211> LENGTH: 54
<212> TYPE: DNA
<213> ORGANISM: Artificial Sequence
<220> FEATURE:
<223> OTHER INFORMATION: Synthetic Construct

<400> SEQUENCE: 195
acacaggaag agacatacga cagactttat gtggtccgct gtctcttcct gtgt        54

<210> SEQ ID NO 196
<211> LENGTH: 54
<212> TYPE: DNA
<213> ORGANISM: Artificial Sequence
<220> FEATURE:
<223> OTHER INFORMATION: Synthetic Construct

<400> SEQUENCE: 196
acacaggaag agacatacga cagtcttaat gaggtccgct gtctcttcct gtgt        54

<210> SEQ ID NO 197
<211> LENGTH: 54
<212> TYPE: DNA
<213> ORGANISM: Artificial Sequence
<220> FEATURE:
<223> OTHER INFORMATION: Synthetic Construct

<400> SEQUENCE: 197
acacaggaag agacacgtca atgattgagc gtattaaact gtctcttcct gtgt        54

<210> SEQ ID NO 198
<211> LENGTH: 54
<212> TYPE: DNA
<213> ORGANISM: Artificial Sequence
<220> FEATURE:
<223> OTHER INFORMATION: Synthetic Construct

<400> SEQUENCE: 198
acacaggaag agacacgtca atgattgagc gaatataact gtctcttcct gtgt        54

<210> SEQ ID NO 199
<211> LENGTH: 54
<212> TYPE: DNA
<213> ORGANISM: Artificial Sequence
<220> FEATURE:
<223> OTHER INFORMATION: Synthetic Construct
```

<400> SEQUENCE: 199
acacaggaag agacaggtat cgtcggttat aacgcttcat gtctcttcct gtgt    54

<210> SEQ ID NO 200
<211> LENGTH: 54
<212> TYPE: DNA
<213> ORGANISM: Artificial Sequence
<220> FEATURE:
<223> OTHER INFORMATION: Synthetic Construct

<400> SEQUENCE: 200
acacaggaag agacaggtat cgacggtaat atcgcttcat gtctcttcct gtgt    54

<210> SEQ ID NO 201
<211> LENGTH: 54
<212> TYPE: DNA
<213> ORGANISM: Artificial Sequence
<220> FEATURE:
<223> OTHER INFORMATION: Synthetic Construct

<400> SEQUENCE: 201
acacaggaag agacaaagca accggattta cctggtcact gtctcttcct gtgt    54

<210> SEQ ID NO 202
<211> LENGTH: 54
<212> TYPE: DNA
<213> ORGANISM: Artificial Sequence
<220> FEATURE:
<223> OTHER INFORMATION: Synthetic Construct

<400> SEQUENCE: 202
acacaggaag agacaaagca accggtatat cctggtcact gtctcttcct gtgt    54

<210> SEQ ID NO 203
<211> LENGTH: 54
<212> TYPE: DNA
<213> ORGANISM: Artificial Sequence
<220> FEATURE:
<223> OTHER INFORMATION: Synthetic Construct

<400> SEQUENCE: 203
acacaggaag agacaatcaa ctgcttctgc accgtggtgt gtctcttcct gtgt    54

<210> SEQ ID NO 204
<211> LENGTH: 54
<212> TYPE: DNA
<213> ORGANISM: Artificial Sequence
<220> FEATURE:
<223> OTHER INFORMATION: Synthetic Construct

<400> SEQUENCE: 204
acacaggaag agacaatcta ctgctcttgc accgaggtgt gtctcttcct gtgt    54

<210> SEQ ID NO 205
<211> LENGTH: 54
<212> TYPE: DNA
<213> ORGANISM: Artificial Sequence
<220> FEATURE:
<223> OTHER INFORMATION: Synthetic Construct

<400> SEQUENCE: 205
acacaggaag agacaagcta gtcctttcac ctaacgccat gtctcttcct gtgt    54

<210> SEQ ID NO 206
<211> LENGTH: 54

```
<212> TYPE: DNA
<213> ORGANISM: Artificial Sequence
<220> FEATURE:
<223> OTHER INFORMATION: Synthetic Construct

<400> SEQUENCE: 206
acacaggaag agacaagcta gtctcttaac ctaacgccat gtctcttcct gtgt         54

<210> SEQ ID NO 207
<211> LENGTH: 54
<212> TYPE: DNA
<213> ORGANISM: Artificial Sequence
<220> FEATURE:
<223> OTHER INFORMATION: Synthetic Construct

<400> SEQUENCE: 207
acacaggaag agacactggt tagctcaata catcgctgct gtctcttcct gtgt         54

<210> SEQ ID NO 208
<211> LENGTH: 54
<212> TYPE: DNA
<213> ORGANISM: Artificial Sequence
<220> FEATURE:
<223> OTHER INFORMATION: Synthetic Construct

<400> SEQUENCE: 208
acacaggaag agacactgga ttgctcaatt catcgctgct gtctcttcct gtgt         54

<210> SEQ ID NO 209
<211> LENGTH: 54
<212> TYPE: DNA
<213> ORGANISM: Artificial Sequence
<220> FEATURE:
<223> OTHER INFORMATION: Synthetic Construct

<400> SEQUENCE: 209
acacaggaag agacacatca gccgttggat ttgctaagct gtctcttcct gtgt         54

<210> SEQ ID NO 210
<211> LENGTH: 54
<212> TYPE: DNA
<213> ORGANISM: Artificial Sequence
<220> FEATURE:
<223> OTHER INFORMATION: Synthetic Construct

<400> SEQUENCE: 210
acacaggaag agacagatga caggtggagc agcatcttgt gtctcttcct gtgt         54

<210> SEQ ID NO 211
<211> LENGTH: 54
<212> TYPE: DNA
<213> ORGANISM: Artificial Sequence
<220> FEATURE:
<223> OTHER INFORMATION: Synthetic Construct

<400> SEQUENCE: 211
acacaggaag agacagcctt gccgaaatgg gtgatagtat gtctcttcct gtgt         54

<210> SEQ ID NO 212
<211> LENGTH: 54
<212> TYPE: DNA
<213> ORGANISM: Artificial Sequence
<220> FEATURE:
<223> OTHER INFORMATION: Synthetic Construct

<400> SEQUENCE: 212
```
acacaggaag agacagtgca cttgaaccat tgcagaggat gtctcttcct gtgt    54

<210> SEQ ID NO 213
<211> LENGTH: 54
<212> TYPE: DNA
<213> ORGANISM: Artificial Sequence
<220> FEATURE:
<223> OTHER INFORMATION: Synthetic Construct

<400> SEQUENCE: 213
acacaggaag agacaccact agatactgct ggcagcaatt gtctcttcct gtgt    54

<210> SEQ ID NO 214
<211> LENGTH: 54
<212> TYPE: DNA
<213> ORGANISM: Artificial Sequence
<220> FEATURE:
<223> OTHER INFORMATION: Synthetic Construct

<400> SEQUENCE: 214
acacaggaag agacacatat tgacaatccg gaatcctcct gtctcttcct gtgt    54

<210> SEQ ID NO 215
<211> LENGTH: 54
<212> TYPE: DNA
<213> ORGANISM: Artificial Sequence
<220> FEATURE:
<223> OTHER INFORMATION: Synthetic Construct

<400> SEQUENCE: 215
acacaggaag agacacatat tgacaatccg gtactcacct gtctcttcct gtgt    54

<210> SEQ ID NO 216
<211> LENGTH: 54
<212> TYPE: DNA
<213> ORGANISM: Artificial Sequence
<220> FEATURE:
<223> OTHER INFORMATION: Synthetic Construct

<400> SEQUENCE: 216
acacaggaag agacatgtgc cagtggtggg tgatcttctt gtctcttcct gtgt    54

<210> SEQ ID NO 217
<211> LENGTH: 54
<212> TYPE: DNA
<213> ORGANISM: Artificial Sequence
<220> FEATURE:
<223> OTHER INFORMATION: Synthetic Construct

<400> SEQUENCE: 217
acacaggaag agacatgtgc cagtggtggg tatgcttctt gtctcttcct gtgt    54

<210> SEQ ID NO 218
<211> LENGTH: 54
<212> TYPE: DNA
<213> ORGANISM: Artificial Sequence
<220> FEATURE:
<223> OTHER INFORMATION: Synthetic Construct

<400> SEQUENCE: 218
acacaggaag agacactgat ccaaagtccc aggctgtgtt gtctcttcct gtgt    54

<210> SEQ ID NO 219
<211> LENGTH: 54
<212> TYPE: DNA
<213> ORGANISM: Artificial Sequence

```
<220> FEATURE:
<223> OTHER INFORMATION: Synthetic Construct

<400> SEQUENCE: 219
acacaggaag agacaaggct agaatcgcca agaccatcct gtctcttcct gtgt        54

<210> SEQ ID NO 220
<211> LENGTH: 54
<212> TYPE: DNA
<213> ORGANISM: Artificial Sequence
<220> FEATURE:
<223> OTHER INFORMATION: Synthetic Construct

<400> SEQUENCE: 220
acacaggaag agacaagcct agatacggca agaccatcct gtctcttcct gtgt        54

<210> SEQ ID NO 221
<211> LENGTH: 54
<212> TYPE: DNA
<213> ORGANISM: Artificial Sequence
<220> FEATURE:
<223> OTHER INFORMATION: Synthetic Construct

<400> SEQUENCE: 221
acacaggaag agacactcag catggcagcc agatctttct gtctcttcct gtgt        54

<210> SEQ ID NO 222
<211> LENGTH: 54
<212> TYPE: DNA
<213> ORGANISM: Artificial Sequence
<220> FEATURE:
<223> OTHER INFORMATION: Synthetic Construct

<400> SEQUENCE: 222
acacaggaag agacacacag catgggaccc agatctttct gtctcttcct gtgt        54

<210> SEQ ID NO 223
<211> LENGTH: 54
<212> TYPE: DNA
<213> ORGANISM: Artificial Sequence
<220> FEATURE:
<223> OTHER INFORMATION: Synthetic Construct

<400> SEQUENCE: 223
acacaggaag agacacagcc aggattgcca aggtgatgtt gtctcttcct gtgt        54

<210> SEQ ID NO 224
<211> LENGTH: 54
<212> TYPE: DNA
<213> ORGANISM: Artificial Sequence
<220> FEATURE:
<223> OTHER INFORMATION: Synthetic Construct

<400> SEQUENCE: 224
acacaggaag agacactgcc aggatagcca aggtgaagtt gtctcttcct gtgt        54

<210> SEQ ID NO 225
<211> LENGTH: 54
<212> TYPE: DNA
<213> ORGANISM: Artificial Sequence
<220> FEATURE:
<223> OTHER INFORMATION: Synthetic Construct

<400> SEQUENCE: 225
acacaggaag agacagtgtt gcaccaacaa tcgacgtcat gtctcttcct gtgt        54
```

<210> SEQ ID NO 226
<211> LENGTH: 54
<212> TYPE: DNA
<213> ORGANISM: Artificial Sequence
<220> FEATURE:
<223> OTHER INFORMATION: Synthetic Construct

<400> SEQUENCE: 226
acacaggaag agacacaagt tgacgtcgtg ttgcaccaat gtctcttcct gtgt     54

<210> SEQ ID NO 227
<211> LENGTH: 54
<212> TYPE: DNA
<213> ORGANISM: Artificial Sequence
<220> FEATURE:
<223> OTHER INFORMATION: Synthetic Construct

<400> SEQUENCE: 227
acacaggaag agacagctct tctagatctc cgtgcttcat gtctcttcct gtgt     54

<210> SEQ ID NO 228
<211> LENGTH: 54
<212> TYPE: DNA
<213> ORGANISM: Artificial Sequence
<220> FEATURE:
<223> OTHER INFORMATION: Synthetic Construct

<400> SEQUENCE: 228
acacaggaag agacagctct tcatgatctc cctgctctat gtctcttcct gtgt     54

<210> SEQ ID NO 229
<211> LENGTH: 54
<212> TYPE: DNA
<213> ORGANISM: Artificial Sequence
<220> FEATURE:
<223> OTHER INFORMATION: Synthetic Construct

<400> SEQUENCE: 229
acacaggaag agacaatccg gactacgacg cactttatgt gtctcttcct gtgt     54

<210> SEQ ID NO 230
<211> LENGTH: 54
<212> TYPE: DNA
<213> ORGANISM: Artificial Sequence
<220> FEATURE:
<223> OTHER INFORMATION: Synthetic Construct

<400> SEQUENCE: 230
acacaggaag agacacatct cggggcaagt ttcgtgcttt gtctcttcct gtgt     54

<210> SEQ ID NO 231
<211> LENGTH: 55
<212> TYPE: DNA
<213> ORGANISM: Artificial Sequence
<220> FEATURE:
<223> OTHER INFORMATION: Synthetic Construct

<400> SEQUENCE: 231
acacaggaag agacattgat gttacctgat gcttagaggc tgtctcttcc tgtgt     55

<210> SEQ ID NO 232
<211> LENGTH: 54
<212> TYPE: DNA
<213> ORGANISM: Artificial Sequence
<220> FEATURE:
<223> OTHER INFORMATION: Synthetic Construct

```
<400> SEQUENCE: 232
acacaggaag agacatgtac gtacacggtt tcaggttctt gtctcttcct gtgt          54

<210> SEQ ID NO 233
<211> LENGTH: 54
<212> TYPE: DNA
<213> ORGANISM: Artificial Sequence
<220> FEATURE:
<223> OTHER INFORMATION: Synthetic Construct

<400> SEQUENCE: 233
acacaggaag agacaagtta gccggtgctt attctgttgt gtctcttcct gtgt          54

<210> SEQ ID NO 234
<211> LENGTH: 54
<212> TYPE: DNA
<213> ORGANISM: Artificial Sequence
<220> FEATURE:
<223> OTHER INFORMATION: Synthetic Construct

<400> SEQUENCE: 234
acacaggaag agacagctac cacgtctttc atcgcctctt gtctcttcct gtgt          54

<210> SEQ ID NO 235
<211> LENGTH: 54
<212> TYPE: DNA
<213> ORGANISM: Artificial Sequence
<220> FEATURE:
<223> OTHER INFORMATION: Synthetic Construct

<400> SEQUENCE: 235
acacaggaag agacaacacg cacagtggat cctaggcaat gtctcttcct gtgt          54

<210> SEQ ID NO 236
<211> LENGTH: 54
<212> TYPE: DNA
<213> ORGANISM: Artificial Sequence
<220> FEATURE:
<223> OTHER INFORMATION: Synthetic Construct

<400> SEQUENCE: 236
acacaggaag agacacatcg tttaccactt aaccacaact gtctcttcct gtgt          54

<210> SEQ ID NO 237
<211> LENGTH: 54
<212> TYPE: DNA
<213> ORGANISM: Artificial Sequence
<220> FEATURE:
<223> OTHER INFORMATION: Synthetic Construct

<400> SEQUENCE: 237
acacaggaag agacagttcc gctaaaatca atgaagcttt gtctcttcct gtgt          54

<210> SEQ ID NO 238
<211> LENGTH: 54
<212> TYPE: DNA
<213> ORGANISM: Artificial Sequence
<220> FEATURE:
<223> OTHER INFORMATION: Synthetic Construct

<400> SEQUENCE: 238
acacaggaag agacaagcag cttcggtgtg tggtttgagt gtctcttcct gtgt          54

<210> SEQ ID NO 239
```

```
<211> LENGTH: 56
<212> TYPE: DNA
<213> ORGANISM: Artificial Sequence
<220> FEATURE:
<223> OTHER INFORMATION: Synthetic Construct

<400> SEQUENCE: 239
acacaggaag agacacatcg cagtaaccag aagtacagga atgtctcttc ctgtgt          56

<210> SEQ ID NO 240
<211> LENGTH: 54
<212> TYPE: DNA
<213> ORGANISM: Artificial Sequence
<220> FEATURE:
<223> OTHER INFORMATION: Synthetic Construct

<400> SEQUENCE: 240
acacaggaag agacatgact taattgaccg cctgcgtgct gtctcttcct gtgt            54

<210> SEQ ID NO 241
<211> LENGTH: 54
<212> TYPE: DNA
<213> ORGANISM: Artificial Sequence
<220> FEATURE:
<223> OTHER INFORMATION: Synthetic Construct

<400> SEQUENCE: 241
acacaggaag agacaggatt cgctggatgt caagagtagt gtctcttcct gtgt            54

<210> SEQ ID NO 242
<211> LENGTH: 54
<212> TYPE: DNA
<213> ORGANISM: Artificial Sequence
<220> FEATURE:
<223> OTHER INFORMATION: Synthetic Construct

<400> SEQUENCE: 242
acacaggaag agacacacgg tccccgaccc agtttatgat gtctcttcct gtgt            54

<210> SEQ ID NO 243
<211> LENGTH: 54
<212> TYPE: DNA
<213> ORGANISM: Artificial Sequence
<220> FEATURE:
<223> OTHER INFORMATION: Synthetic Construct

<400> SEQUENCE: 243
acacaggaag agacaacttt ccagaccgtt ctcctgacat gtctcttcct gtgt            54

<210> SEQ ID NO 244
<211> LENGTH: 54
<212> TYPE: DNA
<213> ORGANISM: Artificial Sequence
<220> FEATURE:
<223> OTHER INFORMATION: Synthetic Construct

<400> SEQUENCE: 244
acacaggaag agacagggac tttacctacc gccagcgtat gtctcttcct gtgt            54

<210> SEQ ID NO 245
<211> LENGTH: 54
<212> TYPE: DNA
<213> ORGANISM: Artificial Sequence
<220> FEATURE:
<223> OTHER INFORMATION: Synthetic Construct

<400> SEQUENCE: 245
```
acacaggaag agacattcgg tgttgtcagg ttaagcctct gtctcttcct gtgt        54

<210> SEQ ID NO 246
<211> LENGTH: 54
<212> TYPE: DNA
<213> ORGANISM: Artificial Sequence
<220> FEATURE:
<223> OTHER INFORMATION: Synthetic Construct

<400> SEQUENCE: 246
acacaggaag agacatctgg gcacatctga tggcatgagt gtctcttcct gtgt        54

<210> SEQ ID NO 247
<211> LENGTH: 54
<212> TYPE: DNA
<213> ORGANISM: Artificial Sequence
<220> FEATURE:
<223> OTHER INFORMATION: Synthetic Construct

<400> SEQUENCE: 247
acacaggaag agacaaagtt ctgtggatgt caagaccagt gtctcttcct gtgt        54

<210> SEQ ID NO 248
<211> LENGTH: 54
<212> TYPE: DNA
<213> ORGANISM: Artificial Sequence
<220> FEATURE:
<223> OTHER INFORMATION: Synthetic Construct

<400> SEQUENCE: 248
acacaggaag agacaccctta ccgacgcttt tcgcagattt gtctcttcct gtgt       54

<210> SEQ ID NO 249
<211> LENGTH: 54
<212> TYPE: DNA
<213> ORGANISM: Artificial Sequence
<220> FEATURE:
<223> OTHER INFORMATION: Synthetic Construct

<400> SEQUENCE: 249
acacaggaag agacagaccg ttccactaac acacaagctt gtctcttcct gtgt        54

<210> SEQ ID NO 250
<211> LENGTH: 54
<212> TYPE: DNA
<213> ORGANISM: Artificial Sequence
<220> FEATURE:
<223> OTHER INFORMATION: Synthetic Construct

<400> SEQUENCE: 250
acacaggaag agacactggt atcttcgact ggtctcagct gtctcttcct gtgt        54

<210> SEQ ID NO 251
<211> LENGTH: 54
<212> TYPE: DNA
<213> ORGANISM: Artificial Sequence
<220> FEATURE:
<223> OTHER INFORMATION: Synthetic Construct

<400> SEQUENCE: 251
acacaggaag agacaccacg ctcgcagtca agctagcttt gtctcttcct gtgt        54

<210> SEQ ID NO 252
<211> LENGTH: 54
<212> TYPE: DNA

```
<213> ORGANISM: Artificial Sequence
<220> FEATURE:
<223> OTHER INFORMATION: Synthetic Construct

<400> SEQUENCE: 252
acacaggaag agacatatgg gttcatctga tggcgcgagt gtctcttcct gtgt         54

<210> SEQ ID NO 253
<211> LENGTH: 54
<212> TYPE: DNA
<213> ORGANISM: Artificial Sequence
<220> FEATURE:
<223> OTHER INFORMATION: Synthetic Construct

<400> SEQUENCE: 253
acacaggaag agacaatctg actcaatcaa ccgcctgcgt gtctcttcct gtgt         54

<210> SEQ ID NO 254
<211> LENGTH: 54
<212> TYPE: DNA
<213> ORGANISM: Artificial Sequence
<220> FEATURE:
<223> OTHER INFORMATION: Synthetic Construct

<400> SEQUENCE: 254
acacaggaag agacacatcc accgtgtacg cttattcgct gtctcttcct gtgt         54

<210> SEQ ID NO 255
<211> LENGTH: 54
<212> TYPE: DNA
<213> ORGANISM: Artificial Sequence
<220> FEATURE:
<223> OTHER INFORMATION: Synthetic Construct

<400> SEQUENCE: 255
acacaggaag agacactccc ggttcgcttc attaccctat gtctcttcct gtgt         54

<210> SEQ ID NO 256
<211> LENGTH: 54
<212> TYPE: DNA
<213> ORGANISM: Artificial Sequence
<220> FEATURE:
<223> OTHER INFORMATION: Synthetic Construct

<400> SEQUENCE: 256
acacaggaag agacatcccg gaagcagagc atcaatcact gtctcttcct gtgt         54

<210> SEQ ID NO 257
<211> LENGTH: 54
<212> TYPE: DNA
<213> ORGANISM: Artificial Sequence
<220> FEATURE:
<223> OTHER INFORMATION: Synthetic Construct

<400> SEQUENCE: 257
acacaggaag agacatatgt tcttccctaa taacagagtt gtctcttcct gtgt         54

<210> SEQ ID NO 258
<211> LENGTH: 55
<212> TYPE: DNA
<213> ORGANISM: Artificial Sequence
<220> FEATURE:
<223> OTHER INFORMATION: Synthetic Construct

<400> SEQUENCE: 258
acacaggaag agacactaga gttgtcaaag gatgtcaaga tgtctcttcc tgtgt        55
```

```
<210> SEQ ID NO 259
<211> LENGTH: 54
<212> TYPE: DNA
<213> ORGANISM: Artificial Sequence
<220> FEATURE:
<223> OTHER INFORMATION: Synthetic Construct

<400> SEQUENCE: 259
acacaggaag agacaaggat ccactcaaga gagacaacat gtctcttcct gtgt      54

<210> SEQ ID NO 260
<211> LENGTH: 54
<212> TYPE: DNA
<213> ORGANISM: Artificial Sequence
<220> FEATURE:
<223> OTHER INFORMATION: Synthetic Construct

<400> SEQUENCE: 260
acacaggaag agacattcct taacgagagt tcgctcgctt gtctcttcct gtgt      54

<210> SEQ ID NO 261
<211> LENGTH: 54
<212> TYPE: DNA
<213> ORGANISM: Artificial Sequence
<220> FEATURE:
<223> OTHER INFORMATION: Synthetic Construct

<400> SEQUENCE: 261
acacaggaag agacaagctg tgccgaattt caatatcagt gtctcttcct gtgt      54

<210> SEQ ID NO 262
<211> LENGTH: 54
<212> TYPE: DNA
<213> ORGANISM: Artificial Sequence
<220> FEATURE:
<223> OTHER INFORMATION: Synthetic Construct

<400> SEQUENCE: 262
acacaggaag agacagcaat ccgaactgag agaagctttt gtctcttcct gtgt      54

<210> SEQ ID NO 263
<211> LENGTH: 54
<212> TYPE: DNA
<213> ORGANISM: Artificial Sequence
<220> FEATURE:
<223> OTHER INFORMATION: Synthetic Construct

<400> SEQUENCE: 263
acacaggaag agacacgttc agttactaac gtccttgttt gtctcttcct gtgt      54

<210> SEQ ID NO 264
<211> LENGTH: 54
<212> TYPE: DNA
<213> ORGANISM: Artificial Sequence
<220> FEATURE:
<223> OTHER INFORMATION: Synthetic Construct

<400> SEQUENCE: 264
acacaggaag agacaatggt gtagtccaca gcttcggtat gtctcttcct gtgt      54

<210> SEQ ID NO 265
<211> LENGTH: 54
<212> TYPE: DNA
<213> ORGANISM: Artificial Sequence
<220> FEATURE:
```

<223> OTHER INFORMATION: Synthetic Construct

<400> SEQUENCE: 265
acacaggaag agacataggc acacggtttc aggatctatt gtctcttcct gtgt    54

<210> SEQ ID NO 266
<211> LENGTH: 54
<212> TYPE: DNA
<213> ORGANISM: Artificial Sequence
<220> FEATURE:
<223> OTHER INFORMATION: Synthetic Construct

<400> SEQUENCE: 266
acacaggaag agacattcgg aaatctctgg atcatagctt gtctcttcct gtgt    54

<210> SEQ ID NO 267
<211> LENGTH: 54
<212> TYPE: DNA
<213> ORGANISM: Artificial Sequence
<220> FEATURE:
<223> OTHER INFORMATION: Synthetic Construct

<400> SEQUENCE: 267
acacaggaag agacaactca tcagtctagt gtaaacacct gtctcttcct gtgt    54

<210> SEQ ID NO 268
<211> LENGTH: 54
<212> TYPE: DNA
<213> ORGANISM: Artificial Sequence
<220> FEATURE:
<223> OTHER INFORMATION: Synthetic Construct

<400> SEQUENCE: 268
acacaggaag agacagtaga ttttccactc ctaccaacgt gtctcttcct gtgt    54

<210> SEQ ID NO 269
<211> LENGTH: 54
<212> TYPE: DNA
<213> ORGANISM: Artificial Sequence
<220> FEATURE:
<223> OTHER INFORMATION: Synthetic Construct

<400> SEQUENCE: 269
acacaggaag agacaccttc tgcactcaag tcctccagtt gtctcttcct gtgt    54

<210> SEQ ID NO 270
<211> LENGTH: 54
<212> TYPE: DNA
<213> ORGANISM: Artificial Sequence
<220> FEATURE:
<223> OTHER INFORMATION: Synthetic Construct

<400> SEQUENCE: 270
acacaggaag agacacttct gctccgaaga gaaagcctat gtctcttcct gtgt    54

<210> SEQ ID NO 271
<211> LENGTH: 54
<212> TYPE: DNA
<213> ORGANISM: Artificial Sequence
<220> FEATURE:
<223> OTHER INFORMATION: Synthetic Construct

<400> SEQUENCE: 271
acacaggaag agacactcag gatactgcta aggttaatct gtctcttcct gtgt    54

```
<210> SEQ ID NO 272
<211> LENGTH: 54
<212> TYPE: DNA
<213> ORGANISM: Artificial Sequence
<220> FEATURE:
<223> OTHER INFORMATION: Synthetic Construct

<400> SEQUENCE: 272
acacaggaag agacaagtct gactgccgat tatatctcgt gtctcttcct gtgt        54

<210> SEQ ID NO 273
<211> LENGTH: 54
<212> TYPE: DNA
<213> ORGANISM: Artificial Sequence
<220> FEATURE:
<223> OTHER INFORMATION: Synthetic Construct

<400> SEQUENCE: 273
acacaggaag agacaacttc gctcctcgtc acagctcaat gtctcttcct gtgt        54

<210> SEQ ID NO 274
<211> LENGTH: 54
<212> TYPE: DNA
<213> ORGANISM: Artificial Sequence
<220> FEATURE:
<223> OTHER INFORMATION: Synthetic Construct

<400> SEQUENCE: 274
acacaggaag agacatgtca ccacaattac actcctaact gtctcttcct gtgt        54

<210> SEQ ID NO 275
<211> LENGTH: 54
<212> TYPE: DNA
<213> ORGANISM: Artificial Sequence
<220> FEATURE:
<223> OTHER INFORMATION: Synthetic Construct

<400> SEQUENCE: 275
acacaggaag agacagaacc caaagacttt gatttctcgt gtctcttcct gtgt        54

<210> SEQ ID NO 276
<211> LENGTH: 54
<212> TYPE: DNA
<213> ORGANISM: Artificial Sequence
<220> FEATURE:
<223> OTHER INFORMATION: Synthetic Construct

<400> SEQUENCE: 276
acacaggaag agacaattac gatggtccta gaaaccaact gtctcttcct gtgt        54

<210> SEQ ID NO 277
<211> LENGTH: 54
<212> TYPE: DNA
<213> ORGANISM: Artificial Sequence
<220> FEATURE:
<223> OTHER INFORMATION: Synthetic Construct

<400> SEQUENCE: 277
acacaggaag agacatcact gtacttgttc gctatcggtt gtctcttcct gtgt        54

<210> SEQ ID NO 278
<211> LENGTH: 54
<212> TYPE: DNA
<213> ORGANISM: Artificial Sequence
<220> FEATURE:
<223> OTHER INFORMATION: Synthetic Construct
```

```
<400> SEQUENCE: 278
acacaggaag agacattccg gcactttaac ttcacgttct gtctcttcct gtgt          54

<210> SEQ ID NO 279
<211> LENGTH: 54
<212> TYPE: DNA
<213> ORGANISM: Artificial Sequence
<220> FEATURE:
<223> OTHER INFORMATION: Synthetic Construct

<400> SEQUENCE: 279
acacaggaag agacataaac caattccagg gtgataagct gtctcttcct gtgt          54

<210> SEQ ID NO 280
<211> LENGTH: 54
<212> TYPE: DNA
<213> ORGANISM: Artificial Sequence
<220> FEATURE:
<223> OTHER INFORMATION: Synthetic Construct

<400> SEQUENCE: 280
acacaggaag agacatccgt accagttcta agttgatcgt gtctcttcct gtgt          54

<210> SEQ ID NO 281
<211> LENGTH: 55
<212> TYPE: DNA
<213> ORGANISM: Artificial Sequence
<220> FEATURE:
<223> OTHER INFORMATION: Synthetic Construct

<400> SEQUENCE: 281
acacaggaag agacagcatg gattctgact tagaggcgtt tgtctcttcc tgtgt         55

<210> SEQ ID NO 282
<211> LENGTH: 54
<212> TYPE: DNA
<213> ORGANISM: Artificial Sequence
<220> FEATURE:
<223> OTHER INFORMATION: Synthetic Construct

<400> SEQUENCE: 282
acacaggaag agacacattt accgcggctg ctggcacgat gtctcttcct gtgt          54

<210> SEQ ID NO 283
<211> LENGTH: 54
<212> TYPE: DNA
<213> ORGANISM: Artificial Sequence
<220> FEATURE:
<223> OTHER INFORMATION: Synthetic Construct

<400> SEQUENCE: 283
acacaggaag agacagcgtg gactaccagg gtatcaaaat gtctcttcct gtgt          54

<210> SEQ ID NO 284
<211> LENGTH: 54
<212> TYPE: DNA
<213> ORGANISM: Artificial Sequence
<220> FEATURE:
<223> OTHER INFORMATION: Synthetic Construct

<400> SEQUENCE: 284
acacaggaag agacaattca tgctccaccg cttgtgcgat gtctcttcct gtgt          54

<210> SEQ ID NO 285
<211> LENGTH: 54
```

<212> TYPE: DNA
<213> ORGANISM: Artificial Sequence
<220> FEATURE:
<223> OTHER INFORMATION: Synthetic Construct

<400> SEQUENCE: 285
acacaggaag agacacttac ccgacaagga atttcgctat gtctcttcct gtgt    54

<210> SEQ ID NO 286
<211> LENGTH: 54
<212> TYPE: DNA
<213> ORGANISM: Artificial Sequence
<220> FEATURE:
<223> OTHER INFORMATION: Synthetic Construct

<400> SEQUENCE: 286
acacaggaag agacaagagc cgacatcgag gtgccaaact gtctcttcct gtgt    54

<210> SEQ ID NO 287
<211> LENGTH: 54
<212> TYPE: DNA
<213> ORGANISM: Artificial Sequence
<220> FEATURE:
<223> OTHER INFORMATION: Synthetic Construct

<400> SEQUENCE: 287
acacaggaag agacaaaccg tattaccgcg gctgctgaat gtctcttcct gtgt    54

<210> SEQ ID NO 288
<211> LENGTH: 54
<212> TYPE: DNA
<213> ORGANISM: Artificial Sequence
<220> FEATURE:
<223> OTHER INFORMATION: Synthetic Construct

<400> SEQUENCE: 288
acacaggaag agacacattt cacaacacga gctgacatct gtctcttcct gtgt    54

<210> SEQ ID NO 289
<211> LENGTH: 54
<212> TYPE: DNA
<213> ORGANISM: Artificial Sequence
<220> FEATURE:
<223> OTHER INFORMATION: Synthetic Construct

<400> SEQUENCE: 289
acacaggaag agacattcgc ttcactttgt atctgccatt gtctcttcct gtgt    54

<210> SEQ ID NO 290
<211> LENGTH: 54
<212> TYPE: DNA
<213> ORGANISM: Artificial Sequence
<220> FEATURE:
<223> OTHER INFORMATION: Synthetic Construct

<400> SEQUENCE: 290
acacaggaag agacaggtat cgtcggttat aacgcttcat gtctcttcct gtgt    54

<210> SEQ ID NO 291
<211> LENGTH: 54
<212> TYPE: DNA
<213> ORGANISM: Artificial Sequence
<220> FEATURE:
<223> OTHER INFORMATION: Synthetic Construct

<400> SEQUENCE: 291

```
acacaggaag agacacacaa actgattcag actctgggct gtctcttcct gtgt      54
```

<210> SEQ ID NO 292
<211> LENGTH: 54
<212> TYPE: DNA
<213> ORGANISM: Artificial Sequence
<220> FEATURE:
<223> OTHER INFORMATION: Synthetic Construct

<400> SEQUENCE: 292

```
acacaggaag agacattggc cagcctagcc ttctccgatt gtctcttcct gtgt      54
```

<210> SEQ ID NO 293
<211> LENGTH: 54
<212> TYPE: DNA
<213> ORGANISM: Artificial Sequence
<220> FEATURE:
<223> OTHER INFORMATION: Synthetic Construct

<400> SEQUENCE: 293

```
acacaggaag agacactcat cgagttcaca gcctgtgcat gtctcttcct gtgt      54
```

<210> SEQ ID NO 294
<211> LENGTH: 54
<212> TYPE: DNA
<213> ORGANISM: Artificial Sequence
<220> FEATURE:
<223> OTHER INFORMATION: Synthetic Construct

<400> SEQUENCE: 294

```
acacaggaag agacagtcat gatttaggga ccttagatgt gtctcttcct gtgt      54
```

<210> SEQ ID NO 295
<211> LENGTH: 54
<212> TYPE: DNA
<213> ORGANISM: Artificial Sequence
<220> FEATURE:
<223> OTHER INFORMATION: Synthetic Construct

<400> SEQUENCE: 295

```
acacaggaag agacaccgca tcttcggtac atgacttgat gtctcttcct gtgt      54
```

<210> SEQ ID NO 296
<211> LENGTH: 54
<212> TYPE: DNA
<213> ORGANISM: Artificial Sequence
<220> FEATURE:
<223> OTHER INFORMATION: Synthetic Construct

<400> SEQUENCE: 296

```
acacaggaag agacacgtca catcctttag gttcaggaat gtctcttcct gtgt      54
```

<210> SEQ ID NO 297
<211> LENGTH: 54
<212> TYPE: DNA
<213> ORGANISM: Artificial Sequence
<220> FEATURE:
<223> OTHER INFORMATION: Synthetic Construct

<400> SEQUENCE: 297

```
acacaggaag agacaacttc taacaccagt gcaaagctat gtctcttcct gtgt      54
```

<210> SEQ ID NO 298
<211> LENGTH: 54
<212> TYPE: DNA
<213> ORGANISM: Artificial Sequence

```
<220> FEATURE:
<223> OTHER INFORMATION: Synthetic Construct

<400> SEQUENCE: 298
acacaggaag agacaagcat accgatagcg ttcgttctgt gtctcttcct gtgt        54

<210> SEQ ID NO 299
<211> LENGTH: 54
<212> TYPE: DNA
<213> ORGANISM: Artificial Sequence
<220> FEATURE:
<223> OTHER INFORMATION: Synthetic Construct

<400> SEQUENCE: 299
acacaggaag agacacattg ttggcgcaag aaaacttatt gtctcttcct gtgt        54

<210> SEQ ID NO 300
<211> LENGTH: 54
<212> TYPE: DNA
<213> ORGANISM: Artificial Sequence
<220> FEATURE:
<223> OTHER INFORMATION: Synthetic Construct

<400> SEQUENCE: 300
acacaggaag agacatttcg ctgagtcgat actggagact gtctcttcct gtgt        54

<210> SEQ ID NO 301
<211> LENGTH: 54
<212> TYPE: DNA
<213> ORGANISM: Artificial Sequence
<220> FEATURE:
<223> OTHER INFORMATION: Synthetic Construct

<400> SEQUENCE: 301
acacaggaag agacaagggt ggtatctcaa gagtgactct gtctcttcct gtgt        54

<210> SEQ ID NO 302
<211> LENGTH: 54
<212> TYPE: DNA
<213> ORGANISM: Artificial Sequence
<220> FEATURE:
<223> OTHER INFORMATION: Synthetic Construct

<400> SEQUENCE: 302
acacaggaag agacagtgcg cattttgcct tcgtaatgat gtctcttcct gtgt        54

<210> SEQ ID NO 303
<211> LENGTH: 54
<212> TYPE: DNA
<213> ORGANISM: Artificial Sequence
<220> FEATURE:
<223> OTHER INFORMATION: Synthetic Construct

<400> SEQUENCE: 303
acacaggaag agacaagtcc tcggcagaca tgtcaaacat gtctcttcct gtgt        54

<210> SEQ ID NO 304
<211> LENGTH: 54
<212> TYPE: DNA
<213> ORGANISM: Artificial Sequence
<220> FEATURE:
<223> OTHER INFORMATION: Synthetic Construct

<400> SEQUENCE: 304
acacaggaag agacattagc cctgttcgtt gccatctcct gtctcttcct gtgt        54
```

```
<210> SEQ ID NO 305
<211> LENGTH: 54
<212> TYPE: DNA
<213> ORGANISM: Artificial Sequence
<220> FEATURE:
<223> OTHER INFORMATION: Synthetic Construct

<400> SEQUENCE: 305
acacaggaag agacaagagt cttatacggt actcccacct gtctcttcct gtgt        54

<210> SEQ ID NO 306
<211> LENGTH: 54
<212> TYPE: DNA
<213> ORGANISM: Artificial Sequence
<220> FEATURE:
<223> OTHER INFORMATION: Synthetic Construct

<400> SEQUENCE: 306
acacaggaag agacaaattg tcctggtctt cctgcgccgt gtctcttcct gtgt        54

<210> SEQ ID NO 307
<211> LENGTH: 54
<212> TYPE: DNA
<213> ORGANISM: Artificial Sequence
<220> FEATURE:
<223> OTHER INFORMATION: Synthetic Construct

<400> SEQUENCE: 307
acacaggaag agacacaagc cagatggtgc ctgagagtat gtctcttcct gtgt        54

<210> SEQ ID NO 308
<211> LENGTH: 54
<212> TYPE: DNA
<213> ORGANISM: Artificial Sequence
<220> FEATURE:
<223> OTHER INFORMATION: Synthetic Construct

<400> SEQUENCE: 308
acacaggaag agacacgctg tgtcacctaa aatggccaat gtctcttcct gtgt        54

<210> SEQ ID NO 309
<211> LENGTH: 54
<212> TYPE: DNA
<213> ORGANISM: Artificial Sequence
<220> FEATURE:
<223> OTHER INFORMATION: Synthetic Construct

<400> SEQUENCE: 309
acacaggaag agacatctgt cattgccatc tgtgtcacct gtctcttcct gtgt        54

<210> SEQ ID NO 310
<211> LENGTH: 54
<212> TYPE: DNA
<213> ORGANISM: Artificial Sequence
<220> FEATURE:
<223> OTHER INFORMATION: Synthetic Construct

<400> SEQUENCE: 310
acacaggaag agacatatga ccagccacct cttccacact gtctcttcct gtgt        54

<210> SEQ ID NO 311
<211> LENGTH: 54
<212> TYPE: DNA
<213> ORGANISM: Artificial Sequence
<220> FEATURE:
<223> OTHER INFORMATION: Synthetic Construct
```

<400> SEQUENCE: 311
acacaggaag agacagtctc tcctgtggaa gtacatcagt gtctcttcct gtgt    54

<210> SEQ ID NO 312
<211> LENGTH: 54
<212> TYPE: DNA
<213> ORGANISM: Artificial Sequence
<220> FEATURE:
<223> OTHER INFORMATION: Synthetic Construct

<400> SEQUENCE: 312
acacaggaag agacaactac aggcagcacg gtttgctcat gtctcttcct gtgt    54

<210> SEQ ID NO 313
<211> LENGTH: 54
<212> TYPE: DNA
<213> ORGANISM: Artificial Sequence
<220> FEATURE:
<223> OTHER INFORMATION: Synthetic Construct

<400> SEQUENCE: 313
acacaggaag agacagaact gtgttaagca agcttccgat gtctcttcct gtgt    54

<210> SEQ ID NO 314
<211> LENGTH: 54
<212> TYPE: DNA
<213> ORGANISM: Artificial Sequence
<220> FEATURE:
<223> OTHER INFORMATION: Synthetic Construct

<400> SEQUENCE: 314
acacaggaag agacactgct accccatgcg tacagcttct gtctcttcct gtgt    54

<210> SEQ ID NO 315
<211> LENGTH: 54
<212> TYPE: DNA
<213> ORGANISM: Artificial Sequence
<220> FEATURE:
<223> OTHER INFORMATION: Synthetic Construct

<400> SEQUENCE: 315
acacaggaag agacagcatt ccaagtgaga atctctttgt gtctcttcct gtgt    54

<210> SEQ ID NO 316
<211> LENGTH: 54
<212> TYPE: DNA
<213> ORGANISM: Artificial Sequence
<220> FEATURE:
<223> OTHER INFORMATION: Synthetic Construct

<400> SEQUENCE: 316
acacaggaag agacaaacta ttgttccatg ttgtgtttct gtctcttcct gtgt    54

<210> SEQ ID NO 317
<211> LENGTH: 54
<212> TYPE: DNA
<213> ORGANISM: Artificial Sequence
<220> FEATURE:
<223> OTHER INFORMATION: Synthetic Construct

<400> SEQUENCE: 317
acacaggaag agacaacctg gacttcttct ccttccttct gtctcttcct gtgt    54

<210> SEQ ID NO 318

-continued

```
<211> LENGTH: 54
<212> TYPE: DNA
<213> ORGANISM: Artificial Sequence
<220> FEATURE:
<223> OTHER INFORMATION: Synthetic Construct

<400> SEQUENCE: 318
acacaggaag agacatttct ccttcctttg tccagatttt gtctcttcct gtgt          54

<210> SEQ ID NO 319
<211> LENGTH: 54
<212> TYPE: DNA
<213> ORGANISM: Artificial Sequence
<220> FEATURE:
<223> OTHER INFORMATION: Synthetic Construct

<400> SEQUENCE: 319
acacaggaag agacaggtgt gagtgctctc ttgcctttgt gtctcttcct gtgt          54

<210> SEQ ID NO 320
<211> LENGTH: 54
<212> TYPE: DNA
<213> ORGANISM: Artificial Sequence
<220> FEATURE:
<223> OTHER INFORMATION: Synthetic Construct

<400> SEQUENCE: 320
acacaggaag agacatctac gtccttctca taagtgggtt gtctcttcct gtgt          54

<210> SEQ ID NO 321
<211> LENGTH: 54
<212> TYPE: DNA
<213> ORGANISM: Artificial Sequence
<220> FEATURE:
<223> OTHER INFORMATION: Synthetic Construct

<400> SEQUENCE: 321
acacaggaag agacaagacg atctactaat cctggccgct gtctcttcct gtgt          54

<210> SEQ ID NO 322
<211> LENGTH: 54
<212> TYPE: DNA
<213> ORGANISM: Artificial Sequence
<220> FEATURE:
<223> OTHER INFORMATION: Synthetic Construct

<400> SEQUENCE: 322
acacaggaag agacatctgt cagtctatct ggtgtctctt gtctcttcct gtgt          54

<210> SEQ ID NO 323
<211> LENGTH: 54
<212> TYPE: DNA
<213> ORGANISM: Artificial Sequence
<220> FEATURE:
<223> OTHER INFORMATION: Synthetic Construct

<400> SEQUENCE: 323
acacaggaag agacacttga ctatgtgcga cacaagagat gtctcttcct gtgt          54

<210> SEQ ID NO 324
<211> LENGTH: 30
<212> TYPE: DNA
<213> ORGANISM: Artificial Sequence
<220> FEATURE:
<223> OTHER INFORMATION: Synthetic Construct

<400> SEQUENCE: 324
```
tggaagcagg gcatttgtyg cttcagcacc                           30

<210> SEQ ID NO 325
<211> LENGTH: 28
<212> TYPE: DNA
<213> ORGANISM: Artificial Sequence
<220> FEATURE:
<223> OTHER INFORMATION: Synthetic Construct

<400> SEQUENCE: 325
tctacctgac cacctgtgtc ggtttggg                             28

<210> SEQ ID NO 326
<211> LENGTH: 25
<212> TYPE: DNA
<213> ORGANISM: Artificial Sequence
<220> FEATURE:
<223> OTHER INFORMATION: Synthetic Construct

<400> SEQUENCE: 326
tggaagcagg gcatttgtyg cttca                                25

<210> SEQ ID NO 327
<211> LENGTH: 23
<212> TYPE: DNA
<213> ORGANISM: Artificial Sequence
<220> FEATURE:
<223> OTHER INFORMATION: Synthetic Construct

<400> SEQUENCE: 327
ctgaccacct gtgtcggttt ggg                                  23

<210> SEQ ID NO 328
<211> LENGTH: 30
<212> TYPE: DNA
<213> ORGANISM: Artificial Sequence
<220> FEATURE:
<223> OTHER INFORMATION: Synthetic Construct

<400> SEQUENCE: 328
gtcaaaacag caaggtatta acttactgcc                           30

<210> SEQ ID NO 329
<211> LENGTH: 30
<212> TYPE: DNA
<213> ORGANISM: Artificial Sequence
<220> FEATURE:
<223> OTHER INFORMATION: Synthetic Construct

<400> SEQUENCE: 329
cttgcaccct tcgtattacc gcggctgctg                           30

<210> SEQ ID NO 330
<211> LENGTH: 25
<212> TYPE: DNA
<213> ORGANISM: Artificial Sequence
<220> FEATURE:
<223> OTHER INFORMATION: Synthetic Construct

<400> SEQUENCE: 330
gtcaaaacag caaggtatta actta                                25

<210> SEQ ID NO 331
<211> LENGTH: 25
<212> TYPE: DNA

<213> ORGANISM: Artificial Sequence
<220> FEATURE:
<223> OTHER INFORMATION: Synthetic Construct

<400> SEQUENCE: 331
acccttcgta ttaccgcggc tgctg                                    25

<210> SEQ ID NO 332
<211> LENGTH: 30
<212> TYPE: DNA
<213> ORGANISM: Artificial Sequence
<220> FEATURE:
<223> OTHER INFORMATION: Synthetic Construct

<400> SEQUENCE: 332
agaaccataa cgtcctattc tattattcca                               30

<210> SEQ ID NO 333
<211> LENGTH: 30
<212> TYPE: DNA
<213> ORGANISM: Artificial Sequence
<220> FEATURE:
<223> OTHER INFORMATION: Synthetic Construct

<400> SEQUENCE: 333
ctgaatactg atacctccga ccgtccctat                               30

<210> SEQ ID NO 334
<211> LENGTH: 25
<212> TYPE: DNA
<213> ORGANISM: Artificial Sequence
<220> FEATURE:
<223> OTHER INFORMATION: Synthetic Construct

<400> SEQUENCE: 334
agaaccataa cgtcctattc tatta                                    25

<210> SEQ ID NO 335
<211> LENGTH: 25
<212> TYPE: DNA
<213> ORGANISM: Artificial Sequence
<220> FEATURE:
<223> OTHER INFORMATION: Synthetic Construct

<400> SEQUENCE: 335
tactgatacc tccgaccgtc cctat                                    25

<210> SEQ ID NO 336
<211> LENGTH: 15
<212> TYPE: DNA
<213> ORGANISM: Artificial Sequence
<220> FEATURE:
<223> OTHER INFORMATION: Synthetic Construct

<400> SEQUENCE: 336
tttacacagg aagag                                               15

<210> SEQ ID NO 337
<211> LENGTH: 13
<212> TYPE: DNA
<213> ORGANISM: Artificial Sequence
<220> FEATURE:
<223> OTHER INFORMATION: Synthetic Construct

<400> SEQUENCE: 337
tacacaggaa gag                                                 13

```
<210> SEQ ID NO 338
<211> LENGTH: 13
<212> TYPE: DNA
<213> ORGANISM: Artificial Sequence
<220> FEATURE:
<223> OTHER INFORMATION: Synthetic Construct

<400> SEQUENCE: 338
ctcttcctgt gta                                                         13

<210> SEQ ID NO 339
<211> LENGTH: 54
<212> TYPE: DNA
<213> ORGANISM: Artificial Sequence
<220> FEATURE:
<223> OTHER INFORMATION: Synthetic Construct

<400> SEQUENCE: 339
acacaggaag agacacatca ctcattaacg agctttgact gtctcttcct gtgt            54
```